United States Patent [19]
Albright et al.

[11] Patent Number: 5,104,869
[45] Date of Patent: Apr. 14, 1992

[54] RENIN INHIBITORS

[75] Inventors: Jay D. Albright, Nanuet, N.Y.; Charles Frederick, Upper Saddle River, N.J.; Jeremy I. Levin, Spring Valley, N.Y.; Fuk-Wah Sum, Pomona, N.Y.; Marvin F. Reich, Suffern, N.Y.

[73] Assignee: American Cyanamid Company, Wayne, N.J.

[21] Appl. No.: 605,067

[22] Filed: Oct. 25, 1990

Related U.S. Application Data

[63] Continuation-in-part of Ser. No. 419,810, Oct. 11, 1989, abandoned.

[51] Int. Cl.$^5$ .............. A61K 31/34; A61K 31/38; A61K 31/41; A61K 31/415
[52] U.S. Cl. .............. 514/212; 514/227.8; 514/228.2; 514/231.5; 514/233.5; 514/235.2; 514/235.8; 514/236.5; 514/236.8; 514/252; 514/253; 514/336; 514/337; 514/339; 514/340; 514/341; 514/342; 514/343; 514/365; 514/374; 514/376; 514/383; 514/397; 514/406; 514/414; 514/422; 514/438; 514/443; 514/444; 514/469; 514/471; 540/524; 544/58.4; 544/132; 544/133; 544/137; 544/139; 544/140; 544/141; 544/146; 544/152; 544/153; 544/369; 544/370; 544/372; 544/373; 544/376; 544/379; 546/269; 546/273; 546/274; 546/275; 546/276; 546/278; 546/279; 546/280; 546/281; 546/283; 546/284; 548/204; 548/231; 548/236; 548/266.2; 548/266.4; 548/266.6; 548/667.6; 548/336; 548/343; 548/344; 548/374; 548/378; 548/468; 548/517; 548/518; 548/525; 548/527; 548/561; 549/58; 549/59; 549/60; 549/76; 549/407; 549/496

[58] Field of Search .......... 548/204, 231, 236, 266.2, 548/266.4, 266.6, 267.6, 336, 343, 344, 374, 378, 468, 517, 518, 525, 527, 561; 549/58, 59, 60, 76, 407, 496; 514/212, 227.8, 228.2, 231.5, 233.5, 235.2, 235.8, 236.5, 236.8, 252, 253, 336, 337, 339, 340, 341, 342, 343, 365, 374, 376, 383, 397, 406, 414, 422, 438, 443, 444, 469, 471; 540/524; 544/58.4, 132, 133, 137, 139, 140, 141, 146, 152, 153, 369, 370, 372, 373, 376, 379; 546/269, 273, 274, 275, 276, 278, 279, 280, 281, 283, 284

[56] References Cited

U.S. PATENT DOCUMENTS

| | | | |
|---|---|---|---|
| 4,656,269 | 4/1987 | Iizuka et al. | 544/139 |
| 4,663,310 | 5/1987 | Bock et al. | 514/15 |
| 4,711,958 | 4/1987 | Iizuka et al. | 544/139 |
| 4,782,043 | 11/1988 | Boger et al. | 514/11 |
| 4,826,815 | 5/1989 | Luly et al. | 514/19 |
| 4,826,958 | 5/1989 | Sham et al. | 530/331 |
| 4,839,357 | 6/1989 | Patchett et al. | 514/235.8 |
| 4,885,292 | 12/1989 | Ryono et al. | 514/211 |
| 4,927,809 | 5/1990 | Stein et al. | 514/400 X |
| 4,981,843 | 1/1991 | Ryono et al. | 514/18 |

FOREIGN PATENT DOCUMENTS

| | | |
|---|---|---|
| 206807 | 8/1986 | European Pat. Off. |
| 190891 | 12/1986 | European Pat. Off. |
| 231919 | 8/1987 | European Pat. Off. |
| 3001890 | 1/1989 | European Pat. Off. |

OTHER PUBLICATIONS

Rosenberg et al., Chemical Abstracts, vol. 111 (1989) 214,942t.
Boger et al., Nature (1983), 303: 81–84.
Iizuka et al., J. Med. Chem. (1988), 31, 701–704.
Iizuka et al., J. Med. Chem., (1988), 31, 2277.
Hanson et al., Biochem. Biophys. Res. Comm. (1989), 160, 1–5.

Primary Examiner—Richard L. Raymond
Attorney, Agent, or Firm—Kenneth J. Dow

[57] ABSTRACT

Renin inhibiting compounds containing a single α-amino acid of the formula:

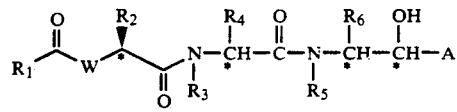

and analogs thereof which inhibit the substrate-cleaving acting or renin, pharmaceutical compositions containing these compounds, processes for producing the compounds and methods of treating hypertension which employ the novel renin inhibitors.

38 Claims, No Drawings

RENIN INHIBITORS

This is a continuation-in-part of copending application Ser. No. 07/419,810, filed on Oct. 11, 1989, now abandoned.

FIELD OF THE INVENTION

This invention relates to new compounds containing a single α-amino acid which inhibit renin and are thus useful in treating hypertension.

BACKGROUND OF THE INVENTION

Renin is an endopeptidase which plays n important role in the control of blood pressure. The renin angiotensin system is a multiregulated proteolytic cascade in which renin cleaves the protein substrate angiotensinogen to give the relatively inactive decapeptide angiotensin I. Angiotensin converting enzyme (ACE) catalyses the removal of the terminal dipeptide from angiotensin I to form the highly active octapeptide angiotensin II which exhibits potent pressor activity. In addition to its direct vasoconstricting effect, angiotensin II also stimulates the adrenal cortex to release aldosterone, which leads to sodium retention and a rise in extracellular fluid volume. Thus, the renin-angiotensin system plays a key role in the regulation of blood pressure and is implicated in some forms of hypertension.

In an effort to develop agents useful in the treatment of hypertension, compounds called ACE inhibitors have been developed which inhibit angiotensin I converting enzyme thereby blocking the generation of angiotensin II and its vasopressive effect; these include captopril and enalapril maleate. Similarly, effective inhibitors of renin have been sought which would reduce the release of angiotensin I and ultimately lead to a reduction in the circulating level of angiotensin II. Thus, renin inhibitors would be useful alternatives to ACE inhibitors as therapeutic agents in the treatment of hypertension and congestive heart failure.

A number of prior art references have described peptide compounds that have activity as renin inhibitors. For example, Boger et al., Nature, 303, 81–84, (1983) describe peptide renin inhibitors containing the amino acid statine. See also Veber et al. U.S. Pat Nos. 4,384,994 and 4,478,826. However, because these compounds are peptides, many of them are unsuitable for oral administration because of their proteolytic lability and poor absorption from the digestive tract. Smaller peptides that are better absorbed orally have proven to be poor inhibitors of renin. Recent efforts have been focused on formulating compounds which are effective orally yet retain high potency as inhibitors of human renin.

Recently, Iizuka and coworkers have described peptide renin inhibitors containing an unnatural amino acid, norstatine, (J. Med. Chem. Vol. 31, 701–701, 1988) which are active orally.

Other compounds having renin inhibiting activity have been disclosed which involve modifications to the N-terminal units, for example, Luly et al. U.S. Pat. No. 4,826,815, Sham, et al. U.S. Pat. No. 4,826,958, Iizuka et al. EP-0,206,807-A3, EP-0,190,891-A2, U.S. Pat. No. 4,656,269 and Hanson et al. Biochem Biophys. Res. Comm., 160, 1–5 (1989). Certain modifications to the central amino acid structure have also been tried, see for example, Patchett et al. U.S. Pat. No. 4,839,357, and Bock et al. U.S. Pat. No. 4,663,310. Finally, modifications in the C-terminal substituents are disclosed in Boger et al. U.S. Pat. No. 4,782,043 and published European Patent Application 231-919A. The latter reference discloses compounds having heterocyclic nitrogen containing rings of 5 or 6 carbon atoms at the C-terminal unit.

The present invention relates to structurally novel renin inhibitors containing a single α-amino acid. The present compounds differ from the prior art in the particular substituents at the N-terminal, the central α-amino acid and/or the C-terminal units.

SUMMARY OF THE INVENTION

This invention relates to new compounds of general formula I which contain a single α-amino acid.

FORMULA I

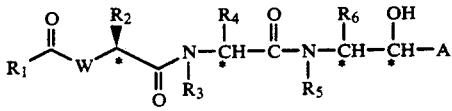

wherein
$R_1$ is:

O-lower alkyl($C_2$–$C_6$); —N[lower alkyl($C_1$–$C_6$)]$_2$; OH

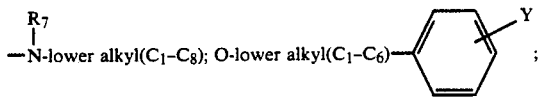

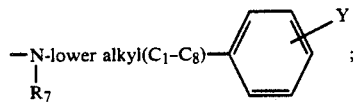

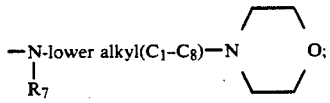

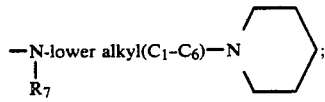

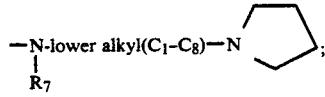

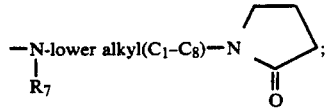

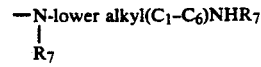

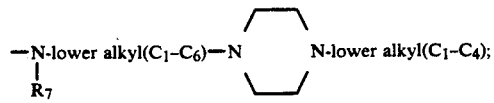

-continued

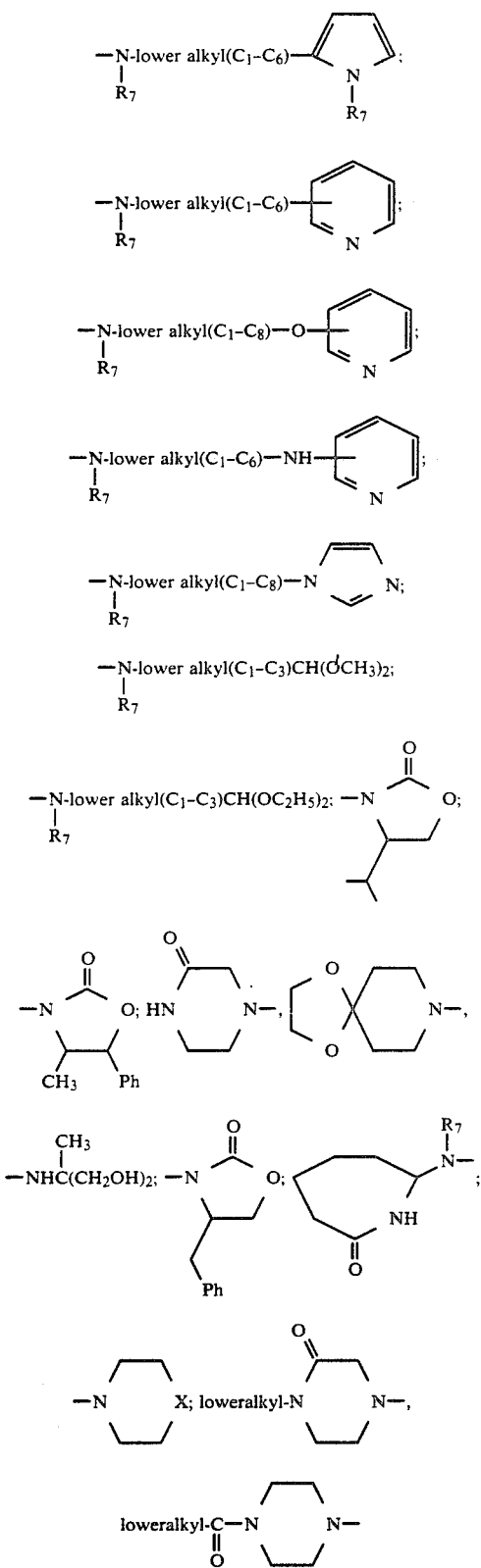

where X = S, O, SO, SO$_2$, NH, N-loweralkyl and Y is OCH$_3$, CH$_3$, F, Cl, or di or tri OCH$_3$ groups; R$_7$ is hydrogen or lower alkyl(C$_1$–C$_3$); R$_2$ is phenylmethyl, (4-methoxypheny)methyl, (3,4-dimethoxyphenyl)methyl, (4-chlorophenyl)methyl, (3-trifluoromethylphenyl)methyl, (3,4,5-trimethoxyphenyl)methyl, 1-naphthalenylmethyl, (2-thienyl)methyl, (3-indolyl)methyl, (benzo[b]thien-3-yl)methyl, (benzo[b]thien-2-yl)methyl, (3-benzofuranyl)methyl, (2-benzofuranyl)methyl; cyclohexylmethyl; R$_3$ is hydrogen or methyl; R$_4$ is 4-(imidazolyl)CH$_2$X—, alkyl(C$_1$–C$_8$), —alkyl(C$_1$–C$_4$)NH$_2$, phenylmethyl, cyclohexylmethyl, —X—alkyl(C$_1$–C$_8$), —(CH$_2$)$_n$N[lower alkyl(C$_1$–C$_3$)]$_2$, —(CH$_2$)$_n$NH—lower alkyl(C$_1$–C$_3$)], X-cyclohexyl, —(CH$_2$)$_n$—X-alkyl(C$_1$–C$_3$), —X—CH$_2$CH$_2$N[alkyl(-C$_1$–C$_3$)$_2$ (where X is —O— or —S—and n is 1 to 4) and moieties of the formulae:

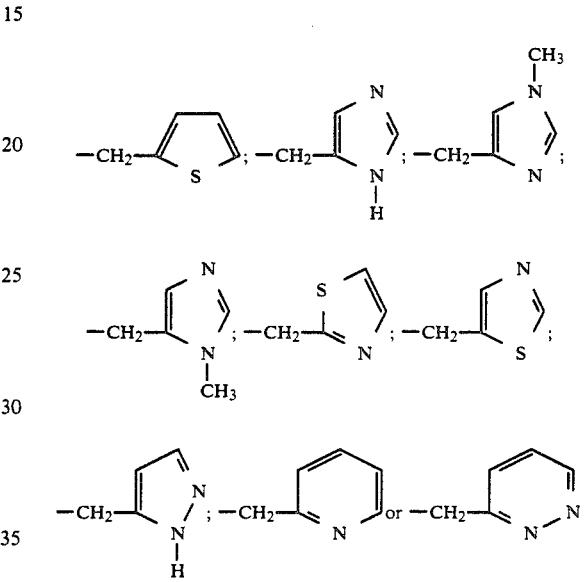

R$_5$ is hydrogen or methyl;
R$_6$ is alkyl(C$_1$–C$_6$), phenylmethyl, cyclohexylmethyl, —(CH$_2$)$_n$—X-alkyl(C$_1$–C$_3$) or

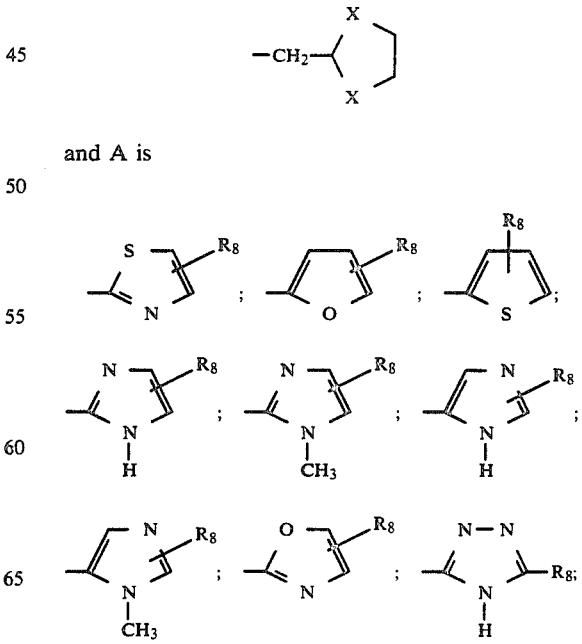

and A is

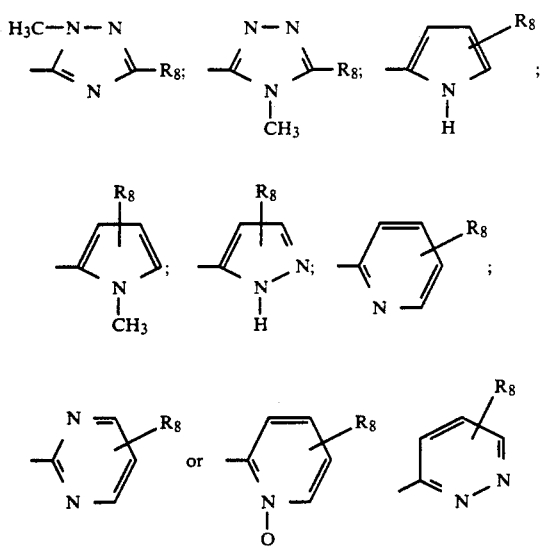

where $R_8$ is hydrogen, alkyl($C_1-C_3$) or $COR_9$, where $R_9$ is $NH_2$, OH, —O-alkyl($C_1-C_4$), —NH-alkyl($C_1-C_4$), —N[alkyl($C_1-C_3$)]$_2$, lower alkyl ($C_1-C_6$) and where W is $CH_2$ or O.

In the formula I the asterisks denote asymmetric carbon atoms. The asymmetric center at the carbon attached to the $R_2$ substituent of the N-terminal unit has the R configuration when W is $CH_2$ and the S configuration when W is O.

DETAILED DESCRIPTION OF THE INVENTION

Within the group of compounds defined by the formula I, certain subgroups of compounds are preferred. Broadly preferred are those compounds where the α-amino acids of formula II have the natural L configuration.

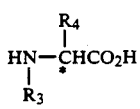

FORMULA II

Especially preferred in the C-terminal units are compounds where the C-terminal units are those of the formula III, with an anti(threo)relationship between the amino group and the hydroxyl group. Most preferred of the 1-amino-2-hydroxy compounds of formula III are those diastereomers with 1S configuration.

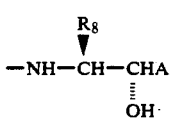

FORMULA III

Most preferred of the compounds of formula I, wherein the C-terminal group is represented by formula III, are those compounds wherein $R_2$ is phenylmethyl, 1-naphthalenylmethyl, (3-indoyl)methyl, (benzo[b]thien-3-yl)methyl, (3-benzofuranyl)methyl and $R_2$ in the N-terminal unit of formula IV is the R (W=$CH_2$) or the S (W=O) configuration (same configuration as L α-amino acids),

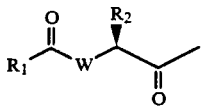

FORMULA IV $R_4$ is 4-(imidazolyl)$CH_2X$—, alkyl($C_1-C_4$)$NH_2$, —($CH_2$)$_n$-NHlower alkyl($C_1-C_3$), —($CH_2$)$_n$N[lower alkyl($C_1-C_3$)]$_2$, (4-imidazolyl)methyl, (3-pyrazolyl)methyl, —X—$CH_2CH_2$N[alkyl($C_1-C_3$)]$_2$, (3-pyridinyl)methyl, —X—CH($CH_3$)$_2$; $R_6$ is cyclohexylmethyl or

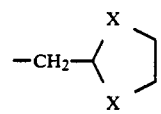

and A is

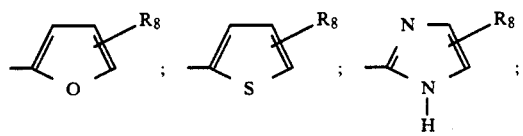

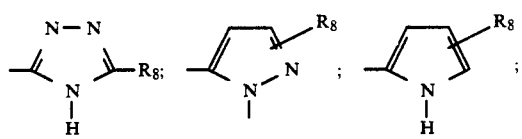

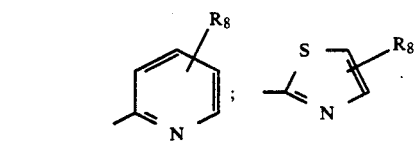

where $R_8$ is hydrogen or $COR_9$
where $R_9$ is as defined in claim 1.

The products of formula I and the preferred subgroups can be prepared by various synthetic procedures; either coupling the N-terminal unit (1) to the central α-amino acid (2) followed by coupling of α-amino acid derivatives (4) to the 1-amino-2-hydroxy C-terminal unit (5) (Scheme I) or first coupling the central α-amino acid derivative (6) to the 1-amino-2-hydroxy unit (5), followed by attachment of the N-terminal unit (1) to the α-amino acid derivative (7) (Scheme II).

Scheme I

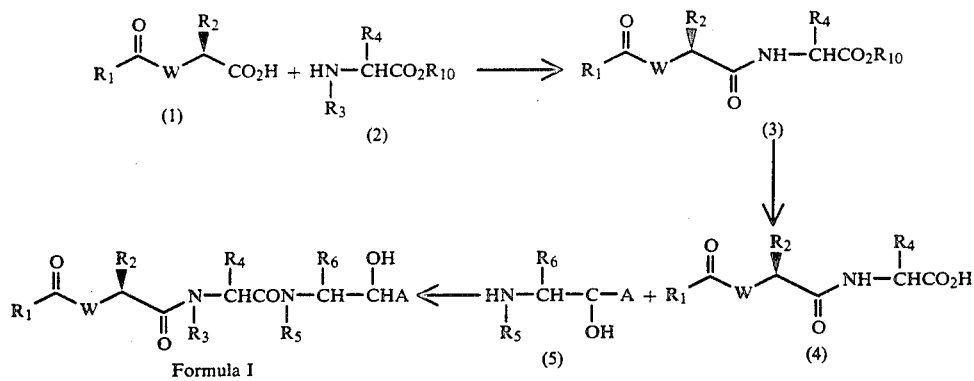

$R_{10}$ is a suitable blocking group for the carboxyl group such as t-butyl, lower alkoxy or benzyl.

Scheme II

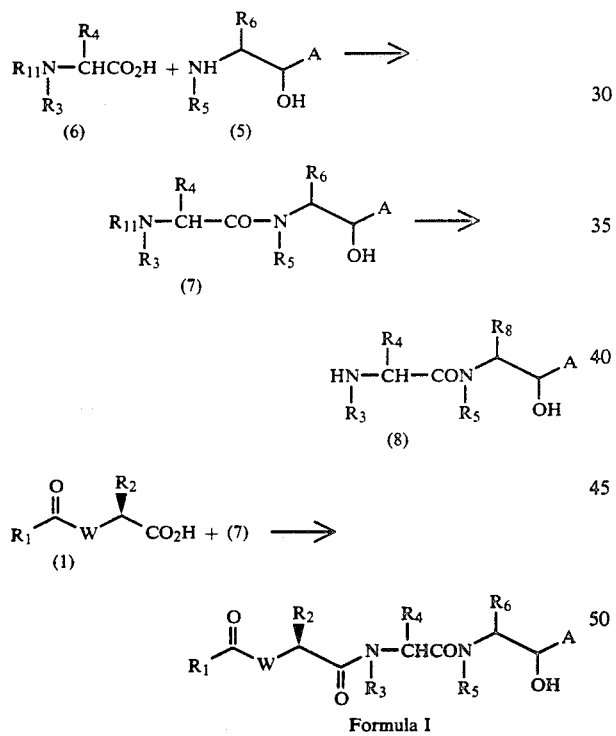

$R_{11}$ is a suitable blocking group for the amino group of the α-amino acid. Suitable blocking groups are t-butyloxycarbonyl, benzyloxycarbonyl and the like used in peptide synthesis.

Alternatively, certain of the products of this invention can be prepared by introduction of the $R_1$ groups in the last step of the synthesis. A derivative of formula (9) is prepared and the carboxy protecting group $R_{12}$ removed to give a derivative (10) with a free carboxyl group. Activation of carboxyl group and coupling with an $R_1H$ group where $R_1$ has been previously defined gives the products of formula I (W=CH$_2$) (Scheme III).

Scheme III

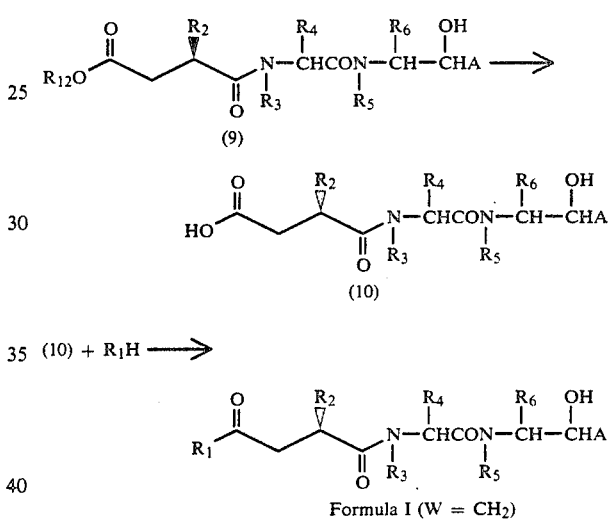

$R_{12}$ is a suitable blocking group such as t-butyl, benzyl and the like.

Intermediate 1-amino-2-hydroxy compounds are prepared by reacting an N-blocked α-amino aldehyde of formula (12) (wherein the $R_{13}$ blocking group may be t-butyloxycarbonyl, benzyloxycarbonyl, triphenylmethyl and the like) with anions of heterocycles A. Separation of diastereomers and removal of the amino blocking group gives intermediates (14) (Scheme IV). Illustrated is the synthesis of the preferred diastereometers from L α-aminoaldehydes to give the preferred diastereomers of formula (14) with the R,S configurations as noted.

The intermediates (14) are then reacted with an N-protected α-amino acid (6) activated with a peptide coupling reagent or as the acid chlorides to give N-protected derivatives (7). The preferred α-amino acids (6) are those which have the L-configuration. In the heterocyclic anions represented by $M^+A^-$, the symbol $M^+$ represented a metal (or its equivalent) such as $Li^+$, $K^+$ or $MgCl^+$, $MgBr^+$, $ZnCl^+$, $ZnBr^+$, $CeCl_2^+$ and the like or trimethylsilyl. In the case where M represents a trimethylsilyl group, the reaction is carried out with an equivalent of fluoride anion such as cesium fluoride. When A is a 2-thiazole and M is trimethylsilyl, the reaction is carried out at 0° C. to 25° C. without fluoride anion. When M+ represents a metal the reactions are carried out in a solvent such as tetrahydrofuran at −78° C. to −30° C. for one to five hours.

Scheme IV

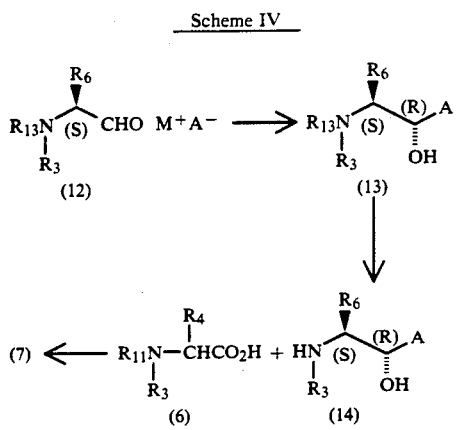

Intermediates of formula (13) may be prepared by reaction of M+A− (where A is a moiety as previously defined) with N-methyl-N-methoxy amides of formula (12a) to give the keto derivates (12b). Reduction of the keto derivate (12b) with hydrides such as sodium borohydride, lithium or potassium tri-sec-butylborohydride or triethylsilane gives the intermediates (13a) as a pair of diastereomers. The amount of each diastereomer in the mixture depends on the structure of the hydride reducing reagent and reaction conditions. In general, lithium and potassium tri-sec-butylborohydrides give selectively diasteromer (13).

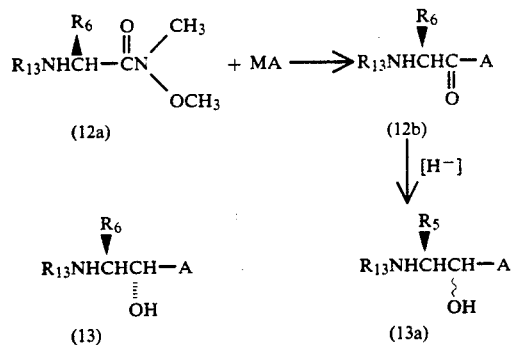

The intermediate N-terminal units (23) may be prepared in the following manner (Scheme V). The R,S-derivatives are prepared by the Stobbe condensation of diethyl succinate (15) with the appropriate arylaldehydes to the monoethyl ester derivatives (16). These derivatives may be coupled to an appropriate primary or secondary amine to give derivatives (17) which on hydrogenation afford the ethyl esters (18) of the penultimate desired acids (19). Direct hydrogenation of the Stobbe products (16) gives the racemic monoethyl ester derivatives (20) which may be coupled to an appropriate primary or secondary amine to afford the ethyl ester compounds (18). Hydrolysis of the ester gives the α-substituted acids of formula (19). Alternatively, the Stobbe products (16) can be hydrogenated to afford the saturated ethyl esters (20) may be resolved to give the desired (R) enantiomer (21) or the derivatives (16) may be hydrogenated under asymmetric hydrogenation conditions to give directly the (R) enantiomer (21).

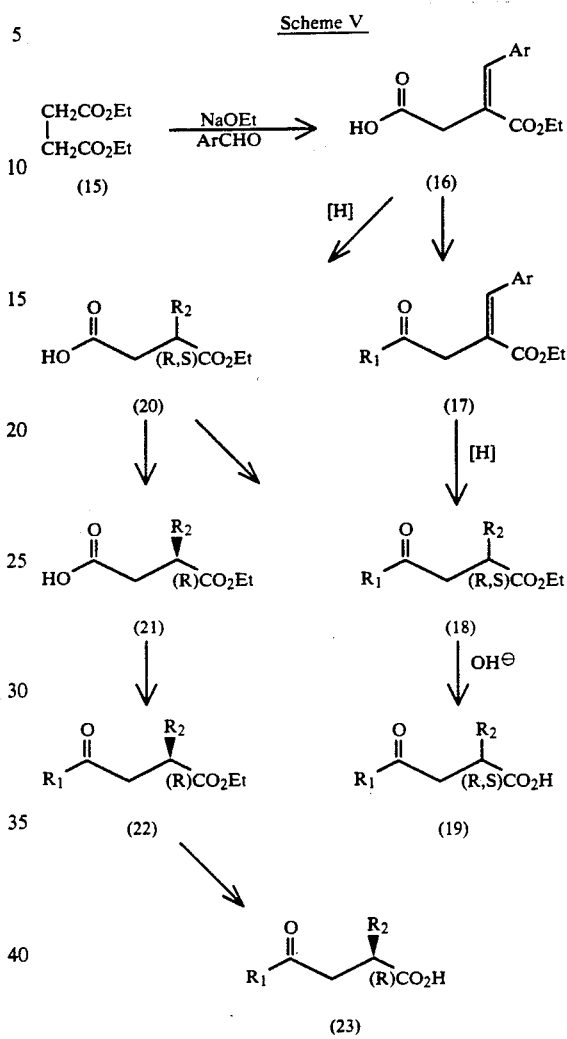

Asymmetric hydrogenation of Stobbe type products (16) have been described by H. Kawano, et al., *Tetrahedron Letters.* 28 (17) 1905 (1987).

The entiomerically pure N-terminal units (23) may be synthesized via N-acyl-4-substituted-2-oxazolidinones (a chiral synthon) according to the procedures of D. A. Evan, et al., *J. Am. Chem. Soc.*, 108, 6757 (1986) *Tetrahedron Letters,* 28, 6141 (1987) and reference therein (Scheme VI). Activation of carboxylic acid derivatives (29), (27) and (31) may be carried out with peptide coupling reagents such as:

1) N,N'-Dicyclohexylcarbodiimide plus 1-hydroxybenzotriazole
2) Benzotriazol-1-yloxytris-(dimethylamino)phosphonium hexafluorophosphate (BOP-reagent)
3) N,N'-Bis[2-oxo-3-oxazolidinyl]phosphorodiamidic chloride (BOB-Cl)
4) Diphenylphosphinyl chloride (DPP-Cl)
5) Diethoxyphosphoryl cyanide
6) 2-Chloro-1-methylpyridinium iodide
7) Phenyl dichlorophosphate plus imidazole and the like.

Scheme VI

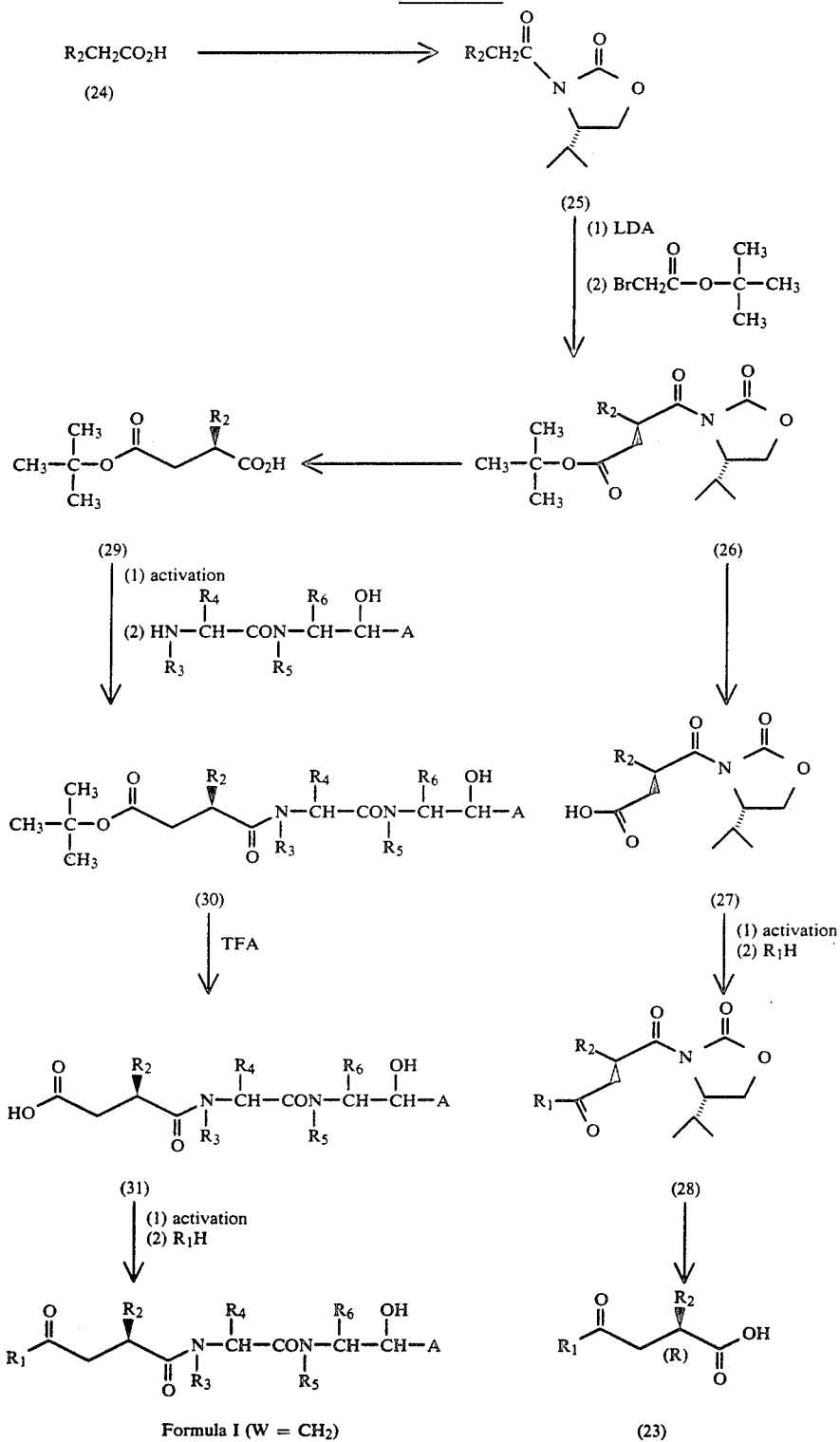

The compounds of formula I are active inhibitors of renin.

Biological Evaluation

Renin inhibitors have been shown to lower blood pressure in primates, [J. Hypertension, 1, 399 (1983), J. Hypertension, 1 (suppl 2), 189 (1983)] and in man, [Lancet II, 1486 (1983), Trans. Assoc. Am. Physicians, 96, 365 (1983), J. Hypertension, 3, 653 (1985)] and thus are potentially useful in the control of hypertension.

The novel compounds of formula I are new peptide renin inhibitors and are useful in the treatment of hypertension in warm-blooded animals, as established in the following test.

Radioimmunoassay Screen for Renin Inhibitors

The in vitro method for the screening of anti-renin compounds involves, first, angiotensin I generation, and second, the quantitation of the angiotensin I produced by radioimmunoassay.

Angiotensin I Generation

The incubation medium consisted of 20 µl of purified human plasma angiotensinogen (1); 10 µl of human kidney renin (2); 5 µl of phenylmethylsulfonyl fluoride; 10 µl of disodium EDTA (10 mM); 10 µl of antirenin compound ($5 \times 10^{-3}$, $5 \times 10^{-4}$, $5 \times 10^{-5}$) in dimethylformamide, or ethanol and a suitable amount of maleate buffer (77 mM, pH 6.0) to make a final volume of 500 µl. The reaction mixture was incubated for one hour at 37° C. and the enzymatic reaction was stopped by placing the tube in ice-cold water. The angiotensin I generated during the incubation was measured by a radioimmunoassay plasma renin activity kit (Clinical Assays, Inc.).

Radioimmunoassay Procedure

The incubation medium consisted of either 100 µl aliquots of the above reaction mixture or a standard amount of angiotensin I; 1000 µl of phosphate buffer (100 mM, pH 7.6) and 100 µl of ($^{125}$I)angiotensin in a gamma-coat, tube. After three hours of incubation at room temperature, the tubes were decanted, and the radioactivity of each tube was determined in a gamma counter. Duplicate determinations were performed for each incubation. The results were expressed in ng of angiotensin I generated per ml of generation medium per hour of incubation (ng/AI/ml/hr).

The results of this test on representative compounds of this invention appear in Table I, expressed as an IC$_{50}$.

(1) The human plasma angiotensinogen derived from the blood of a woman receiving oral contraceptive pills was purified by chromatography on a pepstatinaminohexyl-agarose column.

(2) Human renin was prepared from human kidney.

TABLE I

| Structure | Renin Inhibiton IC$_{50}$ (M) |
|---|---|
| [structure 1: morpholine-N–C(O)–CH$_2$–CH(CH$_2$Ph)–C(O)–Leu–NH–CH(CH$_2$Cy)(OH)–thiazole] | $8.0 \times 10^{-5}$ |
| [structure 2: morpholine-N–C(O)–CH$_2$–CH(CH$_2$Ph)–C(O)–His–NH–CH(CH$_2$Cy)(OH)–thiazole] | $1.5 \times 10^{-5}$ |
| [structure 3: (CH$_3$)$_3$C–NH–C(O)–CH$_2$–CH(CH$_2$Ph)–C(O)–Leu–NH–CH(iBu)(OH)–thiazole] | $6.7 \times 10^{-5}$ |
| [structure 4: (CH$_3$)$_3$C–NH–C(O)–CH$_2$–CH(CH$_2$Ph)–C(O)–His–NH–CH(iBu)(OH)–thiazole] | $6.5 \times 10^{-5}$ |

TABLE I-continued

| Structure | Renin Inhibiton IC$_{50}$ (M) |
|---|---|
| (tert-butyl ester, naphthylmethyl, Leu-NH, isopropyl, thiazole, OH) | $5.5 \times 10^{-7}$ |
| (tert-butyl ester, thienylmethyl, Leu-NH, isopropyl, thiazole, OH) | $1 \times 10^{-4}$ |
| (morpholine amide, naphthylmethyl, Leu-NH, isopropyl, thiazole, OH) | $2.5 \times 10^{-7}$ |
| (phenethylamide, naphthylmethyl, Leu-NH, isopropyl, thiazole, OH) | $7.3 \times 10^{-7}$ |
| (3,4-dimethoxyphenethylamide, naphthylmethyl, Leu-NH, isopropyl, thiazole, OH) | $6.8 \times 10^{-7}$ |

TABLE I-continued

| Structure | Renin Inhibiton IC$_{50}$ (M) |
| --- | --- |
| (morpholine-CO-CH$_2$-CH(CH$_2$-2,3,4-trimethoxyphenyl)-CO-His-NH-CH(iBu)-CH(OH)-thiazole) | $2.8 \times 10^{-6}$ |
| (imidazolyl-N(CH$_2$)$_3$NH-CO-CH$_2$-CH(CH$_2$-naphthyl)-CO-Leu-NH-CH(iBu)-CH(OH)-thiazole) | $2.1 \times 10^{-7}$ |
| (CH$_3$-N-piperazine-CO-CH$_2$-CH(CH$_2$-naphthyl)-CO-Leu-NH-CH(iBu)-CH(OH)-thiazole) | $4.4 \times 10^{-7}$ |
| ((CH$_3$O)$_2$CHCH$_2$NH-CO-CH$_2$-CH(CH$_2$-naphthyl)-CO-Leu-NH-CH(iBu)-CH(OH)-thiazole) | $4.1 \times 10^{-7}$ |
| (morpholine-CO-CH$_2$-CH(CH$_2$-naphthyl)-CO-His-NH-CH(CH$_2$-cyclohexyl)-CH(OH)-pyridyl) | $2.6 \times 10^{-7}$ |

TABLE I-continued

| Structure | Renin Inhibition IC$_{50}$ (M) |
|---|---|
| [structure: tert-butyl ester-CH$_2$-CH(CH$_2$-naphthyl)-C(O)-Leu-NH-CH(CH$_2$-cyclohexyl)-CH(OH)-pyridyl] | $1.6 \times 10^{-7}$ |
| [structure: morpholino-C(O)-CH$_2$-CH(CH$_2$-naphthyl)-C(O)-Leu-NH-CH(CH$_2$-cyclohexyl)-CH(OH)-pyridyl] | $7.7 \times 10^{-8}$ |
| [structure: HOOC-CH$_2$-CH(CH$_2$-naphthyl)-C(O)-Leu-NH-CH(iPr)-CH(OH)-thiazolyl] | $5.5 \times 10^{-7}$ |
| [structure: morpholino-N(CH$_2$)$_2$NH-C(O)-CH$_2$-CH(CH$_2$-naphthyl)-C(O)-Leu-NH-CH(iPr)-CH(OH)-thiazolyl] | $4.0 \times 10^{-7}$ |
| [structure: morpholino-N(CH$_2$)$_3$NH-C(O)-CH$_2$-CH(CH$_2$-naphthyl)-C(O)-Leu-NH-CH(iPr)-CH(OH)-thiazolyl] | $4.4 \times 10^{-7}$ |

TABLE I-continued

| Structure | Renin Inhibiton IC$_{50}$ (M) |
| --- | --- |
| (pyrrole-N-CH$_3$)-(CH$_2$)$_2$NH-C(O)-CH$_2$-CH(CH$_2$-naphthyl)-C(O)-Leu-NH-CH(iBu)-CH(OH)-(thiazole) | $3.3 \times 10^{-8}$ |
| (pyridin-3-yl)-CH$_2$NH-C(O)-CH$_2$-CH(CH$_2$-naphthyl)-C(O)-Leu-NH-CH(iBu)-CH(OH)-(thiazole) | $1.7 \times 10^{-7}$ |
| (pyridin-2-yl)-CH$_2$NH-C(O)-CH$_2$-CH(CH$_2$-naphthyl)-C(O)-Leu-NH-CH(iBu)-CH(OH)-(thiazole) | $1.2 \times 10^{-7}$ |
| (2-oxopyrrolidin-1-yl)-(CH$_2$)$_3$NH-C(O)-CH$_2$-CH(CH$_2$-naphthyl)-C(O)-Leu-NH-CH(iBu)-CH(OH)-(thiazole) | $7.4 \times 10^{-8}$ |
| (pyridin-2-yl)-O-(CH$_2$)$_2$NH-C(O)-CH$_2$-CH(CH$_2$-naphthyl)-C(O)-Leu-NH-CH(iBu)-CH(OH)-(thiazole) | $4.4 \times 10^{-8}$ |

TABLE I-continued

| Structure | Renin Inhibition IC$_{50}$ (M) |
|---|---|
| (imidazole-N-(CH$_2$)$_4$NH-C(=O)-CH$_2$-CH(CH$_2$-naphthyl)-C(=O)-Leu-NH-CH(iPr)-CH(OH)-C(=S)-thiazole) | $9.3 \times 10^{-8}$ |
| (HOOC-CH$_2$-CH(CH$_2$-naphthyl)-C(=O)-Leu-NH-CH(CH$_2$-cyclohexyl)-CH(OH)-CH$_2$-pyridyl) | $3.8 \times 10^{-6}$ |
| (2-pyridyl-(CH$_2$)$_2$NH-C(=O)-CH$_2$-CH(CH$_2$-naphthyl)-C(=O)-Leu-NH-CH(iPr)-CH(OH)-C(=S)-thiazole) | $1.1 \times 10^{-7}$ |
| (piperidinyl-N-(CH$_2$)$_2$NH-C(=O)-CH$_2$-CH(CH$_2$-naphthyl)-C(=O)-Leu-NH-CH(iPr)-CH(OH)-C(=S)-thiazole) | $6.5 \times 10^{-7}$ |
| (pyrrolidinyl-N-(CH$_2$)$_2$NH-C(=O)-CH$_2$-CH(CH$_2$-naphthyl)-C(=O)-Leu-NH-CH(iPr)-CH(OH)-C(=S)-thiazole) | $7.4 \times 10^{-7}$ |

TABLE I-continued
| Structure | Renin Inhibiton IC$_{50}$ (M) |
|---|---|
| 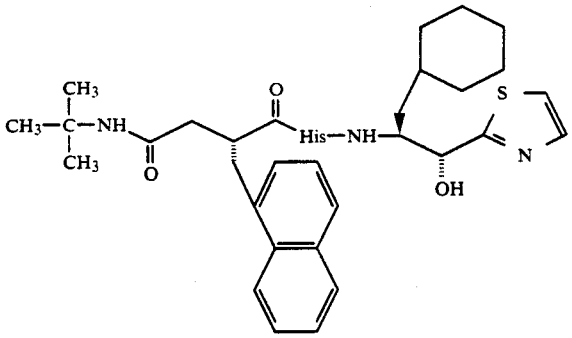 | $7.1 \times 10^{-6}$ |
| 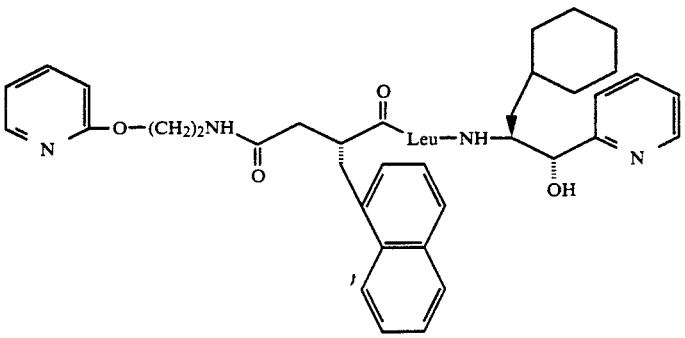 | $1.7 \times 10^{-7}$ |
| 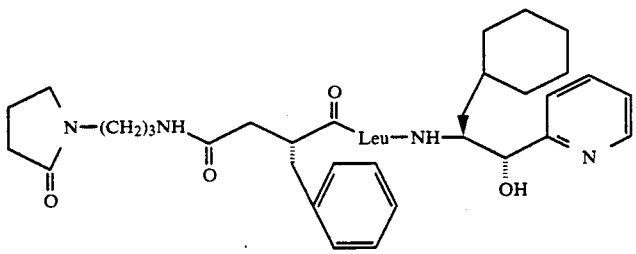 | $1.3 \times 10^{-7}$ |
| 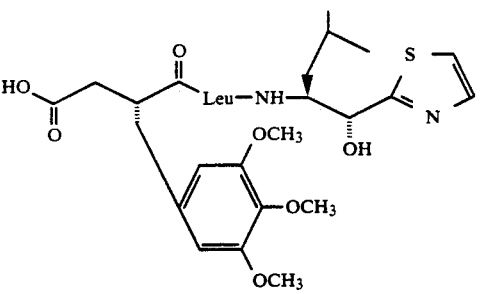 | $6.0 \times 10^{-6}$ |
| 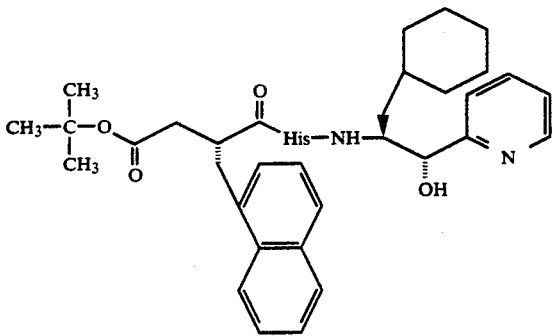 | $4.8 \times 10^{-6}$ |

TABLE I-continued

| Structure | Renin Inhibiton IC$_{50}$ (M) |
|---|---|
| 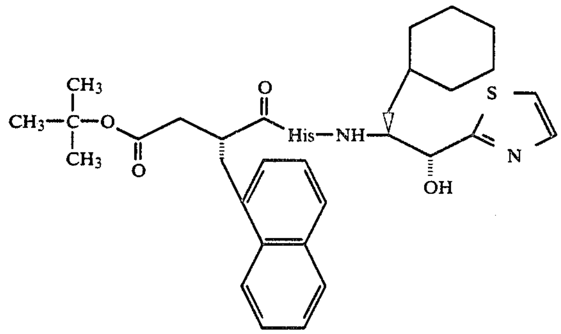 | $3.0 \times 10^{-7}$ |
| 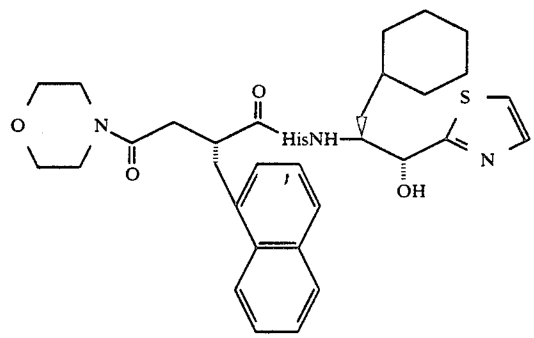 | $3.5 \times 10^{-8}$ |
| 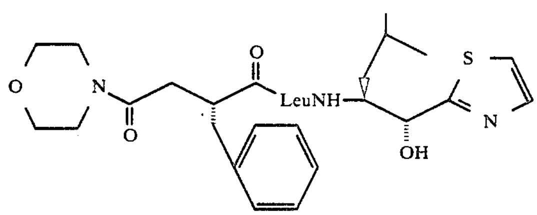 | $4.2 \times 10^{-5}$ |
| 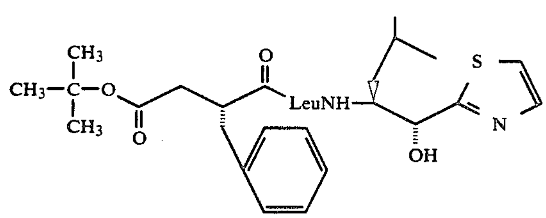 | $6.5 \times 10^{-6}$ |
| 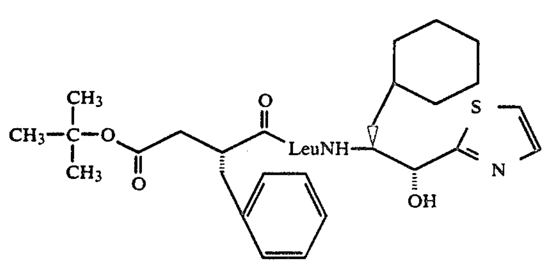 | $1.6 \times 10^{-7}$ |

TABLE I-continued
| Structure | Renin Inhibiton IC$_{50}$ (M) |
|---|---|
| 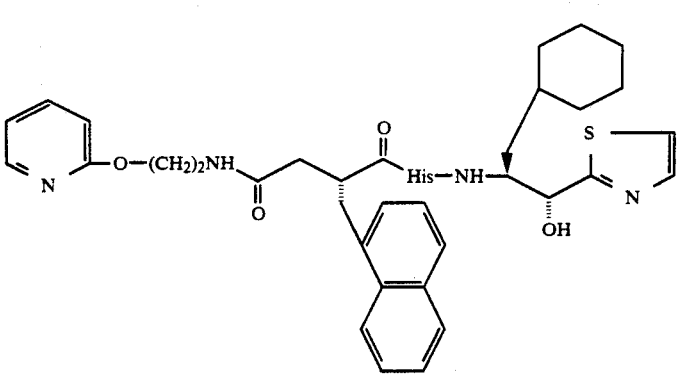 | $5.8 \times 10^{-7}$ |
| 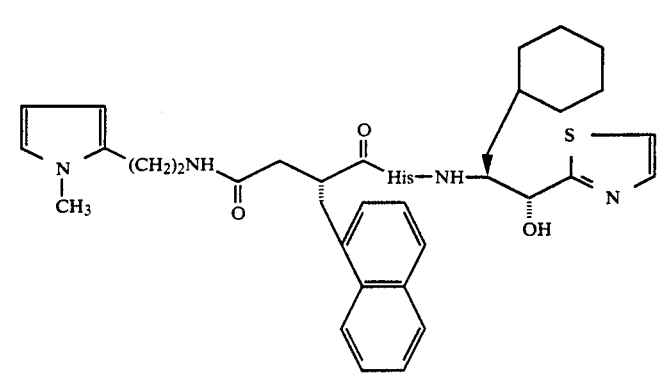 | $3.4 \times 10^{-7}$ |
| 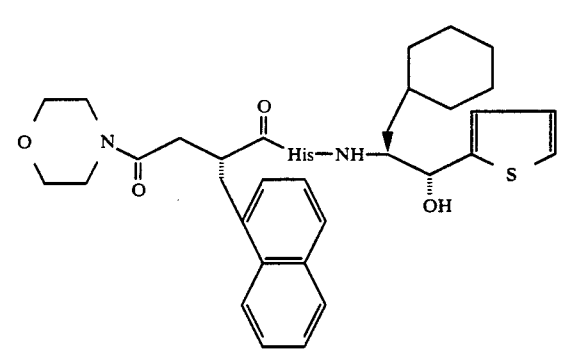 | $2.7 \times 10^{-7}$ |
| 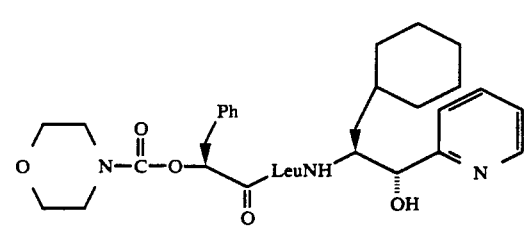 | $7.7 \times 10^{-7}$ |
| 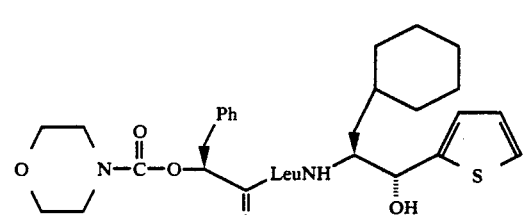 | $2.7 \times 10^{-7}$ |

TABLE I-continued

| Structure | Renin Inhibiton IC$_{50}$ (M) |
|---|---|
| 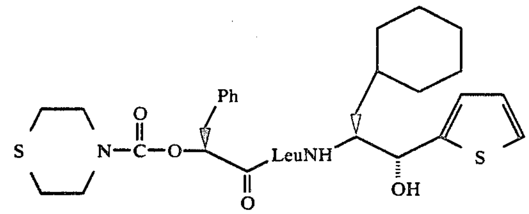 | $5.0 \times 10^{-7}$ |
| 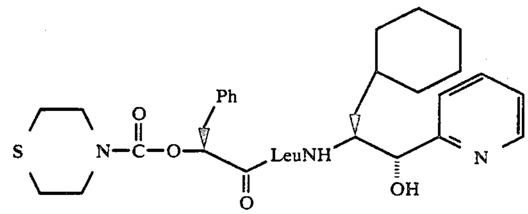 | $8.4 \times 10^{-7}$ |
| 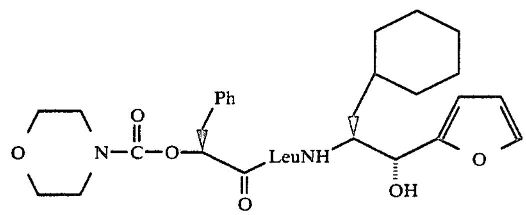 | $1.0 \times 10^{-7}$ |
| 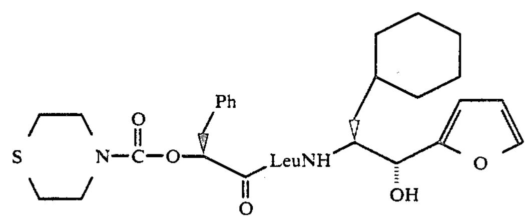 | $4.7 \times 10^{-8}$ |
| 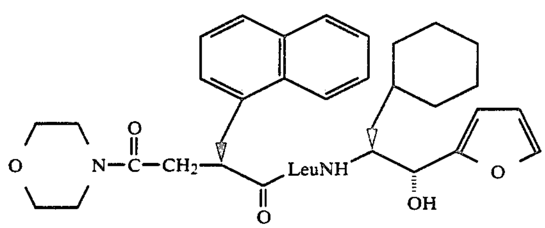 | $8.8 \times 10^{-9}$ |
| 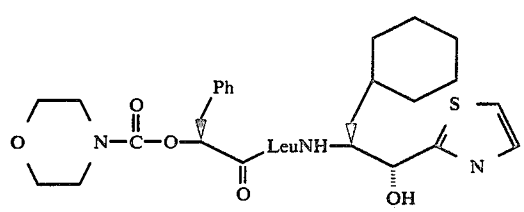 | $1.1 \times 10^{-8}$ |
| 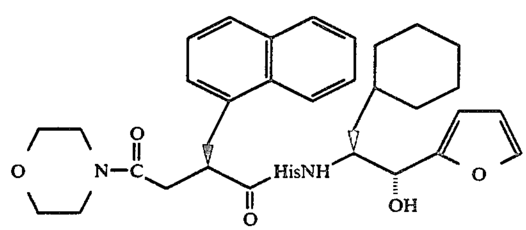 | $4.9 \times 10^{-9}$ |

TABLE I-continued

| Structure | Renin Inhibiton IC$_{50}$ (M) |
|---|---|
| [structure: CH$_3$C(O)-N-piperazine-N-C(O)-O-CH(Ph)-C(O)-LeuNH-CH(CH$_2$Cy)-CH(OH)-furan] | $4.2 \times 10^{-8}$ |
| [structure: CH$_3$OCH$_2$CH$_2$-NH-C(O)-O-CH(Ph)-C(O)-LeuNH-CH(CH$_2$Cy)-CH(OH)-furan] | $1.7 \times 10^{-6}$ |
| [structure: dioxaspiro-piperidine-N-C(O)-O-CH(Ph)-C(O)-LeuNH-CH(CH$_2$Cy)-CH(OH)-furan] | $2.1 \times 10^{-7}$ |
| [structure: morpholine-N-C(O)-O-CH(Cy)-C(O)-LeuNH-CH(CH$_2$Cy)-CH(OH)-furan] | $1.8 \times 10^{-7}$ |
| [structure: oxo-piperazine-N-C(O)-O-CH(Ph)-C(O)-LeuNH-CH(CH$_2$Cy)-CH(OH)-furan] | $1.9 \times 10^{-10}$ |
| [structure: 4-oxo-piperidine-N-C(O)-O-CH(Ph)-C(O)-LeuNH-CH(CH$_2$Cy)-CH(OH)-furan] | $5.8 \times 10^{-8}$ |

The novel compounds of the present invention have been found to be highly useful for lowering elevated blood pressure in mammals when administered in amounts ranging from about 5 mg to about 50 mg/kg of body weight per day.

The compounds of this invention are preferably administered by a parenteral route such as intravenous, intramuscular or subcutaneous, but may be administered orally if desired.

Compositions, according to the present invention, having the desired clarity, stability and adaptability for parenteral use are obtained by dissolving from 0.10% to 10% by weight of active compound in a vehicle consisting of a polyhydric aliphatic alcohol or mixtures of such alcohols. Especially satisfactory are glycerin, propylene glycol and polyethylene glycols. Although various mixtures of polyethylene glycols may be used, it is preferred to use a mixture having an average molecular weight of from about 200 to about 400.

In addition to the active compound, the parenteral solutions may also contain various preservatives to prevent bacterial and fungal contamination as well antioxidants to promote stability.

For intramuscular injection, the preferred concentration of active compound is 0.25 to 0.50 mg/ml of the finished compositions.

The novel compounds of this invention are equally adapted to intravenous administration when diluted with water or diluents employed in intravenous therapy such as isotonic glucose. For intravenous use, initial concentrations down to about 0.05 to 0.2 mg/ml of active compound are satisfactory.

The following specific reference examples illustrate the preparation of intermediate compounds useful in our invention.

REFERENCE EXAMPLE 1

N-[N-(tert-Butoxycarbonyl)-N-methyl-L-leucyl]-(S)2-amino-4-methyl-1-(2-thiazolyl)pentan-1-ol To a mixture of 0.26 g of N-(tert-butoxycarbonyl)-N-methyl-L-leucine in 2 ml of dichloromethane was added 0.15 ml of triethylamine and 0.47 g of benzotriazol-1-yloxytris(dimethylamino)phosphonium hexafluorophosphate (BOP-reagent). After one minute, 0.20 g of (S)2-amino-4-methyl-(R)1-(2-thiazolyl)pentan-1-ol was added and the mixture was stirred at room temperature overnight. The mixture was refluxed for 15 minutes, diluted with 20 ml of ethyl acetate and washed (twice) with 5 ml each of 1N hydrochloric acid, and 1M sodium bicarbonate. The organic layer was filtered through a thin pad of hydrous magnesium silicate and the pad washed with ethyl acetate. The filtrate concentrated to give 0.41 g of gum; $[\alpha]_D^{26}$ $-68°\pm3$ (c, 0.315, methanol).

REFERENCE EXAMPLE 2

N-[N-Methyl-L-leucyl]-(S)2-amino-4-methyl-(R)1-(2-thiazolyl)pentan-1-ol

To 0.41 g of N-[N-(tert-butoxycarbonyl)-N-methyl-L-leucyl]-(S)2-amino-4-methyl-(R)1-(2-thiazol-yl)pentan-1-ol was added 4 ml of anhydrous 2N hydrochloric acid in ethyl acetate. The mixture was stirred for 2 hours and the solvent removed under vacuum. The residue was dissolved in water and concentrated ammonium hydroxide added. The solid formed, was filtered and then washed with cold water to give 0.095 g of crystals, mp 66°-67° C.; Rf 0.05 on silica gel plate with ethyl acetate-methanol (9:1) as solvent. The sample was distilled (onto cold finger) under vacuum to give crystals, mp 86°-87° C.; $[\alpha]_D^{26}$ $-41°\pm1$ (c, 0.943, methanol).

REFERENCE EXAMPLE 3

N-(L-leucyl)-(S)2-amino-4-methyl-(R)1-(2-thiazolyl)-pentan-1-ol

To a solution of 1.76 g of imidazole in 15 ml of dichloromethane under nitrogen was added 1.1 g of phenyl dichlorophosphate (phenyl phosphorodichloridate) in 5 ml of dichloromethane and the solution cooled to 0° C. A solution of 1.25 g of $N^\alpha$-tert-butoxycarbonyl-L-leucine hydrate in 6 ml of dichloromethane was dried over magnesium sulfate and filtered. The filtrate was added to the first solution and the mixture stirred one hour at 0° C. To this mixture was added 1.05 g of (S)2-amino-4-methyl-(R)1-(2-thiazolyl)pentan-1-ol. After stirring at room temperature overnight the mixture was refluxed one hour and filtered. The filtrate was washed with 10 ml each of 2N hydrochloric acid, 1M sodium bicarbonate and dried over magnesium sulfate. The filtrate was passed through a thin pad of hydrous magnesium silicate and the pad washed with dichloromethane. The filtrate was concentrated under vacuum to give 1.71 g of N-[N-(tert-butoxycarbonyl (S)2-amino-4-methyl-(R)1-(2-thiazolyl)pentan-1-ol as an oil; Rf 0.43 on silica gel plate with ethyl acetate-hexane (1:1) as solvent.

To the preceding oil (1.71 g) in one ml of ethyl acetate was added 16 ml of anhydrous 2N hydrochloric acid in ethyl acetate. After stirring 3 hours at room temperature, one ml of hexane was added and the mixture cooled and filtered to give 1.4 g of the product as the hydrochloride, mp 136°-140° C. The hydrochloride was dissolved in water (4 ml) and ammonium hydroxide (2 ml) added. Cooling gave crystals which were filtered and washed with cold water to give 0.97 g of product as crystals, mp 112°-116° C. Recrystallization from diisopropyl ether gave 0.67 g of crystals, mp 112°-114° C.; $[\alpha]_D^{26}$ $-34°\pm1$ (c, 0.976, methanol).

REFERENCE EXAMPLE 4

(R)-Dihydro(phenylmethyl)-2,5-furandione

To 17.2 g of (R)-(phenylmethyl)butanedioic acid was added 34 ml of acetic anhydride. The mixture was stirred and warmed at 80° C. until the solid dissolved (approximately 5 minutes). The mixture was cooled and diluted with 78 ml of diisopropyl ether and the chilled mixture filtered to give 11.4 g of crystals, mp 124°-125° C.; $[\alpha]_D^{26}$ $-54°\pm1$ (c, 1.05, ethyl acetate

REFERENCE EXAMPLE 5

±N-(tert-Butoxycarbonyl)-3-(2-thienyl)alanine

To a stirred mixture of 1.7 g of 3-(2-thienyl)-D,L-anine in 20 ml of dioxane was added 10 ml of water. The mixture was cooled (ice-water bath)and 2.4 g of 2-tert-butoxycarbonyloxyimino)-2-phenylacetonitrile (BOC-ON) was added. After stirring for 0.5 hours, the mixture was concentrated to 15 ml and acidified to pH 2 to 3 with 0.35M potassium hydrogen sulfate. The crystals which separated were filtered, washed with cold water and air dried to give 2.2 g of crystals, mp 113°-114° C.

REFERENCE EXAMPLE 6

(R)-qamma-Oxo-alpha(phenylmethyl)-4-moroholinebutyric acid

To a cooled solution of 3.6 ml of dry morpholine in 10 ml of dry tetrahydrofuran under argon was added 3.8 g of (R)-dihydro(phenylmethyl)-2,5-furandione (exothermic). The solution was stirred for 1.5 hours at room temperature and the solvent removed under vacuum. The residue was stirred with 21 ml of 1N hydrochloric acid and extracted with ethyl acetate. The extract was dried over magnesium sulfate and the solvent removed to give 4.0 g of thick oil. A sample (ca 2.0 g) from a similar run using 1.9 g of (R)-dihydro(phenylmethyl)-2,5-furandione was chromatographed on a Waters-prep 500 HPLC apparatus on silica gel with ethyl acetate containing 1% of formic acid. The fractions #3 and #4 were concentrated under vacuum and dissolved in diisopropyl ether. On standing there was obtained 0.12 g of crystals, mp 106°-107°C.; $[\alpha]_D^{26}$ $+97°\pm1$ (c, 1.00, methanol).

REFERENCE EXAMPLE 7

2-(Phenylmethyl)butanedioic acid,
4-(1,1-dimethylethyl)ester

A mixture of 1.9 g of (R)-dihydro(phenylmethyl)-2,5-furandione, 10 ml of dry tert-butanol and 0.12 g of 4-dimethylaminopyridine was heated on a steam bath for 16 hours. The mixture was concentrated to dryness and the residue dried in oven. Ether was added and a small amount of solid filtered off. The filtrate was concentrated to give 2.1 g of oil. The oil was chromatographed on silica gel with a Waters-prep 500 HPLC apparatus with ethyl acetate-hexane (3:17) containing 1% formic acid as solvent. Solids from cuts 2-6 were combined and crystallized from isopropanol-hexane to give 0.77 g of product, mp 93°-94° C.; $[\alpha]_D^{26}$ 0° (c, 1.06, methanol).

REFERENCE EXAMPLE 8

N-(L-leucyl)-(S)2-amino-3-cyclohexyl(R)1-(2-pyridinyl)propan-1-ol

A solution of 0.75 g of $N^\alpha$-tert-butoxycarbonyl-L-leucine monohydrate in dichloromethane was stirred with anhydrous magnesium sulfate for 2 hours, filtered and the filtrate concentrated to a volume of 15 ml. This solution was chilled to 0° C. and 0.488 g of N,N-carbonyldiimidazole added. The solution was stirred at 0° C. for one hour and 0.469 g of (S)2-amino-3-cyclohexyl-(R)1-(2-pyridinyl)propan-1-ol added. The mixture was stirred at room temperature overnight, washed twice with saturated sodium bicarbonate, water, brine and dried (MgSO$_4$). The solvent was removed under reduced pressure to give 1.0 g of a white foam. This foam was dissolved in chloroform-methanol (99:1) and the combined filtrates concentrated under vacuum to give 0.90 g of N-[N-(tert-butoxycarbony)-L-leucyl](S)2-amino-3-cyclohexyl(R)1-(2-pyridinyl)propan-1-ol as a clear foam.

To a 0.30 g sample of the preceding compound in 5 ml of dichloromethane was added 0.516 ml of trifluoroacetic acid and the mixture stirred overnight. The solution was poured into ice-cold sodium hydroxide (1.61 ml of 5N sodium hydroxide in 5 ml of water), stirred and the organic layer separated. The aqueous layer was extracted twice with dichloromethane and the organic layer and extracts combined and dried(MgSO$_4$). The solvent was removed under vacuum. The residue was crystallized from diisopropylether and recrystallized from diisopropylether to give 0.102 g of white crystals, mp 98°-100° C.

REFERENCE EXAMPLE 9

(S,R)-gamma-Oxo-aloha(3,4,5-trimethoxyphenylmethyl)-4-moroholinebutyric acid

To a stirred mixture of 17.4 g of diethyl succinate, 19.6 g of 3,4,5-trimethoxybenzaldehyde in 175 ml of ethanol chilled to 0° C. under argon was added 5.0 g of sodium hydride (60% in oil) in three equal portions. The solution was then refluxed for 30 minutes and 125 ml of 2N sodium hydroxide added. The solution was refluxed for 2 hours and concentrated under vacuum. The residue was diluted with water, extracted with ether and the aqueous layer acidified with concentrated hydrochloric acid. The mixture was extracted three times with 45 ml of ether and the ether extracts washed with saturated sodium chloride solution. The ether layer was dried (MgSO$_4$) and the solvent removed under vacuum to give 24.82 g of [(3,4,5-trimethoxyphenyl)methylene]butanedioic acid as a yellow oil.

A mixture of 5.0 g of the preceding compound and 30 ml of acetic anhydride was heated on a steam bath until a solution was obtained and then the solution was heated at 60° C. for one hour. The mixture was concentrated under vacuum to give 5.0 g of an oil. The oil was crystallized from a mixture of 12 ml of ether and 6 ml of ethyl acetate to give 2.13 g of dihydro-3-[(3,4,5-trimethoxyphenyl)methylene]-2,5-furandione as yellow crystals, mp 184°-187° C.

The preceding compound (7.56 g) in 34 ml of dichloromethane was added to a solution of 4.71 g of morpholine in 200 ml of dichloromethane. The solution was stirred at room temperature for 2 hours and the solvent removed under vacuum to give a yellow oil. To this oil was added 35 ml of 1N hydrochloric acid and the mixture extracted with three 40 ml portions of ethyl acetate. The extract was dried (MgSO$_4$) and the solvent removed. The residue was crystallized from ethyl acetate-hexane (1:1) to give 8.6 g of gamma-oxo-alpha-[(3,4,5-trimethoxyphenyl)methylene]-4-morpholinebutanoic acid as crystals, mp 135°-138° C.

The preceding compound (7.46 g) in 150 ml of methanol was added to a mixture of 50 ml of methanol and 0.5 g of 10% palladium on carbon and the mixture hydrogenated in a Parr hydrogenator at 51 psi. The catalyst was filtered off (argon atmosphere) and the solvent removed under vacuum to give 7.14 g of gamma-oxo-alpha-[(3,4,5-trimethoxyphenyl)methyl]-4-morpholinebutanoic acid as a glass; Anal Calcd: C, 58.8; H, 6.9; N, 3.8. Found: C, 58.2; H, 6.7; N, 3.5.

REFERENCE EXAMPLE 10

N-(L-Leucyl)-(S)2-amino-3-cyclohexyl-(R)1-(2-thiazolyl)propan-1-ol

A sample of 0.26 g of $N^\alpha$-tert-butoxycarbonyl-L-leucine monohydrate was dried with magnesium sulfate in 2 ml of dichloromethane. The mixture was filtered and 0.15 ml of dry triethylamine and 0.47 g of benzotriazol-1-yloxytris(dimethylamino)phosphonium hexafluorophosphate (BOP) added. After one minute, 0.24 g of (S)2-amino-3-cyclohexyl-(R)1-(2-thiazolyl)propan-1-ol was added and the mixture stirred overnight and refluxed 2 hours. The mixture was concentrated and the residue in ethyl acetate was washed with 1N hydrochloric acid, sodium carbonate solution and brine. The organic layer was dried (MgSO$_4$) and concentrated to give 0.44 g of crude N-[N-(tert-butoxycarbonyl)-L-leucyl]-(S)2-amino-3-cyclohexyl-(R)1-(2-thiazolyl)propan-1-ol as a glass.

The preceding compound was added to 5 ml of 2N anhydrous hydrochloric acid in ethyl acetate and the mixture stirred for 2 hours. The mixture (containing solid) was diluted with 5 ml of hexane, filtered and the solid washed with hexane. The solid was dissolved in 1 ml of water and 0.7 ml of concentrated ammonium hydroxide added. The solid which separated was filtered, and dried to give 0.27 g of solid, mp 140°-141° C.

REFERENCE EXAMPLE 11

N-(L-Histidyl)-(S)2-amino-4-methyl-(R)1-(2-thiazolyl)-pentan-1-ol

To a suspension of 2.4 g of $N^\alpha$-tert-butoxycarbonyl-L-histidine in 24 ml of dichloromethane was added 1.3 ml of triethylamine and then 4.2 g of benzotriazol-1-yloxytris(dimethylamino)phosphonium hexafluorophosphate (BOP). After stirring at room temperature for 2 minutes, 1.73 g of (S)2-amino-4-methyl-(R1-(2-thiazolyl)pentan-1-ol was added. The mixture was stirred for 4 days and refluxed for one hour and the solvent removed under vacuum to give an oil. This oil in 20 ml of ethyl acetate was washed with 10 ml each of water and 1M sodium bicarbonate. The organic layer was washed with 5 ml of 2N citric acid, 20 ml of 1M sodium bicarbonate, brine and dried (MgSO$_4$). The solvent was removed under vacuum to give 2.7 g of N-[N-(tert-butoxycarbonyl)-L-histidyl]-(S)2-amino-4-methyl-(R)1-(2-thiazolyl)pentan-1-ol as a foam.

The preceding compound (2.7 g) was dissolved in 5 ml of ethyl acetate under argon and 30 ml of 2N anhydrous hydrochloric acid in ethyl acetate was added by way of a syringe. After stirring for 2 hours crystals had separated and the mixture was diluted with 35 ml of hexane. The mixture was filtered to give 4.5 g of solid. This solid was dissolved in 9 ml of water and made basic with 3 ml of concentrated ammonium hydroxide. The mixture was extracted with ethyl acetate and the extract dried (MgSO$_4$). The solvent was removed under vacuum to give 1.23 g of solid (foam). A sample on standing crystallized to give crystals, mp 118°–126° C.

REFERENCE EXAMPLE 12

(R)-alpha-2-(1,1-Dimethylethyl)amino1-2-oxoethyl]-benzenepropionic acid

To a solution of 6.0 g of tert-butylamine in 20 ml of tetrahydrofuran cooled to 0° C. under argon was added, in 5 equal portions, 7.6 g of (R)-dihydro (phenylmethyl)-2,5-furandione. After the second, third and fourth additions, an additional 30 ml of tetrahydrofuran was added. The mixture(containing crystals) was stirred overnight at room temperature and filtered. The filtrate was concentrated under vacuum to an oil. The crystals and the oil were combined and 42 ml of cold 1N hydrochloric acid added. The mixture was extracted three times with 40 ml of ethyl acetate and the combined extracts dried (MgSO$_4$) and concentrated to give 15.03 g of an oil. The oil was dissolved in 12 ml of isopropyl acetate plus diisopropyl ether and chilled to give 4.67 g of crystals, mp 110°–112° C. Recrystallization from a mixture of 10 ml of isopropyl acetate and 5 ml of diisopropyl ether gave 4.06 g of crystals, mp 110°–112° C.; $[\alpha]_D^{26}+12°\pm1$ (c, 1.01, methanol).

REFERENCE EXAMPLE 13

Dihydro-3-(1-naphthalenylmethylene)-2,5-furandione

A mixture of 38 g of (1-naphthalenylmethylene)-butanedioic acid and 270 ml of acetic anhydride was heated at 60° C. for one hour. The mixture was evaporated under reduced pressure to give 41.96 g of an oil. The oil was crystallized from 220 ml of toluene-hexane (1:1) to give 24.94 g of crystals, mp 162°–164° C.

REFERENCE EXAMPLE 14

2-(1-Naphthalenylmethyl)-3-(tert-butylaminocarbonyl)-propionic acid

To a mixture of 4.7 g of tert-butylamine in 248 m of dichloromethane cooled to 0° C. under argon was added 8.0 g of dihydro-3-(1-naphthalenylmethylene)-2,5-furandione in three equal portions. The mixture was stirred for 2 hours at 0° C. and the solvent removed under reduced pressure to give 18.4 g of an oil. To this oil was added 34 ml of 1N hydrochloric acid and 34 ml of ethyl acetate. The solid which separated was filtered off to give 4.23 g of white crystals, mp 188°–190° C. The organic layer was separated and the aqueous layer extracted three times with 34 ml of ethyl acetate. The organic layer and extracts were combined, dried (MgSO$_4$) and the solvent removed. The residue was triturated with ethyl acetate-toluene-hexane (1:1:1) to give 1.82 g of crystals, mp 188°–190° C.

A 2.0 g sample of the preceding compound in 50 ml of methanol containing 0.2 g of 10% palladium on carbon was hydrogenated under 50 lb pressure in a Parr hydrogenator. The mixture was filtered through a pad of diatomaceous earth and the filtrate concentrated under reduced pressure to give the product as a solid.

REFERENCE EXAMPLE 15

N-(L-Histidyl)-(S)2-amino-3-cyclohexyl-(R)1-(2-thiazolyl)propan-1-ol

To a suspension of 0.59 g of N$^\alpha$-tert-butoxycarbonyl-L-histidine in 6 ml of dichloromethane was added 0.32 ml of triethylamine and 1.02 g of benzotriazol-1-yloxy-tris(dimethylamino)phosphonium hexafluorophosphate (BOP). After stirring for one minute, 0.53 g of (S)2-amino-3-cyclohexyl-(R)1-(2-thiazolyl)propan-1-ol was added and the mixture was stirred at room temperature overnight. The mixture was concentrated under vacuum to give an oil. This oil in 20 ml of ethyl acetate was washed once with 5 ml of water, three times with 5 ml portions of 1M sodium bicarbonate and with 5 ml of brine. The organic layer was dried (MgSO$_4$) and filtered through 8.0 g of hydrous magnesium silicate. The hydrous magnesium silicate was washed with three 150 ml portions of ethyl acetate. The filtrate and ethyl acetate washes were combined and the solvent removed to give 1.0 g of solid. This solid was dissolved in dichloromethane and the solution filtered through diatomaceous earth. The filtrate was evaporated under reduced pressure to give 0.98 g of N-[N$^\alpha$-(tert-butoxycarbonyl)-L-histidyl]-(S)2-amino-3-cyclohexyl-(R)1-(2-thiazolyl)-propan-1-ol as a hard glass. The preceding compound (0.98 g) in one ml of ethyl acetate was treated with 10 ml of 2N anhydrous hydrochloric acid in ethyl acetate. After stirring for 2 hours 10 ml of hexane was added and the mixture filtered to give crystals. The crystals were dissolved in 3 ml of water and 0.4 ml of 15N ammonium hydroxide added. The mixture was extracted with ethyl acetate and the extract dried (MgSO$_4$). The solvent was removed to give 0.40 g of solid.

REFERENCE EXAMPLE 16

(S)2-Amino-3-cyclohexyl((R)1-(2-pyridinyl)propan-1-ol

To a solution of 3.16 g of 2-bromopyridine in 20 ml of dry tetrahydrofuran cooled to −78° C. under argon was added 11.6 ml of 2.0M n-butyllithium in tetrahydrofuran. After 5 minutes, 3.14 g of N-methoxy-N-methyl-N$^\alpha$-tertbutoxycarbonyl-L-cyclohexylalaninamide in 20 ml of dry tetrahydrofuran was added. The dark solution was stirred at −78° C. for one hour. To the mixture was added 20 ml of saturated aqueous sodium sulfate solution. After warming to room temperature the mixture was poured into 50 ml of water and extracted with ethyl acetate. The organic layer was dried (Na$_2$SO$_4$) and solvent removed. The residue was chromatographed on a silica gel column to give 2.01 g of 1,1-dimethylethyl-(S)[1-(cyclohexylmethyl)-2-oxo-2-(2-pyridinyl)ethyl]-carbamate as an oil; $[\alpha]_D^{26}$ 135o i 1 (c, 0.812, methanol).

The preceding compound (6.49 g) was dissolved in 80 ml of tetrahydrofuran and the solution cooled to −78° C. To this solution was added 40 ml of 1.0M lithium tri-sec-butyl borohydride in tetrahydrofuran over 10 minutes. The mixture was stirred at −78° C. for 3.5 hours and allowed to warm to room temperature. The solution was cooled to −8° C., diluted with 20 ml of water and 20 ml of hydrogen peroxide added dropwise (temperature rose to 45° C.) The mixture was extracted with ethyl acetate, dried (MgSO$_4$) and the solvent removed to give 6.38 g of oil. This oil was chromatographed over silica gel with ethyl acetate-hexane (3:7) to give 3.12 g of (S)2-(tertbutoxycarbonyl)amino-3-cyclohexyl-(R)1-(2-pyridinyl)propan-1-ol an an oil. The oil was crystallized from hexane to give 1.5 g of crystals, mp 68°-69° C.; $[\alpha]_D^{26} +9° \pm 1$ (c, 1.07, methanol).

To a 1.0 g sample of the preceding compound in 2 ml of dichloromethane was added 2 ml of trifluoroacetic acid. After stirring for 6 hours 15 ml of 2N sodium hydroxide was added. The mixture was extracted with three 5 ml portions of dichloromethane, and the combined extracts dried (K$_2$CO$_3$). The solvent was removed to give 0.59 g of oil which was crystallized from diisopropyl ether to give 0.27 g of product as crystals, mp 59°-60° C.

REFERENCE EXAMPLE 17

N-[L-Histidyl]-(S)2-amino-3-cyclohexyl-(R)1-(2-pyridinyl)propan-1-ol

To 0.56 g of N$^\alpha$-tert-butoxycarbonyl-L-histidine in 2 ml of dichloromethane was added 0.30 ml of triethylamine and 0.97 g of benzotriazol-1-yloxytris(dimethylamino)phosphonium hexafluorophosphate. After 2 minutes, 0.47 g of (S)2-amino-3-cyclohexyl-(R)1-(2-pyridinyl)propan-1-ol in one ml of dichloromethane was added. The mixture was stirred overnight and refluxed for 5 minutes. The mixture was concentrated under vacuum and the residue in 10 ml of ethyl acetate washed with water (2 ml), 2M sodium carbonate (6 ml) and with brine (2 ml). The organic layer was dried (Na$_2$SO$_4$) and concentrated. The residue was dissolved in formic acid and the solution extracted with dichloromethane. The aqueous layer was treated with concentrated ammonium hydroxide and the mixture filtered to give 0.8 g of N-[N-(tert-butoxycarbonyl)-L-histidyl](S)2-amino-3-cyclohexyl-(R)1-(2-pyridinyl)propan-1-ol as an amorphous solid.

To the preceding compound (1.03 g) in 2 ml of dichloromethane cooled to 0° C. added 2 ml of trifluoroacetic acid. After 3 hours, 15 ml of 2N sodium hydroxide was added while cooling in an ice bath. The mixture was extracted with three 5 ml portions of dichloromethane. The extract was dried (Na$_2$SO$_4$) and the solvent removed under vacuum to give 0.4 g of solid. This solid was chromatographed on five 20×20×0.2 cm thick layer silica gel plates with dichloromethane-methanol-ammonium hydroxide (9:1.2:0.2) as solvent to give 0.19 g of the product of the Example as an amorphous solid; $[\alpha]_D^{26} +4°$(c,1.00, CH$_3$OH).

A mixture of 0.41 g of N$^\alpha$-tert-butoxycarbonyl-L-histidine and 0.28 g of N,N-carbonyldiimidazole in 2 ml of tetrahydrofuran was stirred one hour and warmed briefly. To the solution was added 0.34 g of (S)2-amino-3-cyclohexyl-(R)1-(2-pyridinyl)propan-1-ol. The mixture was stirred overnight. To the mixture was added a mixture of 28 mg of N$^\alpha$-tert-butoxycarbonyl-L-histidine and 28 mg of N,N-carbonyldiimidazole in 0.2 ml of tetrahydrofuran which had been stirred 2 hours. The mixture was stirred for 2 hours and the solvent removed under vacuum. The residue in 5 ml of ethyl acetate was washed three times with 2 ml portions of 1M sodium carbonate, water and brine. The organic layer was dried (Na$_2$SO$_4$) and the solvent removed to give 0.66 g of foam. This foam was dissolved in 1.3 ml of dichloromethane, cooled to 0° C. and 1.3 ml of trifluoroacetic acid added. The solution was stirred for 2 days and 20 ml of 2N sodium hydroxide added. The mixture was extracted with three 10 ml portions of dichloromethane The extract was concentrated under vacuum to give 0.39 g of solid. The solid was chromatographed on five 20×20×0.2 cm thick layer silica gel plates with dichloromethane-methanol-ammonium hydroxide (9:1.2:0.2) as solvent to give 0.14 g of the product of the Example as an amorphous solid.

REFERENCE EXAMPLE 18

N-[N-$\pi$-(Benzyloxymethyl)-L-histidyl]-(S)2-amino-3-cyclohexyl-(R)1-(2-thiazolyl)-1-(tert-butyl-dimethyl-silyloxy)propane To a suspension of 1.10 g of N$^\alpha$-tert-butoxy-carbonyl-$\pi$-x-(benzyloxymethyl)-L-histidine in 3 ml of dichloromethane was added 0.41 ml of triethylamine. To this solution was added 1.28 g of benzotriazol-1-yloxytris(-dimethylamino)phosphonium hexafluorophosphate. After stirring for 1.5 minutes, 0.87 g of (S)2-amino-3-cyclohexyl-(R)1-(2-thiazolyl)-1-[(tert-butyldimethyl)-silyloxy]propane and 0.5 ml of dichloromethane. The mixture was stirred at room temperature overnight and the solvent removed under vacuum. The residue in 20 ml of ethyl acetate was washed three times each with 1N hydrochloric acid and 1M sodium bicarbonate. The organic layer was dried (Na$_2$SO$_4$) and the solvent removed and the residual solid dried to give 1.68 g of glassy solid.

The preceding solid (1.68 g) in 2 ml of dichloromethane was chilled to 0° C. and 2 ml of trifluoroacetic acid added. The mixture was allowed to warm to room temperature and was stirred overnight. The solvent was removed under reduced pressure and the residual gum dissolved in 10 ml of ethyl acetate. The solution was washed twice with 10 ml of 7.5N ammonium hydroxide and brine. The organic layer was dried (Na$_2$SO$_4$) and the solvent removed to give 1.4 g of product as an amorphous solid.

REFERENCE EXAMPLE 19

(S)4-(1-Methylethyl)-3-(1-oxo-3-phenylpropyl)-2-oxazolidinone

To a solution of 2.5 g of (4S)4-isopropyl-2-oxazolidinone in 60 ml of dry tetrahydrofuran under argon, cooled to −78° C. was added 8 ml n-butyllithium (2.5M in hexane). The suspension was allowed to warm slowly to 0° C. and then cooled to −78° C. (total time 50 minutes). To the well stirred suspension was added dropwise 3.3 ml of 3-phenylpropionyl chloride. The resulting solution was stirred at −78° C. for 2 hours and at 0° C. for 0.5 hour. To the solution was added 20 ml of saturated sodium bicarbonate and mixture concentrated under reduced pressure. The suspension was diluted with 20 ml of water and extracted with 150 ml of ethyl acetate. The extract was washed with brine, dried (Na$_2$SO$_4$) and the solvent removed to give 5.67 g of colorless oil. This oil crystallized on standing and the crystals were triturated with hexane to give 5.0 g of crystals; $[\alpha]_D^{26}$ +71°±1 (c, 1.182, CHCl$_3$).

REFERENCE EXAMPLE 20

1,1-Dimethylethyl (S)4-(1-methylethyl)-gamma,2-dioxo-(R)beta-(phenylmethyl)-3-oxazolidinebutanoate To 0.22 g of N,N-diisopropylamine in 4 ml of tetrahydrofuran chilled to 0° C. under argon was added 0.84 ml of D-butyllithium (2.5M in hexane). After 20 minutes the solution was cooled to −78° C. and a solution of 0.52 g of (S)4-(1-methylethyl)-3-(1-oxo-3-phenylpropyl)-2-oxazolidinone in one ml of tetrahydrofuran was added. The mixture was stirred at −78° C. for 0.5 hour and 0.82 ml of tert-butyl bromoacetate added. The mixture was stirred at −78° C. for 2 hours, −60° C. for one hour and warmed to −15° C. over 3 hours. To the mixture was added 5 ml of 1N hydrochloric acid and 20 ml of ethyl acetate. The organic layer was separated and washed with 10 ml of saturated sodium bicarbonate, brine and dried (Na$_2$SO$_4$). The solvent was removed to give 1.07 g of yellow solid. Washing the solid with hexane gave 0.55 g of white solid; $[\alpha]_D^{26}$+98°±1 (c, 0.941, CHCl$_3$).

REFERENCE EXAMPLE 21

(R)2-(Phenylmethyl)butanedioic acid, 4-(1,1-dimethylethyl)ester

To a solution of 0.10 g of 1,1-dimethylethyl (S)4-(1-methylethyl)-gamma,2-dioxo-(R)beta-(phenylmethyl)-3-oxazolidinebutanoate in 9 ml of tetrahydrofuran and 3 ml of water, cooled to 0° C., was added 0.18 ml of 30% hydrogen peroxide, followed by addition of 23 mg of lithium hydroxide. The suspension was stirred at room temperature for 1.5 hours. To the solution was added, at 0° C., 2 ml of 1N sodium sulfite and the mixture stirred for 15 minutes at room temperature. Saturated sodium bicarbonate was added and the solvent removed under reduced pressure. The residue in 2 ml of water was extracted with two 5 ml portions of dichloromethane. The aqueous solution was acidified with 6N hydrochloric acid and extracted with 15 ml of ethyl acetate. The extract was dried (Na$_2$SO$_4$) and the solvent removed to give 0.080 g of white solid; $[\alpha]_D^{26}$ +8°±1 (c, 1.002, CHCl$_3$).

REFERENCE EXAMPLE 22

N-(L-Histidyl)-(S)2-amino-4-methyl-(R)1-(2-thiazolyl)-pentan-1-ol

A mixture of 3.44 g of N$^\alpha$-tert-butoxycarbonyl-N-imidazole-tosyl-L-histidine, 1.44 g of diethyl cyanophosphate and 1.3 ml of triethylamine in 50 ml of dichloromethane was stirred at 0° C. for one hour. A 1.4 g portion of (S)2-amino-4-methyl-(R)1-(2-thiazolyl)pentan-1-ol was added and stirring was continued at 0° C. for 20 hours then for one hour at room temperature. The mixture was diluted with dichloromethane and washed with 50% saturated sodium bicarbonate. The aqueous phase was separated and extracted with dichloromethane. The organic phase and extract were combined, washed with water and brine, dried and evaporated in vacuo to a gum. This gum was dissolved in 70 ml of methanol and 2.84 g of 1-hydroxybenzotriazole added. The mixture was stirred for 21 hours and the solvent removed in vacuo. The residue was dissolved in ethyl acetate, washed with 1N sodium hydroxide, brine, dried and the solvent removed in vacuo. The residue was chromatographed on a flash silica el column, eluting with 5% methanol in ethyl acetate, to give 1.33 g of N$^\alpha$-tert-butoxycarbonyl-L-histidyl-(1R,2S)-2-amino-4-methyl-1-(2-thiazolyl)pentan-1-ol; $[\alpha]_D^{26}$ −34°±1 (c, 0.848, methanol).

A 1.1 g portion of the above compound was dissolved in a mixture of 5 ml of dichloromethane and 1.9 ml of trifluoroacetic acid and stirred for 16 hours. The solution was treated with 15 ml of 1N sodium hydroxide which was saturated with sodium chloride and extracted with 3×30 ml of dichloromethane. The extracts were combined, dried and evaporated in vacuo. The residue was triturated with ether-hexane, giving L-histidyl-(1R,2S)-2-amino-4-methyl-1-(2-thiazolyl)pentan-1-ol as a solid.

REFERENCE EXAMPLE 23

N-(L-Histidyl)-(S)2-amino-3-cyclohexyl-(R)1-(2-thiazolyl)propan-1-ol

A mixture of 0.45 g of phenyl dichlorophosphate and 0.71 g of imidazole in 10 ml of dichloromethane under argon, was allowed to stand 0.5 hour, then cooled to 0° C. and 0.86 g of N$^\alpha$-tert-butoxycarbonyl-N-im-tosyl-L-histidine was added. The mixture was stirred for 2 hours at 0° C., then a solution of 0.48 g of (S)2-amino- 3-cyclohexyl-(R)1-(2-thiazolyl)propan-1-ol in 2 ml of dichloromethane was added. The mixture was stirred at 0° C. for 17 hours and then at room temperature for one day. A 30 ml portion of dichloromethane was added and the solution washed with 30 ml of 50% saturated sodium bicarbonate. The aqueous layer was separated and extracted with 2×20 ml of dichloromethane. The organic layer and extracts were combined, washed with 30 ml of water and 30 ml of brine, dried and the solvent removed. The residue was washed with 4×10 ml of hexane:ether (4:1) to give 1.34 g of white solid.

To 1.2 g of the above solid in 30 ml of methanol was added 0.77 g of 1-hydroxybenzotriazole. This mixture was stirred for 20 hours, then the solvent was removed in vacuo. The residue was dissolved in 60 ml of ethyl acetate, washed with 3×10 ml of 1N sodium hydroxide and 10 ml of brine, dried and the solvent removed. The residue was flash chromatographed on silica gel, eluting with 5% methanol in ethyl acetate and gave 0.61 g of tert-butoxycarbonyl-L-histidyl-(1R,2S)-2-amino-3-cyclohexyl-1-(2-thiazo-1)propan-1-ol as a white solid; $[\alpha]_D^{26}$−55°±2 (c, 0.46, methanol).

A 0.48 g portion of the above compound in 2 ml of dichloromethane and 0.8 ml of trifluoroacetic acid was stirred for 20 hours, then treated with 15 ml of sodium chloride saturated 1N sodium hydroxide and extracted with 3×30 ml of dichloromethane. The extracts were combined, dried and evaporated. The residue was triturated with ether-hexane, giving 0.35 g of L-histidyl-(1R,2S)-2-amino-3-cyclohexyl-1-(2-thiazolyl)propan-1-ol as a white solid; $[\alpha]_D^{26}$−41°±3 (c, 0.288, methanol).

REFERENCE EXAMPLE 24

(S)2-Amino-4-(methylthio)-(R)1-(2-thiazolyl)-butan-1-ol

To a mixture of 17.6 g of imidazole in 150 ml of dichloromethane was added dropwise 11.0 g of phenyl dichlorophosphate. The mixture was cooled to 0° C. and 12.4 g of N$^\alpha$-tert-butoxycarbonyl-L-methionine in 60 ml of dichloromethane was added at a rate to maintain the temperature of the reaction at 0° C. to 5° C. The mixture was stirred at 0° C. for one hour and 5.1 g of N-methoxy-N-methylamine hydrochloride added. The mixture was stirred overnight at room temperature, filtered and the solid washed with dichloromethane. The filtrate was washed with 100 ml each of 2N citric acid, 1N sodium bicarbonate, saturated sodium chloride and dried (MgSO$_4$) The solvent was removed under reduced pressure to give 11.3 g of colorless oil; $[\alpha]_D^{26}$ −45°±1 (c, 0.989, CH$_3$OH).

The preceding compound (11.3 g) was dissolved in 320 ml of ether under argon and 1.85 g of solid lithium aluminumhydride (LAH) added in small portions (solution becomes warm and refluxes). After 0.5 hour the solution was cooled in an ice bath and 320 ml of 1M potassium hydrogensulfate (KHSO$_4$) added slowly. The organic layer was separated and the aqueous layer extracted three times with 200 ml of ether. The organic layer and extracts were combined and washed with three 100 ml portions of 3N hydrochloric acid, two 100 ml portions of 1M sodium bicarbonate and 50 ml of brine. The organic layer was dried (MgSO$_4$) and the solvent removed under vacuum to give 8.68 g of N$^\alpha$-tert-butoxycarbonyl-L-methioninal as an oil.

To a solution of 6.8 g of the preceding compound in 20 ml of dichloromethane was added 4.7 g of 2-trimethylsilylthiazole in 5 ml of dichloromethane (reaction temperature rose to 42° C.). The mixture was stirred under argon at room temperature overnight. The solution was cooled to 0° C. and 13 ml of a 1.0M solution of tetrabutylammonium fluoride in tetrahydrofuran added dropwise. The mixture was refluxed on a steam bath for 1.5 hours and the solvent removed under vacuum. The residue in 40 ml of ethyl acetate was washed with 25 ml each of 2N citric acid, 1M sodium bicarbonate, brine and dried (MgSO$_4$). The solvent was removed to give 10.4 g of an oil.

To the preceding oil (10.4 g) in 10 ml of ethyl acetate was added 10 equivalents of 2N anhydrous hydrochloric acid in ethyl acetate. After stirring at room temperature for 2 hours, the mixture was cooled to 0° C., diluted with 50 ml of hexane, chilled and filtered. The solid was quickly dissolved in 15 ml of water and 4 ml of concentrated ammonium hydroxide added dropwise. The mixture was extracted three times with dichloromethane and the extract dried (MgSO$_4$) and the solvent removed to give 1.72 g of oil. The mother liquors from the 2N HCl-ethyl acetate treatment were extracted with 1N aqueous hydrochloric acid and the aqueous layer treated with concentrated ammonium hydroxide. The mixture was extracted with dichloromethane to give an additional 0.82 g of oil.

The combined oil (1.72 g plus 0.82 g) was chromatographed on silica gel by HPLC on Water-prep 500 instrument with 5% methanol in ethyl acetate containing 3% N-methylmorpholine as solvent. The fractions containing product were combined and a portion of the oil obtained was sublimed to give 0.159 g of crystals, mp 63°-65° C; $[\alpha_D^{26}$ −29°±1 (c, 1.01, CH$_3$OH).

REFERENCE EXAMPLE 25

N-(L-Leucyl)-(S)2-amino-4-(methylthio)-(R)1-(2-thiazolyl)butan-1-ol

To a sample of 1.6 mmol of N$^\alpha$-)(tert-butoxycarbonyl)-L-leucine in 1.6 ml of dichloromethane (dried over magnesium sulfate) was added 0.22 ml of triethylamine and 0.71 g of benzotriazol-1-yloxytris(dimethylamino)phosphonium hexafluorophosphate. After one minute 0.32 g of (S)2-amino-4-(methylthio)-(R)1-(2-thiazolyl)butan-1-ol was added. The mixture was stirred overnight and the solvent removed under vacuum to give 0.60 g of N-[N-(tert-butoxycarbonyl)-L-leucyl]-(S)2-amino-4-(methylthio)-(R)1-(2-thiazolyl)butan-1-ol as an oil.

To the preceding compound (0.60 g) in 2 ml of ethyl acetate was added 7.5 ml of 2N anhydrous hydrochloric in ethyl acetate. The mixture was stirred at room temperature for 2 hours and 10 ml of hexane added. The mixture was chilled and filtered to give a yellow solid. This solid was dissolved in 2 ml of water and 0.3 ml of concentrated ammonium hydroxide added. The mixture was filtered to give 0.29 g of the product of the Example as crystals, mp 83°-85° C.

REFERENCE EXAMPLE 26

N-(L-Histidyl)-(S)2-amino-4-methyl-(R)1-(2-thiazolyl)-pentan-1-ol

To a suspension of 2.4 g of N$^\alpha$-tert-butoxy-carbonyl-L-histidine in 24 ml of dichloromethane was added 1.3 ml of triethylamine, followed by the addition of 4.2 g of benzotriazol-1-yloxytris(dimethylamino) phosphonium hexafluorophosphate (BOP). The mixture was stirred under argon for 2 minutes and 1.73 g of (S)2-amino-4-methyl-(R)1-(2-thiazolyl)pentan-1-ol added. The mixture was stirred for 4 days and the solvent removed. The residue was dissolved in 20 ml of ethyl acetate and the solution washed with 10 ml of water, three 10 ml portions of 1M sodium bicarbonate, 5 ml of 2N citric acid and 20 ml of 1M sodium bicarbonate. The organic layer was dried (MgSO$_4$) and then filtered through a thin pad of hydrous magnesium silicate (pad washed with ethyl acetate). The filtrate was concentrated under vacuum to give 2.7 g of N-[N-(tert-butoxycarbonyl)-L-histidyl]-(S)2-amino-4-methyl-(R)1-(2-thiazolyl)pentan-1-ol as a foam. This foam (2.7 g) was dissolved in 5 ml of ethyl acetate and to the solution was added 30 ml of 2N anhydrous hydrochloric acid in ethyl acetate. The mixture was stirred for 2 hours (crystals separated) and 35 ml of hexane added. The mixture was filtered to give 4.55 g of N-(L-histidyl)-(S)2-amino-4-methyl-(R)1-(2-thiazolyl)pentan-1-ol, dihydrochloride as white hydroscopic crystals. The crystals were dissolved in 9 ml of water and 3 ml of concentrated ammonium hydroxide added. The mixture was extracted with ethyl acetate, the extract dried (MgSO$_4$) and the solvent removed under vacuum to give 1.23 g of N-(L-histidyl)-(S)2-amino-4-methyl-(R)1-(2-thiazolyl)pentan-1-ol as a foam.

REFERENCE EXAMPLE 27

(S)4-(1-Methylethyl)-3-[3-(1-naphthalenyl)-1-oxopropyl]-2-oxazolidinone

To a solution of (4S)4-isopropyl-2-oxazolidine (10.19 g) in 160 ml of dry tetrahydrofuran cooled to −78° C., was slowly added 41.39 ml of a 2.11 molar solution of n-butyllithium in hexanes. The mixture was stirred at −78° C. for 45 minutes and then a solution of 18.99 g of 3-(1-naphthalenyl)propionyl chloride in 25.0 ml of tetrahydrofuran added over 10 minutes. After 4 hours at −78° C., the mixture was quenched with 100 ml of saturated ammonium chloride solution and diluted with 100 ml of water. The mixture was extracted with dichloromethane and the extract washed with saturated sodium bicarbonate, brine and dried (MgSO$_4$). The solvent was removed under vacuum and the residue chromatographed on silica gel with a Waters-prep 500 HPLC with ethyl acetate-hexanes (1:4) as solvent. Fractions containing product were combined and the solvent removed to give 14.65 g of an oil which crystallized on trituration with ethyl acetate-hexanes (1:6); $[\alpha]_D^{26}+64°$ (c, 1.18, CHCl$_3$).

Following the above procedure the following Reference Examples may be prepared.

TABLE V

| Reference Example | Structure | Physical State | Analytical Results |
|---|---|---|---|
| 28 | 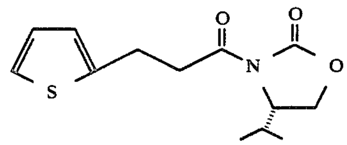 | yellow oil | [alpha]$_D^{26}$ +66° (c, 1.4, CHCl$_3$) |
| 29 | 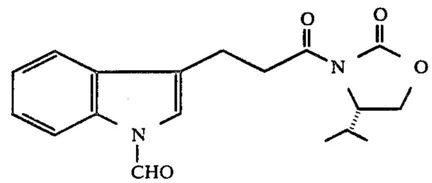 | orange oil | |
| 30 | 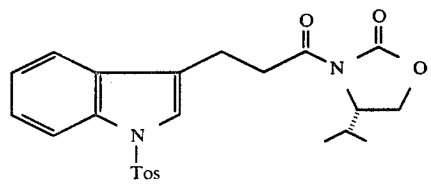 | oil | [alpha]$_D^{26}$ +81° C. (c, 1.08, CHCl$_3$) |
| 31 | 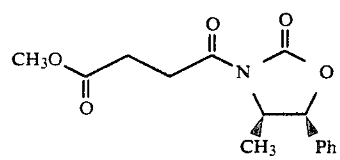 | white oil | [alpha]$_D^{26}$ +26° (c, 0.82, CHCl$_3$) |
| 32 | 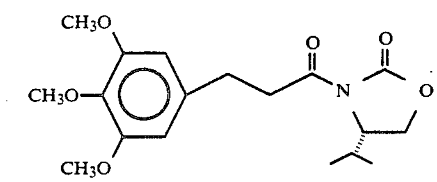 | pale yellow solid | [alpha]$_D^{26}$ +50° ± 1 (c, 1.07, CHCl$_3$) |
| 33 | 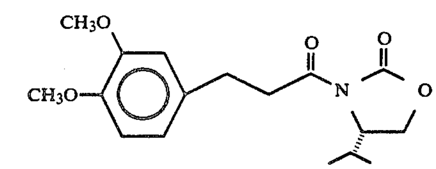 | | |
| 34 | 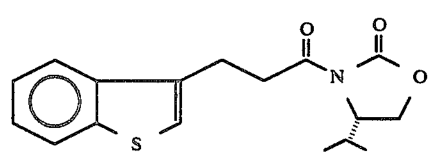 | White solid | [alpha]$_D^{26}$ = +62° (C = 1.00 CHCl$_3$) |
| 35 | 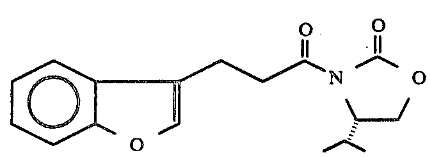 | Pale yellow solid | [alpha]$_D^{26}$ = +60° (C = 1.01 CHCl$_3$) |

TABLE V-continued

| Reference Example | Structure | Physical State | Analytical Results |
|---|---|---|---|
| 36 | CH3O-C6H4-CH2CH2-C(O)-N(oxazolidinone with isopropyl) | | |

REFERENCE EXAMPLE 37

1,1-Dimethylethyl (R)-beta-[[(S)4-(1-methylethyl)-2-oxo-3-oxazolidinyl]-carbonyl]-1-naphthalenebutanoate To a solution of 10.0 g of (S)4-(1-methylethyl)-3-[3-(1-naphthalenyl)-1-oxopropyl]-2-oxazolidinone in 140.0 ml of dry tetrahydrofuran, cooled to −78° C., was slowly added 23.58 ml of a 1.5 molar solution of lithium diisopropylamide mono(tetrahydrofuran) in cyclohexane. The mixture was stirred for 30 minutes at −78° C. and then 15.6 ml of tert-butyl bromoacetate was added dropwise. The mixture was stirred at −78° C. for 30 minutes, at −15° C. for 3 hours and at 0° for one hour. The mixture was quenched with 50 ml of saturated ammonium chloride solution and extracted with dichloromethane. The extract was washed with water, brine, dried (MgSO4) and the solvent removed. The residue was crystallized from hexane to give 7.06 g of white crystals; $[\alpha]_D^{26}+95°$ (c, 1.03, CHCl3).

Following the above procedure, the following Reference Examples may be prepared.

TABLE VI

| Reference Example | Structure | Physical State | Analytical Results |
|---|---|---|---|
| 38 | (tert-butyl ester, thiophene substituent) | white solid | $[alpha]_D^{26}$ +54° (c, 1.08, CHCl3) |
| 39 | (tert-butyl ester, N-CHO indole substituent) | | |
| 40 | (tert-butyl ester, benzothiophene substituent) | Pale yellow solid | $[alpha]_D^{26} = +75°$ (C = 1.03 CHCl3) |
| 41 | (tert-butyl ester, benzofuran substituent) | White solid | $[alpha]_D^{26} = +73°$ (C = 1.02 CHCl3) |

TABLE VI-continued

| Reference Example | Structure | Physical State | Analytical Results |
|---|---|---|---|
| 42 | 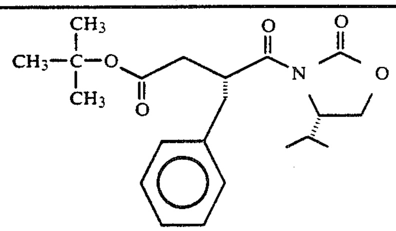 | white solid | $[alpha]_D^{26}$ +98° (c, 0.941, CHCl$_3$) |
| 43 | 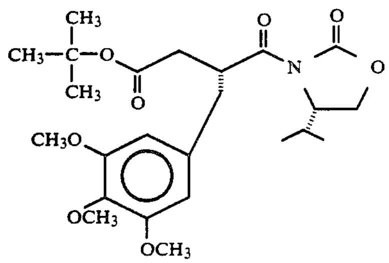 | yellow solid | $[alpha]_D^{26}$ +83° (c, 1.153, CHCl$_3$) |
| 44 | 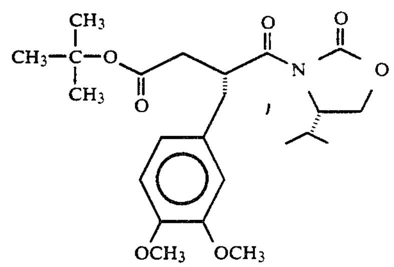 | | |
| 45 | 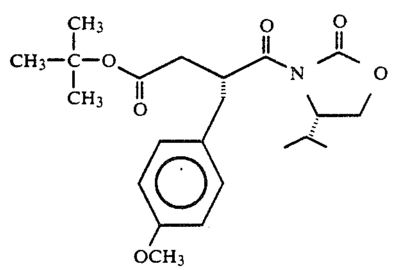 | | |
| 46 | 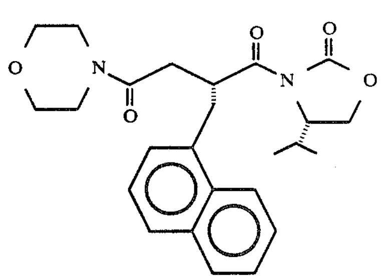 | white crystals | $[alpha]_D^{26}$ +94° (c, 1.05, CHCl$_3$) |

REFERENCE EXAMPLE 47

(S)4-(1-Methylethyl)beta[(R)1-naphthalenylmethyl]-gamma-2-oxo-3-oxazolidinebutanoic acid To a solution of 3.0 g of 1,1-dimethylethyl (R)-beta-[[(S)4-(1-methylethyl)-2-oxo-3-oxazolidinyl]-carbonyl]-1-naphthalenebutanoate in 22.4 ml of dichloromethane, cooled to 0° C., was added 22.4 ml of trifluoroacetic acid. The mixture was allowed to warm to room temperature and was stirred for one hour. The mixture was concentrated under vacuum and to the residue was added 20 ml of saturated sodium bicarbonate. The aqueous layer was acidified with 5% hydrochloric acid and extracted with dichloromethane. The extract was washed with brine, dried (MgSO$_4$) and the solvent removed under vacuum to give a solid; $[\alpha]_D^{26}$+116° (c, 1.06, CHCl$_3$).

REFERENCE EXAMPLE 48

4-[4-(S)4-(1-Methylethyl)-2-oxo-3-oxazolidinyl]-3-(R)1-naphthalenylmethyl)-1,4-dioxobutyl]morpholine To a solution of (S)4-(1-methylethyl)beta-[(R)1-naphthalenylmethyl]-gamma-2-oxo-3-oxazolidine-butanoic acid (7.06 mmol) in 57.3 ml of dichloromethane, cooled to 0° C., was added 0.769 ml (8.83 mmol) of morpholine, 1.47 ml (0.011 mmol) of triethylamine and 1.47 ml (9.69 mmol) of diethyl cyanophosphonate. The mixture was allowed to warm to room temperature and was stirred for 2 hours. The mixture was filtered through a thin pad of hydrous magnesium silicate and the pad washed with chloroform. The filtrate was concentrated under vacuum and the residue triturated with ether to give 2.70 g of white solid; $[\alpha]_D^{26} + 94°$ (c, 1005, CHCl$_3$).

The above procedure may be used to prepare the following compounds.

| $R_1$ | $R_2$ |
|---|---|
| H | H |
| H | lower alkyl(C$_1$-C$_6$) |
| lower alkyl(C$_1$-C$_6$) | lower alkyl(C$_1$-C$_6$) |
| phenyl-(CH$_2$)$_n$— (n = 1-4) | H |
| phenyl-(CH$_2$)$_n$— (n = 1-4) | lower alkyl(C$_1$-C$_6$) |
| 3,4-(CH$_3$O)$_2$-phenyl-(CH$_2$)$_n$— (n = 1-4) | lower alkyl(C$_1$-C$_6$) |
| 3,4,5-(CH$_3$O)$_3$-phenyl-(CH$_2$)$_n$— (n = 1-4) | H |
| H | —CH$_2$CH[O lower alkyl(C$_1$-C$_3$)] |
| imidazolyl-N—(CH$_2$)$_n$— (n = 1-4) | H |
| morpholinyl-N—(CH$_2$)$_n$— (n = 1-4) | H |
| piperidinyl-N—(CH$_2$)$_n$— (n = 1-4) | H |
| 2-oxopyrrolidinyl-N—(CH$_2$)$_n$— (n = 1-4) | H |
| 2-pyridyl-(CH$_2$)$_n$— (n = 1-4) | H |
| 3-pyridyl-(CH$_2$)$_n$— (n = 1-4) | H |
| pyrrolidinyl-N—(CH$_2$)$_n$— (n = 1-4) | H |
| 4-methylpiperazinyl-N—(CH$_2$)$_n$— (n = 1-4) | H |
| (HOCH$_2$)$_2$C(CH$_3$)— | H |
| triazolyl-N—(CH$_2$)$_n$— (n = 1-4) | H |

| $R_1$—N(R$_2$) |
|---|
| pyrrolidinyl-N— |
| piperidinyl-N— |

-continued

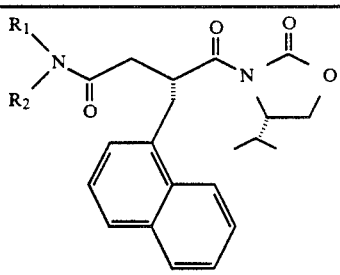

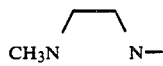

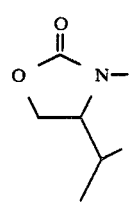

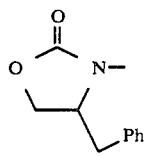

REFERENCE EXAMPLE 49

(R)-(1-naphthalenylmethyl)butanedioic acid, 4-(1,1-dimethylethyl)ester

To a solution of 2.84 g of 1,1-dimethylethyl (R)-beta-[(S)4-[(1-methylethyl)-2-oxo-3-oxazolidinyl]carbonyl]-1-naphthalenebutanonate in 134 ml of tetrahydrofuran-water (3:1), cooled to 0° C., was added 4.5 ml of 30% hydrogen peroxide, followed by 0.563 g of lithium hydroxide monohydrate. The suspension was stirred at 0° C. for 30 minute and at room temperature for one hour. The mixture was cooled to 0° C. and quenched with 29.4 ml of a 1.5 molar aqueous solution of sodium sulfite. The mixture was concentrated under vacuum. The resulting mixture (pH=12) was extracted with dichloromethane. The aqueous layer was acidified with 5% hydrochloric acid and extracted with ethyl acetate. The extract was washed with brine, dried (MgSO4) and the solvent removed under vacuum. The residue was chromatographed on silica gel with a Water-prep 500 HPLC instrument with ethyl acetate-hexane-acetic acid (1:4:0.025) to give 1.99 g of a white solid; $[\alpha]_D^{26} 0°$ (c, 1.0, CHl3).

The preceding compound was further characterized by reaction with diazomethane to give (R)-(1-naphthalenylmethyl)butanedioic acid, 4-(1,1-dimethylethyl)-1-methyl ester as a colorless oil; $[\alpha]_D^{26} +13°$ (c,1.0, CHCl3).

Following the above procedure, the following Reference Examples were prepared.

TABLE VII

| Reference Example | Structure | Physical State | Analytical Results |
|---|---|---|---|
| 50 | 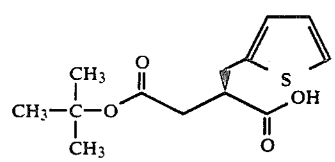 | white solid | $[\text{alpha}]_D^{26}$ −2° (c, 1.07, CHCl3) |
| 51 | 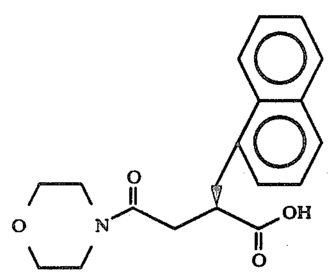 | white solid | $[\text{alpha}]_D^{26}$ −39° (c, 1.04, CHCl3) |
| 52 | 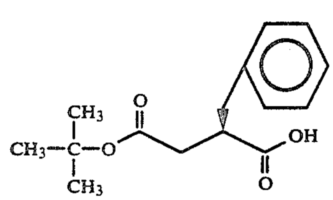 | white solid | $[\text{alpha}]_D^{26}$ +8° (c, 1.00, CHCl3) |

TABLE VII-continued

| Reference Example | Structure | Physical State | Analytical Results |
|---|---|---|---|
| 53 | 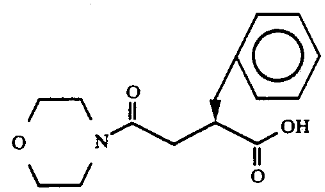 | crystals mp 106–107° C. | $[\alpha]_D^{26}$ +97° (c, 1.00, CH$_3$OH) |

REFERENCE EXAMPLE 54

N-(L-Histidyl)-(S)2-amino-3-cyclohexyl-(R)1-(2-thiazolyl)-1-(tert-butyldimethylsilyloxy)propane To a solution of 25 ml of 3.9 g of imidazole in 25 ml of dichloromethane was added 1.7 ml of phenyl dichlorophosphate. After stirring under nitrogen at room temperature for 20 minutes, the mixture was chilled to 0° C. and 2.94 g of N$^\alpha$-tert-butoxycarbonyl-L-histidine was added. The mixture was stirred at 0° C. for one hour and 3.68 g of (S)2-amino-3-cyclohexyl-(R)1-(2-thiazolyl)-1-(tert-butyldimethylsilyloxy)propane in 5 ml of dichloromethane added. The mixture was stirred at room temperature overnight, filtered and the filtrate concentrated under vacuum. The residue in 50 ml of ethyl acetate was washed (three times) with 10 ml of 2M sodium carbonate, with brine. The aqueous layer was extracted with ethyl acetate. The organic layer and ethyl acetate extracts were combined and the solvent removed to give 7.0 g of a foam (after drying under vacuum). This solid was dissolved in 10 ml of dichloromethane and the solution cooled to 0° C. To the solution was added 10 ml of trifluoroacetic acid. The solution was stirred at room temperature over night and then refluxed for 2 hours. The solution was cooled to 0° C. and added to 130 ml of 2N sodium hydroxide. The mixture was filtered and the organic layer separated. The aqueous layer was extracted with ethyl acetate. The organic layer and extracts were combined and dried (Na$_2$SO$_4$). The solvent was removed under vacuum to give 4.93 g of solid. This solid was chromatographed on silica gel with a Waters-prep 500 HPLC apparatus with dichloromethane-methanoltriethylamine (95:4:1) as solvent. The fractions containing product were combined, the solvent removed and the solid dissolved in ethyl acetate. The solution was washed three times with 5 ml portions of brine, dried (Na$_2$SO$_4$) and filtered through diatomaceous earth. The filtrate was concentrated and the residue dried under vacuum to give 3.92 g of foam: $[\alpha]_D^{26}$ −43°±1 (c, 1.099, CH$_3$OH); FAB mass spectrum −M+H =492.

REFERENCE EXAMPLE 55

(S)2-Amino-3-cyclohexyl-(R)1-(2-furanyl)propan-1-ol

A. 1,1-Dimethylethyl (S)-[1-(cyclohexylmethyl)-2-(2-furanyl)-2-oxoethyl]carbamate A solution of 1.57 g of N-methoxy-N-methyl N$^\alpha$-t-butoxycarbonyl-L-cyclohexylalaninamide in 15 ml of dry tetrahydrofuran was cooled to −78° C. under argon. To the solution was added dropwise 5.9 ml of secondary butyllithium (0.85M in hexane). The viscous mixture was stirred at −78° C. for 1.5 hours and then warmed to 0° C. and stirred for 5 minutes. (Solution A)

A solution of 0.73 ml of furan in 5 ml of dry tetrahydrofuran was cooled to 0° C. and 3.8 ml of n-butyllithium (2.35M in hexane) added. The yellow suspension was stirred at 0° C. for 1.7 hours and then allowed to warm to room temperature for 15 minutes. (yellow solution B)

The yellow solution B was added to solution A and the mixture stirred at 0° C. for 1.5 hours. The mixture was quenched with 5 ml of saturated aqueous ammonium chloride and the solvent tetrahydrofuran removed under vacuum. The residue was diluted with 50 ml of ethyl acetate and 20 ml of 1N hydrochloric acid. The organic phase was separated and washed successively with 20 ml of 1N hydrochloric acid, 20 ml of water, 20 ml of saturated sodium bicarbonate, 20 ml of brine and dried over sodium sulfate. The solvent was removed under vacuum to give 1.63 g of a light brown gum. This gum was dissolved in ether-hexane (1:5 and the solution filtered through a thin pad of hydrous magnesium silicate. The pad was washed with ether-hexane (1:5) and the filtrate concentrated. The residue was triturated with hexane to give 1.23 g of light yellow crystals; $[\alpha]_D^{26}$+41°±1 (c, 1.14, methanol).

B. (S)2-(N-tert-Butoxycarbonyl)amino-3-cyclohexyl-(R,S)1-(2-furanyl)propan-1-ol

A solution of 0.16 g of 1,1-dimethylethyl (S)-[1-(cyclohexylmethyl)-2-(2-furanyl)-2-oxoethyl]carbamate in 2 ml of dry tetrahydrofuran and 0.2 ml of methanol was cooled to 0° C. under argon and 23 mg of sodium borohydride added. The solution was stirred at 0° C. for one hour and quenched with 2 ml of saturated aqueous ammonium chloride The organic solvent was removed under vacuum and the residue diluted with 5 ml of saturated aqueous ammonium chloride. The organic solvent was removed under vacuum and the residue diluted with 5 ml of water and extracted with 10 ml of ethyl acetate. The organic layer was separated, washed successively with 5 ml of 0.5N hydrochloric acid, 5 ml of saturated sodium bicarbonate, 5 ml of brine and dried over sodium sulfate. The solvent was removed under vacuum to give 0.19 g of gummy solid.

C. (4S-trans) 4-(Cyclohexylmethyl)-5-(2-furanyl)-2-oxazolidinone

To a solution of 0.23 g of (S)2-(N-tert-butoxycarbonyl)amino-3-cyclohexyl-(R,S)1-(2-furanyl)propan-1-ol in 3 ml of dichloromethane was added 0.06 ml of trifluoroacetic acid. The solution was stirred for 23 hours at room temperature, washed with 1N sodium hydroxide, dried over sodium sulfate and the solvent removed to give 0.17 g of solid. This solid was dissolved in dichloromethane-ethyl acetate (9:1) and filtered through a thin pad of hydrous magnesium silicate. The filter pad was washed with two 10 ml portions of dichloromethane-ethyl acetate (9:1) and the filtrate and washes combined. The solvent was removed and residual solid washed with hexane to give 0.10 g of white crystals; $[\alpha]_D^{26} -124° \pm 2$ (c, 0.417 CH$_3$OH).

D.
(S)2-Amino-3-cyclohexyl-(R)1-(2-furanyl)propan-1-ol

A 0.15 g sample of (4S-trans) 4-(cyclohexylmethyl)-5-(2-furanyl)-2-oxazolidinone was dissolved in a mixture of 3 ml of ethanol and 3 ml of 1N sodium hydroxide. The solution was refluxed for 17 hours, diluted with 3 ml of water and concentrated under vacuum to remove the ethanol. The aqueous residue was extracted with two 5 ml portions of dichloromethane and the extracts dried over sodium sulfate. The solvent was removed to give 0.15 g of solid which was washed with hexane to give 0.13 g of white solid; $[\alpha]_D^{26} -10° \pm 2$ (c, 0.507, methanol).

REFERENCE EXAMPLE 56

(S)2-Amino-4-methyl-(R)1-(2-thienyl)pentan-1-ol

A 0.81 g portion of (S)2-(tert-butoxycarbonyl)amino-4-methyl-(R,S)-1-(2-thienyl)pentan-1-ol was dissolved in 5 ml of dichloromethane and 2.1 ml of trifluoroacetic acid added. This mixture was stirred for 3 hours, then poured with stirring into 15 ml of ice-cold 2N sodium hydroxide. The mixture was diluted with 25 ml of dichloromethane, the organic layer separated and the aqueous layer extracted with 20 ml of dichloromethane. The organic layer and extract were combined, washed with saturated sodium chloride solution, dried and the solvent removed in vacuo. The residue was chromatographed on a silica gel column with ethyl acetate:hexane (1:4), giving 0.72 g of (4S-trans) 4-(2-methylpropyl)-5-(2-thienyl)-2-oxazolidinone as a white solid; $[\alpha]_D^{26} -141° \pm 2$ (c, 0.570, methanol).

A 0.23 g portion of the above solid was dissolved in 5 ml of 1N sodium hydroxide added. The solution was refluxed for 16 hours and then concentrated in vacuo. The residue was extracted with two 10 ml portions of dichloromethane. The extracts were combined, dried and the solvent removed in vacuo, giving 0.2 g of the desired compound; Rf 0.045 [silica gel; ethyl acetate-hexane (1:2).

REFERENCE EXAMPLE 57

(S)2-Amino-3-cyclohexyl-(R)1-(2-thienyl)propan-1-ol

To a solution of 1.57 g of N-methoxy-N-methyl N$^\alpha$-t-butoxycarbonyl-L-cyclohexylalaninamide in 10 ml of diethyl ether, cooled to $-78°$ C., was added under argon 2.1 ml of 2.35M n-butyllithium in hexane. After stirring for one hour, the mixture was allowed to warm to 0° C. To this was added a solution of 2-lithiothiophene in ether (prepared from 0.64 g of thiophene in 5 ml of ether and 3.2 ml of 3.25M n-butyllithium in hexane at 0° C. for one hour). This mixture was stirred at 0° C. for 2 hours, then quenched with 15 ml of 1N hydrochloric acid and diluted with 25 ml of ether. The organic layer was separated, washed successively with 15 ml of 1N hydrochloric acid, 10 ml of water and 15 ml of saturated sodium bicarbonate, dried and filtered through a short pad of hydrous magnesium silicate. The filter pad was washed with ether, the filtrate and wash combined and evaporated in vacuo. The residue was washed with hexane and then chromatographed on 50 g of silica gel with ethyl acetate-hexane (1:20) as solvent giving 1.2 g of solid. Crystallization from hexane containing a trace of ether gave (S)1,1-dimethylethyl [1-(cyclohexylmethyl)-2-oxo-2-(2-thienyl)ethyl]carbamate as crystals; $[\alpha]_D^{25} +24° \pm 1$ (c, 1.10, methanol).

A solution of 0.51 g of the above compound in 8 ml of dry tetrahydrofuran was cooled to $-78°$ C. under argon and 3 ml of 1.0M potassium tri-sec-butylborohydride in tetrahydrofuran was added dropwise. This mixture was stirred at $-78°$ C. for 4 hours, then quenched with 5 ml of saturated aqueous ammonium chloride, warmed to room temperature and the organic solvent removed in vacuo. The aqueous residue was diluted with 5 ml of water and 20 ml of ethyl acetate. The organic layer was separated and washed successively with two 5 ml portions of saturated aqueous ammonium chloride, 5 ml of saturated aqueous sodium bicarbonate and 5 ml of saturated sodium chloride solution, dried and the solvent removed in vacuo to give (S)2-tert-butoxycarbonylamino-3-cyclohexyl-(R,S)-1-(2-thienyl)propan-1-ol as a gum.

To an 18.4 g sample of the preceding gum in 33 ml of dichloromethane cooled to 0° C. was added 16.75 ml of trifluoroacetic acid. The solution was stirred overnight, cooled to 0° C. and ice cold 1N sodium hydroxide (approximately 300 ml) was added. The organic layer was separated and the aqueous layer extracted with two 350 ml portions of dichloromethane. The organic layer and extracts were combined, washed with two 250 ml portions of brine, dried (Na$_2$SO$_4$) and the solvent removed in vacuum to give 14.5 g of solid.

Trituration with 200 ml of hot hexane, cooling to room temperature and filtering gave 7.5 g of crystals of (4S-trans) 4-(cyclohexylmethyl)-5-(2-thienyl)-2-oxazolidinone as crystals, mp 105°–108° C.

A mixture of 7.0 g of the preceding compound in 13 ml of ethanol and 132 ml of 1N sodium hydroxide was refluxed for 17 hours. The solvent was removed under vacuum and the residue extracted twice with 200 ml of dichloromethane. The combined extracts were dried (Na$_2$SO$_4$) and the solvent removed under vacuum to give 4.64 g of crystals, mp 62°–64° C; $[\alpha]_D^{26} -35° \pm 1$ (c, 1.145, CH$_3$OH).

REFERENCE EXAMPLE 58

N-[N-[2-(1-Naphthalenylmethylene)-3-(morpholinocarbonyl)propionyl]-L-histidyl]-(S)2-amino-3-cyclohexyl-(R)1-(2-thiazolyl)propan-1-ol To a solution of 0.3 g of alpha(1-naphthalenylmethylene-gamma-oxo-4-morpholinebutanoic acid and 0.17 g of triethylamine in 2 ml of dichloromethane was added 0.53 g of benzotriazol-1-yloxy-tris(dimethylamino)-phosphonium hexafluorophosphate (BOP). After stirring for one minute, 0.49 g of N-(L-histidyl)-(S)2-amino-3-cyclohexyl-(R)1-(2-thiazolyl)-1-[(tert-butyldimethyl)silyloxy]propane was added and the mixture was stirred at room temperature overnight. The solvent was removed and to the residue was added 2 ml of acetonitrile and one ml of 40% hydrofluoric acid. The mixture was heated at 55° C. for 4 hours. An additional 2 ml of acetonitrile and one ml of 40% hydrofluoric acid was added and the mixture heated at 55° C. overnight. Ammonium hydroxide was added and the mixture extracted with ethyl acetate. The extract was dried (Na$_2$SO$_4$) and concentrated under vacuum. The residue was dissolved in 2 ml of acetonitrile and one ml of 40% hydrofluoric acid and the mixture heated at 55°–60° C. for 16 hours. The mixture was diluted with 2 ml of water and 5 ml of concentrated ammonium hydroxide. The mixture was extracted with ethyl acetate. The extracts were dried (Na$_2$SO$_4$) and the solvent removed. The residue was chromatographed on silica gel with dichloromethane-methanol-ammonium hydroxide (9:1.2:0.2) as solvent. Fractions containing product were combined and the solvent removed to give 0.18 g of solid. Drying at 50° C. in a vacuum oven gave 0.17 g of glass; $[\alpha]_D^{26} -70° \pm 1$ (c, 1.023, CH$_3$OH).

REFERENCE EXAMPLE 59

N-(L-Histidyl)-(S)2-amino-3-cyclohexyl-(R)1-(2-thienyl)-propan-1-ol

A mixture of 1.18 g of N$^2$-tert-butoxycarbonyl-L-histidine and 0.65 ml of triethylamine in 6 ml of chloroform was stirred and warmed on a steam bath until most of the solid dissolved. To this mixture was added 2.04 g of benzotriazol-1-gloxy-tris(dimethyl amino)phosphonium hexafluorophosphate (BOP) in 2.5 ml of chloroform. The mixture was warmed on a steam bath for 3 minutes and 1.0 g of (S)2-amino-3-cyclohexyl-(R)1-(2-thienyl)-propen-1-ol added. The mixture was stirred at room temperature overnight and refluxed for minutes. The solvent was removed under reduced pressure and the residue dissolved in 25 ml of ethyl acetate. The solution was washed with 10 ml of water, three 10 ml portions of 2M sodium carbonate and 10 ml of brine. The organic layer was dried (Na$_2$SO$_4$), the solvent removed and the residue dried under vacuum to give 1.7 g of N-[N-(tert-butopycarbonyl)-L-histidyl]-(S)2-amino-3-cyclohexyl-($S$)1-(2)-thienylpropan-1-ol as a white foam. To a 0.40 g sample of the preceding compound in 1 ml of tetrahydrofuran cooled to 0° C., was added 3 ml of ice-cold 4N hydrochloric acid. The resulting solution was chilled at 0° C. to 4° C. for seven days and filtered. To the filtrate was added 1.5 ml of 10N sodium hydroxide. The mixture was extracted twice with 2 ml of dichloromethane and the extract dried (Na$_2$SO$_4$). The solution was applied to two 20×20×0.2 cm silica gel plates and the plates developed with dichloromethane-methanol-ammonium hydroxide (9:1.2:02). The product band was removed and extracted with 5% concentrated ammonium hydroxide in methanol. The extract was concentrated under vacuum to give 0.22 g of the product of the Example as a gum.

REFERENCE EXAMPLE 60

(S)2-Amino-3-cyclohexyl-(R)1-2[N-[2-(trimethylsilyl)ethoxyl)methyl imidazolyl) propan-1-ol A solution (cooled to −78° C.) of 17.82 g of 1-[[2-(trimethylsilyl)ethoxy]-1H-imidazole in 90 ml of dry tetrahydrofuran under argon was added slowly 36 ml of n-butyllithium in tetrahydrofuran (2.5 molar) and after complete addition the mixture was stirred at −78° C. for 1 hour (Solution A).

To a stirred solution of 18.84 g of N-methoxy-N-methyl N$^\alpha$-t-butoxycarbonyl-L-cyclohexylalaninamide in 180 ml of dry tetrahydrofuran chilled to −78° C. under argon was added 67 ml of secondary butyllithium in hexane (0.85 molar). After the addition the mixture was stirred for 1.5 hours at −78° (Solution B).

By the use of double-tipped needle technique the solution A was added to the solution B with stirring at −78° C. The mixture was stirred at −78° C. for one hour and allowed to warm to 0° C. and kept (ice bath) at 0° C. for one hour. The mixture was quenched with 150 ml of saturated ammonium chloride solution and the tetrahydrofuran solvent removed under reduced pressure. The residual aqueous layer was extracted twice with 150 ml of ethyl acetate. The combined extract was washed with saturated sodium chloride and dried (Na$_2$SO$_4$). The solvent was removed under vacuum to give 3.50 g of dark orange oil. This oil (35 g) was chromatographed on a silica gel column with ethyl acetatehexane (1:10) to give 17.82 g of 1,1-dimethylethyl (S)-[1-(cyclohexyl-methyl)-2-oxo-2-(2-[N-[2-trimethylsilyl)ethoxy]methyl]imidazolyl)ethyl]carbamate as a yellow visious oil; $\lambda\alpha]_D^{26} +15° \pm 1$ (c,1.234,CH$_3$OH).

To a solution of 19.12 g of the preceding compound in 170 ml of dry tetrahydrofuran cooled to −78° C. was added dropwise 85 ml of potassium tri-sec-butylborohydride in tetrahydrofuran (1.0M). After the addition, the mixture was stirred at −78° C. for 2 hours and 170 ml of saturated ammonium chloride solution was added. The mixture was allowed to warm to room temperature and the tetrahydrofuran removed under vacuum. The aqueous residue was dilated with 50 ml of hydrogen peroxide (30% by weight in water) added dropwise (exothermic). After the addition was complete, the ice bath was removed and the mixture stirred for one hour. The mixture was cooled to 0° C. and 93 g of sodium sulfate added in six equal portions. The mixture was stirred for 15 minutes, the organic layer separated, and the aqueous layer extracted with 200 ml of ethyl acetate. The organic layer and the extract were combined, dried over Na$_2$SO$_4$ and the solvent removed to give a white solid. The solid was dissolved in a mixture of 400 ml of hexane and 50 ml of ethyl acetate by warming on a steam bath. Cooling gave 14.13 g of (S)2-tert-butoxycarbonylamin-3-cyclohexyl-(R)1-(2-[N-[-2-(trimethylsilyl)-ethoxy]methyl]imidazolyl)propan-1-ol as white crystals, mp 97°–99° C.; $[\alpha]_D^{26} +8° \pm 1$ (c, 1.15,CH$_3$OH).

A 20 g sample of the preceding compound was dissolved in 110 ml of ethanol. To the stirred solution was added 110 ml of 2N hydrochloric acid and the solution heated in an oil bath at 70° C. to 75° C. for 2 hours. The solution was diluted with 85 ml of water and concentrated under vacuum to remove the ethanol. The aqueous residue was chilled to 0° C. and made basic with 2N sodium hydroxide. The mixture was extracted twice with 300 ml of ethyl acetate and the extracts combined. The extract was washed with 250 ml of brine, dried (Na$_2$SO$_4$) and the solvent removed under vacuum. The residue was dried at 55° C. for 5 hours to give 14.1 g of (S)2-amino-3-cyclohexyl-(R)1-(2-[N-[2-(trimethylsilyl)ethoxy]methyl]imidazole)propan-1-ol as a light yellow oil; $[\alpha]_D^{26} -8° \pm 1$ (c, 1.05, CH$_3$OH).

REFERENCE EXAMPLE 61

N-(L-Histidyl)-(S)2-amino-3-cyclohexyl-(R)1-2(2-[N-[2-(trimethylsilyl) ethoxyl]methlyl]imidazolyl)propan-1-01

To a solution of 30.45 g of imidazole in 150 ml of chloroform under argon was added 12.60 of phenyl dichlorophosphate in 50 ml of chloroform. The mixture was stirred at room temperature for 0.5 hour and then cooled to 0° C. To the cooled mixture was added 15.24 g of N$^\alpha$-tertbutoxycarbonyl-L-histidine and the mixture stirred for 2 hours. To the solution was added dropwise 14.1 g of (S)2-amino-3-cyclohexyl-(R)1-(2-[N-[2-(trimethylsilyl)ethoxy]methyl]imidazolyl)propan-1-ol in 40 ml of chloroform. The mixture was stirred at 0° C. for 44 hours, diluted with 400 ml of water and extracted with 1 liter of ethyl acetate. The extract was washed with two 350 ml portions of water, 350 ml of saturated sodium carbonate solution and dried (Na₂SO₄). The solvent was removed to give 29.0 g of solid. This solid was dissolved in 200 ml of methanol and 100 ml of 1N sodium hydroxide added. The solution was stirred overnight at room temperature, diluted with 100 ml of water and concentrated under vacuum. The mixture was extracted with two 300 ml portions of ethylacetate and the extract washed with 250 ml of brine and dried (Na₂SO₄) the solvent was removed under vacuum to give 24.6 g of a glass.

REFERENCE EXAMPLE 62

N-(L-Histidyl)-(S)2-amino-3-cyclohexyl-(R)1-(2-furanyl)propan-1-ol

As described for Reference Example 59, a mixture of 1.28 g of N-tert-butoxycarbonyl-L-histidine, 0.72 ml of trimethylamine and 0.005 mole of benzotriazol-1-gloxy-tris(dimethylamino)phosphonium hexafluorophosphate in 10 ml of chloroform was warmed and stirred for 3 minutes. To this misture was added 1.12 g of (S)2-amino-3-cyclohexyl-(R)-1-(2-furanyl)propan-1-ol and the mixture stirred for 16 hours. Work up and removal of the N-tert-butoxycarbonyl blocking group as described for Reference Example 59 gave 0.2 g of the product as a glass.

REFERENCE EXAMPLE 63

N-[2-(2-methylpropoxy)glycyl]-(S)2-amino-3-cyclohexyl-(R)1-(2-ovridinyl)propan-1-ol A mixture of 30.33 g of benzyl carbonate, 20.2 g of glyoxylic and in 200 ml of ether was stirred at room temperature overnight. The solution was cooled at 0° C. for 30 minutes, filtered and the solid washed with ether. The solid was dried to give 28.2 g of N-(benzyloxycarbonyl)-2-hydroxyglycine as crystals, mp 194°-198° C.

A mixture of the preceding compound (4.0 g) in 80 ml of 2-methylpropanol and 0.4 ml of concentrated sulfuric and was stirred at room temperature overnight. The solution was diluted with 100 ml of ethyl acetate and washed with 10% sodium bicarbonate, water and brine. The organic layer was dried (MgSO₄) and the solvent removed. The residue (5.8 g) was dissolved in chloroform and the solution filtered through a short silica gel column. The filtrate was concentrated under vacuum to give 3.36 g of 2-methylpropyl N-(benzyloxycarbonyl)-2-(2-methylpropoxyl)glycinate as a clear oil.

The preceding compound (3.9 g) was dissolved in 120 ml of methanol and 11.6 ml of 1M sodium hydroxide added. The solution was stirred overnight and 3.9 ml of 3N hydrochloric acid added. The solvent was removed and the residue dissolved in 10% NaHCO₃. The mixture was extracted twice with ether. The aqueous layer was acidified with 6N hydrochloric acid, and extracted with dichloromethane. The dichloromethane extract was dried (MgSO₄) and the solvent and the solvent removed to give 2.97 g of N-(benzyloxycarbonyl)-2-(2-methylpropoxy)glycine as a white solid, mp 66°-68° C. To a solution of 0.432 g of the preceding compound in 10 ml tetrahydrofuran was added 0.249 g of N,N-carbonyldiimidazole. After stirring at room temperature for 2 hours, 0.30 g of (S)2-amino-3-cyclohexyl-(R)1-(2-pyridinyl)propan-1-ol was added and the solution was stirred overnight. The solvent was removed and the residue in dichloromethane washed with 10% NaHCO₃. The aqueous layer was extracted with dichloromethane. The organic layer and extract were combined and washed with brine, dried (Na₂SO₄) and the solvent removed under vacuum. The residue was dried under vacuum to give 0.653 g of the product as a gum.

REFERENCE EXAMPLE 64

(S)2-Amino-3-cyclohexyl-(R)1-(5-acetyl-2-furonyl)propan-1-ol

To a solution of 0.50 g of (4S-trans)4-(cyclohexylmethyl)-5-(2-furanyl)-2-oxazolidinone in 8 ml of tetrahydrofuran, cooled to −78° C., was added 1.8 ml of n-butyllithium in hexane (2.2M). After 15 minutes the solution was warmed to room temperature and N-methoxy-N-methyl acetamide in 1 ml of tetrahydrofuran was added. The mixture was stirred at room temperature for 3 hours and quenched with 4 ml of saturated ammonium chloride solution and 4 ml of water. The mixture was concentrated under vacuum to remove the tetrahydrofuran and then extracted with 20 ml of ethyl acetate. The extract was washed with 10 ml each of 1N hydrochloric acid, saturated sodium bicarbonate and brine. The organic layer was dried (Na₂SO₄) and the solvent removed to give 0.58 g of solid. Flash chromatography on silica gel with ethyl acetate-hexane (1:1) as solvent gave 0.29 g of (4S-trans)4-(cyclohexylmethyl)-5-(5-acetyl-2-furanyl)-2-oxazolidinone as a cream colored solid; $[\alpha]_D^{26} -116° \pm 1$ (c, 0.773, CH₂OH).

The preceding compound was dissolved in a mixture of 4 ml of ethanol and 4 ml of 1N sodium hydroxide and the solution heated at 80° C. for 6 hours. The solution was diluted with 4 ml of water, concentrated to remove the ethanol, and extracted twice with 8 ml of dichloromethane. The extract was dried (Na₂SO₄) and the solvent removed to give 0.11 g of solid. Flash chromatography on silica gel with 10% methanol in dichloromethane gave 85 mg of product as a yellow solid: $[\alpha]_D^{26} +64° \pm 2$ (c, 0.464, CH₂OH).

The following Reference Examples may be prepared by the procedure of Reference Example 64.

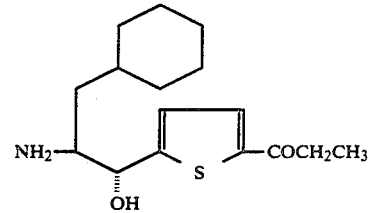

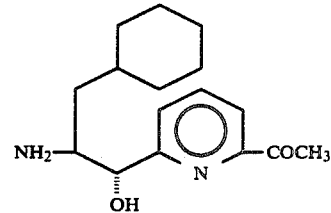

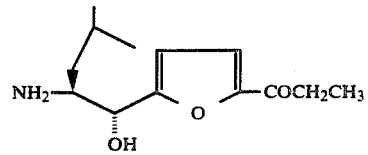

-continued

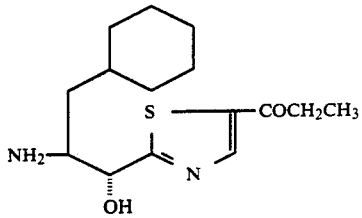

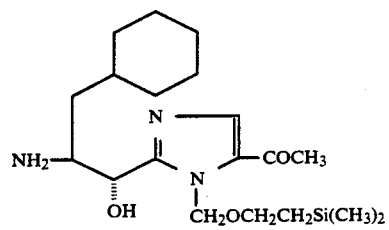

REFERENCE EXAMPLE 65

(S)2-Amino-3-cyclohexyl-(R)1-(5-methoxycarbonyl-2-thiazolyl)-1-(tert-butyldimethylsilyloxy)propane To a solution of 0.23 g of N-tert-butoxycarbonyl-(S)2-amino-3-cyclohexyl-(R)1-(2-thiazolyl)-1-(tert-butyldimethylsilyloxy)propane in 2 ml of tetrahydrofuran under argon at −78° C., was added 0.45 ml of n-butyllithium in hexane (2.2M). After 0.5 hour at −78° C., the mixture was allowed to warm to 0° C. and stand for 0.5 hour. Carbon dioxide gas was bubbled through the stirred suspension for 1 hour at 0° C. and the mixture diluted with 2 ml of water and 2 ml of saturated ammonium chloride. The mixture was concentrated under vacuum and the residue extracted with 15 ml of diethyl ether. The ether extract was washed twice with ml of 1N sodium hydroxide and with 5 ml of brine. A white precipitate formed in the ether layer and was filtered off and washed with ether. This white precipitate was combined with the sodium hydroxide washes and the mixture acidified with 6N hydrochloric acid. The acidified mixture was extracted with 15 ml of ethyl acetate and the extract washed with brine and dried ($Na_2SO_4$). The solvent was removed to give a solid which crystallized from isooctane to give 0.20 g of N-tert-butoxycarbonyl-(S)2-amino-3-cyclohexyl-(R)1-[2-(5-carboxy)thiazolyl]-1-(tert-butyldimethylsilyloxy)propane.

The preceding compound (0.13 g) in 0.5 ml of tetrahydrofuran was added to a solution of 49 mg of N,N-carbonyldiimidazole in 0.5 ml of tetrahydrofuran under argon. The mixture was stirred at room temperature for 1 hour and 0.5 ml of dry methanol added. The solution was stirred at room temperature for 17 hours and the solvent removed. The residue in 10 ml of ethyl acetate was washed with two 5 ml portions of 0.5 N hydrochloric acid, 5 ml of 1N sodium hydroxide, brine and dried ($Na_2SO_4$). The ethyl acetate solution was filtered through a thin pad of hydrous magnesium silicate and the pad washed with ethyl acetate. The filtrate was evaporated under vacuum to give 0.12 g of N-tert-butoxycarbonyl-(S)2-amino-3-cyclohexyl-(R)1-(5-methoxycarbonyl-2-thiazolyl)-1-(tert-butyldimethylsilyl-oxy)propane as a gum.

The preceding compound (0.12 g) was dissolved in 1 ml of dichloromethane and 0.18 ml of trifluoro acetic acid added. The solution was stirred at room temperature for 22 hours and then poured into 3 ml of ice cold 1N sodium hydroxide. The mixture was extracted with 10 ml of dichloromethane and the extract dried ($Na_2SO_4$). The solvent was removed to give 0.095 g of the product as a colorless gum.

REFERENCE EXAMPLE 66

N-[N-[(R)2-(1-Naphthalenylmethyl)-3-(carboxy)propionyl]-]-L-histidyl]-(S)2-amino-3-cyclohexyl-(R)1-(2-[N-[2-(trimethylsilyl)ethoxy]methyl]imidazolyl)propan-1-ol A solution of 0.11 g of (R)2-(1-naphthalenylmethyl)-3-(tert-butoxycarbonyl)propionic acid and 0.058 g of N,N-carbonyldiimidazole in 2 ml of dichloromethane was stirred at room temperature for one hour under argon. To this solution was added a solution of 0.15 g of N-(L-histidyl)-(S)2-amino-3-cyclohexyl-(R)1-(2-[N-[2-(trimethylsilyl)ethoxy]methyl]imidazolyl)propan-1-ol in 0.5 ml of dichloromethane. The mixture was stirred for 19 hours and an additional solution of (R)2-(1-naphthalenylmethyl)-3-(tertbutoxycarbonyl)propionic acid (47 mg) and N,N-carbonyldiimidazole (24 mg) in 0.5 ml of dichloromethane added. The solution was stirred for 2 days, 2 ml of tetrahydrofuran added and the mixture stirred for 1 day. The solvent was removed under vacuum and the residue washed with water. The water insoluble solid was dissolved in ethyl acetate and the solution washed with brine, dried ($Na_2SO_4$) and the solvent removed to give 0.34 g of a gum. Trituration with ether-hexane gave 0.32 g of solid. This solid was chromatographed in silica gel with dichloromethane-methanol-ammonium hydroxide (10:0.5:0.0.05) to give 0.18 g of N-[N-[(R)2-(1-naphthalenylmethyl)-3-(tert-butoxycarbonyl)propionyl]-L-histidyl]-(S)2-amino-3-cyclohexyl-(R)1-(2-[N-[2-(trimethylsilyl)ethoxy]methyl]imidazolyl)propan-1-ol as a white solid: $[\alpha]_D^{26} +43° \pm 2$ (c, 0.612, $CHCl_3$).

A mixture of 0.10 g of the preceding compound, 0.2 ml of tetra-n-butylammonium fluoride in tetrahydrofuran (1.0M) and 0.5 ml of hexamethyl-phosphoramide was stirred at room temperature for 3 hours. The mixture was diluted with water (5 ml) and 1 ml of saturated ammonium chloride. The precipitate was filtered off and washed twice with 2 ml of water to give 0.10 g of white solid. Purification by chromatography on silica gel with dichloromethane-methanol ammonium hydroxide (10:0.5:0.05) gave 0.060 g of the product as a white solid.

REFERENCE EXAMPLE 67

(4S-trans)-4-(Cyclohexylmethyl)-5-(2-pyridinyl)-2-oxazolidinone

As described in Reference Example 16, 20.27 g of 1,1-dimethylethyl (S)[1-(cyclohexylmethyl)-2-oxo-2-(2-pyridinyl)ethyl]carbonate in 300 ml of tetrahydrofuran at −78° C. was reduced with 155 ml of potassium tri-sec-butyl-borohydride (0.155M) cooled to −78° C. After 5 hours at −78° C., the mixture was quenched with 50 ml of water and after warming to 0° C. additional water (200 ml) was added. The mixture was extracted with two 250 ml portions of ethyl acetate and the extract dried ($Na_2SO_4$) and the solvent removed. The residue (41 g) was dissolved in 30 ml of tetrahydrofuran and 150 ml of 6N hydrochloric acid added. The mixture was stirred at room temperature for 5 hours, diluted with 40 ml of water and extracted with 50 ml of ether. The aqueous layer chilled and 110 ml of 10N sodium hydroxide added slowly. The mixture was extracted with three 200 ml portions of dichloromethane and the extract washed with brine (200 ml) and dried over anhydrous potassium carbonate. The solvent waws removed to give 15.0 g of solid. This solid was chromatographed on silica gel with a Waters-HPLC Prep-500 apparatus with dichloromethane-methanol-triethylamine (97:2:1) as solvent to give 9.0 g of (S)2-amino-3-cyclohexyl-(R)1-(2-pyridinyl)propanol as crystals, mp 53°-55° C. and 3.0 g of (S)2-amino-3-cyclohexyl-(S)-1-(2-pyridinyl)propan-1-ol as an oil.

A 2.8 g sample (S)2-amino-3-cylohexyl-(S)1-(2-pyridinyl)propan-1-ol was dissolved in 24 ml of dioxane-water (1:1) and 3.14 g of $\eta$-butylpyrocarbonate in 13 ml of dioxane added, dropwise, with stirring. The solution was stirred 17 hours, diluted with 20 ml of water and extracted with two 75 ml portions of ethyl acetate. The extract was washed with brine, dried (Na$_2$SO$_4$) and the solvent removed. The residual oil was chromatographed on silica gel with ethyl acetatehexane (4:6) as solvent to give 3.0 g of N-(tert-butoxycarbonyl)-(S)2-amino-3-cyclohexyl-(S)1-(- 2-pyridinyl)propan-1-ol as white crystals; $[\alpha]_D^{26} -14°\pm 1$ (c, 0.984, CHCl$_3$) mp 84°-85° C. To the preceding compound (0.334 g) in 10 ml of dichloromethane was added 0.20 ml of triethylamine and the mixture cooled to 5° C. To the solution was added 0.10 ml of methanesulfonyl chloride and the mixture stirred for 1.5 hours at 5° C. The solvent was removed and the residue dissolved in methanol and allowed to stand at room temperature for 24 hours. The mixture was diluted with 20 ml of water and extracted with 50 ml of ethyl acetate. The extract was washed with water, brine, dried (Na$_2$SO$_4$) and the solvent removed to give a pale yellow oil. Chromatography on silica gel with ethyl acetate heptane (2:3) gave 0.195 g of (4-S-trans)-4-(cyclohexylmethyl)-5-(2-pyridinyl)-2-oxazolidinone as thick pale yellow oil $[\alpha]_D^{26} -46°\pm$(c, 1.08, CH$_3$OH).

The preceding compound was also prepared by reacting 0.300 g of (S)2-amino-3-cyclohexyl-(R)1-(2-pyridinyl)propan-1-ol with 0.49 g of N,N-carbonyldiimidazole in refluxing tetrahydrofuran (25 ml) for 16 hours.

REFERENCE EXAMPLE 68

4S-trans)-4-(cyclohexylmethyl)-5-(2-thiazolyl)-2-oxazolidinone

A solution of 0.24 g of (S)2-amino-3-cyclohexyl-(R)1-(2-thiazolyl)propan-1-ol and 0.11 g of N,N-carbonyldiimidazole in 5 ml of tetrahydrofuran was stirred at room temperature for 16 hours and then refluxed for 5 hours. The solvent was removed and the residue dissolved in 15 ml of ethyl acetate. The solution was washed twice with 5 ml of [1N hydrochloric acid, with 5 ml of sodium bicarbonate, with 5 ml of brine and dried (Na$_2$SO$_4$)]. The solvent was removed and the residue washed with hexane to give 0.26 g of a colorless glass; $[\alpha]_D^{26} -88°\pm 1$ (c, 1.072, CH$_3$OH)

REFERENCE EXAMPLE 69

(4S-trans)-4-(Cyclohexylmethyl)-5-[[2-(trimethyl-silyl)ethoxy]methyl]-1H imidazol-2-yl[-2-oxazolidinone To a solution of 0.35 g of (S)2-amino-3-cy clohexyl-methyl-(R)1-2-[N-[2-(trimethylsilyl)ethoxy]-methyl-]imidaqzolyl)propan-1-ol in 2 ml of diethylcarbonate was added 0.41 g of potassium carbonate and 0.16 g of sodium methoxide. The suspension was heated at 80° C. for 21 hours and at 100° C. for 6 days. The mixture was quenched with 5 ml of water and extracted with 15 ml of ethyl acetate. The extract was washed with brine dried (Na$_2$SO$_4$) and the solvent removed. The residue was chromatographed on silica gel (20 g). The column was eluted with hexane (200 ml) and then with ethyl acetate-hexane (1:1) to give 0:33 g of a colorless gum: $[\alpha]_D^{26} -138°\pm 1$ (c, 1.042, CH$_3$OH).

REFERENCE EXAMPLE 70

N-(L-Leucyl)-(S)-2-amino-3-cyclohexyl-(R)-1-(2-furanyl)propan-1-ol

To a solution of 1.4 g of imidazole in 18 ml of dichloromethane is added 0.90 ml of phenyl dichlorophosphate in 6 ml of dichloromethane. The mixture is stirred for 20 minutes, cooled to 0° C. and a solution of 0.60 g of imidazole, 2.4 ml of N,N-dimethylformamide and 1.6 g of N$^\alpha$-[(benzyloxy)carbonyl]-L-leucine in 6 ml of tetrahydrofuran added. The mixture is stirred at 0°C. for 40 minutes and then 1.30 g of (S)-2-amino-3-cyclohexyl-(R)-1-(2-furanyl)propan-1-ol added. The mixture is stirred at 0° C. to 25° C. (ice bath allowed to melt) overnight and the solvent removed. The residue is dissolved in 20 ml of ethyl acetate and washed with water, 2N citric acid, sodium bicarbonate solution and dried (MgSO$_4$). The solution is filtered through a thin pad of hydrous magnesium silicate and the pad washed with several volumes of ethyl acetate. The filtrate is concentrated under vacuum to give 2.3 g of N-[N-(benzyloxy)carbonyl-L-leucyl]-(S)-2-amino-3-cyclohexyl-(R)-1-(2-furanyl)propan-1-ol as an oil. The preceding compound (1.85 g) and 1.0 g of ammonium formate in 24 ml of methanol under nitrogen is warmed on a steam bath and then the solution is chilled to 0° C. To the mixture (without stirring) is added (by pipette) 0.96 g of 10% palladium on carbon suspended in 5 ml of ethanol. The mixture is stirred at 0° C. for one hour, diatomaceous earth added and the mixture filtered. The filter pad is washed with methanol and the filtrate evaporated to dryness. The residue is partitioned between ammonium hydroxide and dichloromethane. The organic layer is separated, dried (MgSO$_4$) and the solvent removed to give 1.24 g of a gum. Crystallization from 5 ml of diisopropyl ether gives 0.74 g of N-(L-leucyl)-(S)-2-amino-3-cyclohexyl-(R)-1-(2-furanyl)propan-1-ol as colorless crystals, mp 83°-84° C. $[\alpha]_D^{26} -17°\pm 1$ (c, 1.031, CH$_3$OH).

REFERENCE EXAMPLE 71

N-[N-(Benzyloxy)carbonyl-L-leucyl]-(S)-2-amino-3-cyclohexyl-(R)-1-(2-furanyl)propan-1-ol To a solution of 4.0 g of N-(benzyloxy)carbonyl-L-leucine (4.99 g) in 40 ml of dry tetrahydrofuran is added 3.05 g of N,N-carbonyldiimidazole. The solution is stirred at room temperature for 2.0 hours and then 4.0 g (S)-2-amino-3-cyclohexyl-(R)-1-(2-furanyl)propanol is added. After stirring 5 hours under argon, the solvent is removed and the residue is dissolved in 80 ml of dichloromethane. The solution is washed twice with 40 ml of 2N citric acid, once with 40 ml of water 1M sodium bicarbonate and brine. The organic layer is dried (MgSO$_4$) and the solvent removed to give and oil. Crystallization from diisopropyl ether gives 7.0 g of white crystals, mp 95°-97° C.; $\lambda\alpha]_D^{26} -39°\pm 1$ (c, 1.029, CH$_3$OH).

REFERENCE EXAMPLE 72

N-[N-(Benzyloxycarbonyl)-L-histidyl]-(S)-2-amino-3-cyclohexyl-(R)-1-(2-furanyl)propan-1-ol Imidazole (2.2 g) is dissolved in 26 ml of dichloromethane and 2.06 g of phenyl dichlorophosphate in 8 ml of dichloromethane added. After stirring under argon for 10 minutes, the mixture is cooled to 0° C. and a solution of 2.82 g of $N^\alpha$-(benzyloxycarbonyl)-L-histidine and 0.94 g of imidazole in a mixture of 3.4 ml of N,N-dimethylformamide and 17 ml of dichloromethane is added. The mixture is stirred at 0° C. for 1 hour and a solution of 2.14 g of (S)-2-amino-3-cyclohexyl-(R)-1-(2-furanyl)propan-1-ol in 6 ml of dichloromethane added. The mixture is allowed to warm to room temperature over 5 hours and is stirred for 2 days. The mixture is concentrated under vacuum and diluted with 100 ml of ethyl acetate. The mixture is washed with 1M sodium bicarbonate, and a solution of 1M citric acid-1M-sodium citrate and dried (MgSO$_4$). The solvent is removed to give 4.8 g of solid. This solid is chromatographed on silica gel by HPLC on a Waters-Prep 500 A apparatus with ethyl acetate-methanol-triethylamine (96:2:2) as solvent. Cuts containing product are combined and the solvent removed under vacuum to give 2.54 g of solid; $[\alpha]_D^{26} -21° \pm 1$ (c, 0.932, CH$_3$OH); FAB (Mass Spectrum); Found M+H=495.

REFERENCE EXAMPLE 73

N-(L-histidyl)-(S)2-amino-3-cyclohexyl-(R)1-(2-furanyl)-propan-1-ol

To a mixture of 1.25 g of imidazole in 0.5 ml of dichloromethane is added 1.2 g of phenyl dichlorophosphate in 5 ml of dichloromethane. After stirring for 25 minutes the mixture is chilled to 0° C. and to the mixture is added a warm solution of 1.65 g of $N^\alpha$-(benzyloxycarbonyl)-L-histidine and 0.55 g of imidazole in 2 ml of dry N,N-dimethylformamide. The mixture is diluted to a volume of 10 ml with dichloromethane and stirred at 0° C. for 1 hour. To the mixture is added 1.25 g of (S)2-amino-3-cyclohexyl-(R)1(2-furanyl)propan-1-ol and the mixture stirred overnight at 0° C. to 25° C. (ice bath allowed to melt). The mixture is concentrated under vacuum and the residue in 20 ml of ethyl acetate washed with 5 ml of water, with three 5-ml portions 1M sodium bicarbonate and brine. The organic layer is dried (Na$_2$SO$_4$) and the solvent removed to give 2.4 g of N-[N-(benzyloxycarbonyl)-L-histidyl]-(S) 2-amino-3-cyclohexyl-(R)-1-(2-furanyl)propan-1-ol as a gum. A mixture of the preceding gum (2.4 g), 1.52 g of amnonium formate, 0.37 ml of formic acid (90%) and 30 ml of methanol under nitrogen is chilled to 0° C. and then a slurry of 1.2 g of 10% palladium on carbon in ethanol is added by pipette. The cooled mixture is stirred 2.5 hours and filtered through diatomaceous earth. The filtrate is evaporated and to the residue is added 1 ml of concentrated ammonium hydroxide. The mixture is extracted successively with 10-ml, 5-ml and 5-ml portions of ethyl acetate. The combined extracts are dried (Na$_2$SO$_4$) and the solvent removed to give 1.2 g of a glass. This glass is chromatographed on a silica gel column with a solvent system of dichloromethane; methanol; triethylamine (94;6:2). Cuts containing product are combined, concentrated to dryness and partitioned between 10 ml of 2 N ammonium hydroxide and 5 ml of dichloromethane. The organic layer is separated and the aqueous layer extracted with two 5-ml portions of dichloromethane. The organic layer and extracts are combined, dried (Na$_2$SO$_4$) and the solvent removed to give 0.22 g of solid; Mass Spec (FAB): found, 361 (M+H); calc, 361 (M+H); calc, 361 (M+H).

REFERENCE EXAMPLE 74

1,4-Dioxa-8-azaspiro[4.5]decane-8-carboxylic acid, (S)-2-methoxy-2-oxo-1-(phenylmethyl)ethyl ester To a solution of 6.0 g of L-phenyllactic acid, methyl ester in 180 ml of tetrahydrofuran is added 0.200 g of activated carbon, and 10.1 ml of trichloromethyl chloroformate (diphosgene). The mixture is heated at 55° C. for 3.25 hours and an additional 2.0 ml of trichloromethyl chloroformate added. The mixture is heated at 55° C. for 3.25 hours, filtered through diatomaceous earth and the filtrate concentrated to dryness. The residue (under argon) is dissolved in 160 ml of dichloromethane, chilled in an ice bath and 9.5 g of 1,4-dioxa-8-azaspiro[4.5]decane added. To the mixture is added 4.64 ml of triethylamine in 20 ml of dichloromethane over 15 minutes. The mixture is stirred overnight (ice bath allowed to melt). The mixture is washed with 100 ml of 10% sodium bicarbonate, 100 ml of brine and the solvent removed. The residue is dissolved in dichloromethane, dried (MgSO$_4$) and the solvent removed under vacuum to give 12.5 g of brown solid. The solid is dissolved in dichloromethane-ethyl acetate (9:1) and the solution filtered through a thin pad of hydrous magnesium silicate. The pad is washed with dichloromethane-ethyl acetate (9:1) and the combined filtrates concentrated under vacuum to give 11.5 g of off white crystals, mp 86°-88.5° C.; $[\alpha]_D^{26} -23° \pm 1$ (c, 1.09, CH$_3$OH).

REFERENCE EXAMPLE 75

1,4-Dioxa-8-azaspiro[4.5]decane-8-carboxylic acid, [S-(R*,R*)]-2-[[1-(methoxycarbonyl)-3-methylbutyl]-amino1-2-oxo-1-(phenylmethyl)ethyl, ester To a solution of 5 g of 1,4-dioxa-8-azaspiro-[4.5]decane-8-carboxylic acid, (S)-2-methoxy-2-oxo-1-(phenylmethyl)ethyl ester, in 65 ml of methanol is added a solution of 0.752 g of lithium hydroxide in 7 ml of water. The mixture is stirred at room temperature for 2.5 hour and 3M hydrochloric acid (26 ml) is added. The mixture is concentrated under vacuum and the residue partitioned between water and dichloromethane. The organic layer is separated and the aqueous layer extracted twice with dichloromethane. The combined organic layer and extracts were dried (MgSO$_4$) and the solvent removed to give 5.0 g of a clear foam. The preceding foam (5.0 g) is dissolved in 10.5 ml of tetrahydrofuran under argon and 2.32 g N,N-carbonyldiimidazole added. The solution is stirred at room temperature for 2.5 hours and 3.25 g of L-leucine methyl ester, hydrochloride added. The mixture is stirred overnight, filtered and the filtrate concentrated to dryness. The residue is dissolved in 100 ml of ethyl acetate and the solution washed with 10% hydrochloric acid, 10% sodium bicarbonate and dried (MgSO$_4$) The solvent is removed and the residue dissolved in ethyl acetate-dichloromethane (1:4) and filtered through silica gel. The filtrate is concentrated under vacuum to give 6.3 g of a pale yellow gum; CI-Mass spectrum; MH+=463; $[\alpha]_D^{26} -33° \pm 1$ (c, 1.085, CH$_3$OH).

REFERENCE EXAMPLE 76

4-Acetyl-1-piperazinecarboxylic acid, (S)1-carboxy-2-phenylethyl ester

To a solution of 5.40 g of L-phenyllactic acid, methyl ester in 80 ml of tetrahydrofuran under argon is added 0.176 g of activated carbon and 3.62 ml of trichloromethyl chloroformate (diphosgene) and the mixture heated at 55° C. for 2 hours. An additional 1.8 ml of trichloromethyl chloroformate is added and the mixture heated at 55° C. for 45 minutes. The mixture is cooled to 23° C., filtered through diatomaceous earth and the filtrate concentrated to dryness under vacuum. After 1.5 hour under high vacuum, the residue under argon is dissolved in 150 ml of dichloromethane and cooled to 0° C. To this solution is added 11.5 g of 4-acetylpiperazine in 35 ml of dichloromethane over 15 minutes. The mixture was stirred at 4° C. overnight and washed with 140 ml of 0.5N hydrochloric acid and 10% sodium bicarbonate solution. The organic layer is dried (MgSO$_2$) and the solvent removed under vacuum to give 10.1 g of pale yellow gum. Chromatography over silica gel on a Water-Prep 500 HPLC apparatus with dichloromethane-ethyl acetate (9:1) as solvent gives 7.3 g of a clear viscous gum; $[\alpha]_D^{26} -27° \pm 1$ (c, 0.986, CH$_3$OH). The preceding compound, 4-acetyl-piperazinecarboxylic acid, (S)2-methoxy-2-oxo-1-(phenylmethyl)ethyl ester (7.1 g), is dissolved in 75 ml of methanol and a solution of 1.12 g of lithium hydroxide in 10 ml of water is added. The mixture is stirred at room temperature for 3 hours and acidified with 3N hydrochloric acid (9 ml) and the solvent removed under vacuum. The residue is partitioned between ethyl acetate and water. The organic layer is separated and the aqueous layer extracted twice with ethyl acetate. The organic layer and extracts are combined and the solvent removed under vacuum to give 5.8 g of a white foam; $[\alpha]_D^{26} -41° \pm 1$ (c, 1.113, CH$_3$OH).

REFERENCE EXAMPLE 77

[S-(R*,R*)][-2-[(1-Carboxy-3-methylbutyl)amino]-1-oxo-1-(phenylmethyl)ethyl 4-acetyl-1-piperazinecarboxylate To a solution of 5.6 g 4-acetyl-1-piperazinecarboxylic acid, (S)1-carboxy-2-phenylethyl ester in 125 ml of tetrahydrofuran under argon is added 2.84 g of N,N-carbonyldiimidazole. The mixture is stirred at room temperature for 2.5 hours and 3.98 g of L-leucine methyl ester hydrochloride added. The mixture is stirred ovenight, filtered to removed solid and the filtrate concentrated to dryness. The residue is dissolved in 100 ml of dichloromethane and the solution washed with 50 ml of 10% hydrochloric acid, 50 ml of 10% sodium bicarbonate and dried (MgSO$_4$) The solvent is removed to give 7.7 g of a white foam. Chromatography over silica gel with ethyl acetate-dichloromethane (1:1) as solvent and then with ethyl acetatemethanol (9:1) gives 7.6 g of 4-acetyl-1-piperazinecarboxylic acid, [S-(R*,R*)]-2-[[1-(methoxycarbonyl)-3-methylbutyl]amino]-2-oxo-1-(phenylmethyl)ethyl ester as a clear foam; $[\alpha]_D^{26} -41° \pm 1$ (c, 1.262, CH$_3$OH).

The preceding compound (7.5 g) is dissolved in 60 ml of methanol and 0.879 g of lithium hydroxide in 8 ml of water added. The mixture is stirred at room temperature for 3.25 hours, acidified with 7.5 ml of 3N hydrochloric acid and concentrated under vacuum. The residual solid is slurried in water, filtered and the solid washed with water to give 6.97 g of crystals. Recrystallization from ethanol gives 6.52 g of white crystals, mp 142°–144° C.; $[\alpha]_D^{26} -35° \pm 1$ (c, 1.122, CH$_3$OH).

REFERENCE EXAMPLE 78

(S)-2-(4-Oxo-1-piperidinyl)carbonyl]oxy]-3-phenylpropionic acid

To a solution of 2.0 g of 1,4-dioxa-8-azaspiro[4.5]decane-8-carboxylic, (S)2-methoxy-2-oxo-1-(phenylmethyl)ethyl ester in 26 ml of methanol is added 0.337 g of lithium hydroxide in 3.5 ml of water. The mixture is stirred at room temperature for 2 hours and 2.7 ml of 3N hydrochloric acid added. The solvent is removed under vacuum and the residue extracted with dichloromethane. The extract is dried (MgSO$_4$) and the solvent removed to give 5.7 g of solid. This solid is dissolved in 75 ml of tetrahydrofuran and 15 ml of 1N hydrochloric acid added. The mixture is stirred overnight, refluxed for 5 hours and stirred overnight. An additional 15 ml of 1N hydrochloric acid is added and the mixture refluxed for 3 hour. The solvent is removed and the aqueous residue extracted with dichloromethane. The extract is dried (MgSO$_4$), the solvent removed and the residue crystallized from toluene to give 0.835 g of white crystals, mp 135°–136.5° C.; $[\alpha]_D^{26} -37° +1$ (c, 1.01, CH$_3$OH).

REFERENCE EXAMPLE 79

Methyl (S)2-[[(3-oxo-1-piperazinyl)carbonyl]oxy]-3-phenylpropionate

To a mixture of 8.28 g of methyl L-3-phenyllactate and 0.200 g of activated carbon in 250 ml of tetrahydrofuran under argon is added 17 ml of diphosgene. The mixture is heated at 55° C. (internal temperature) for 3 hours and filtered through diatomaceous earth. The filtrated is concentrated under vacuum and pumped under high vacuum. The residue under argon is dissolved in 220 ml of tetrahydrofuran and the solution chilled. (Solution A)

A solution of 4.52 g of 2-ketopiperazine is prepared by heating with 160 ml of dioxane. The solution is cooled to room temperature and 12.8 ml of triethylamine is added. (Solution B) The solution B is added dropwise with stirring to solution A (chilled at 0° C.) over 25 minutes. The mixture (containing solid) is stirred at room temperature overnight, filtered and the solid washed with tetrahydrofuran. The filtrate and wash are combined and the solvent removed. The residue is dissolved in ethyl acetate and the solution washed with 10% HCl, 10% NaHCO$_3$ and dried (MgSO$_4$). The solvent is removed to give 12.1 g of yellow solid. The solid is chromatographed on silica gel. Eluting with ethyl acetate removed impurities. The product fractions are obtained by eluting first with 5% CH$_3$OH in chloroform and then with 10% CH$_3$OH in chloroform. The product fractions are combined and the solvent removed. The residue in CHCl$_3$ is treated with activated carbon and the solution filtered through magnesium sulfate. The solvent is removed to give a gum. The gum is dissolved in ethyl acetate and the solvent removed to give 7.9 g of white crystals, mp 121.5°–122.5° C.; $[\alpha]_D^{26} -26° \pm 1$ (c, 1.03 CH$_3$OH).

REFERENCE EXAMPLE 80

(S)2-[(4-Morpholinocarbonyl)oxy]-3-cyclohexyl-propionic acid

A 2.19 g sample of (S)2-[(4-morpholinocarbonyl)oxy]-3-phenylpropionic acid and 1.1 g of rhodium on alumina in 35 ml of methanol is hydrogenated in a Parr hydrogenator under 30 pounds per square inch of hydrogen. The reaction mixture is filtered through diatomaceous earth, the filter pad washed with ethanol and the combined filtrate concentrated to give 2.51 g of an oil. The oil is purified by HPLC chromatography on silica gel with a Waters-Prep 500 instrument with chloroform containing 1% formic acid as eluent. The product fractions are collected, the solvent removed to give 1.18 g of oily crystals. This material is crystallized from chloroform-hexane to give 0.60 g white crystals, mp 75°–80° C.; $[\alpha]_D^{26} -7° \pm 1$ (c, 1.07, CH$_3$OH).

REFERENCE EXAMPLE 81

N-[(S)2-[(4-Morpholinocarbonyl)oxy]-3-cyclohexyl-propionyl]-L-leucine

A mixture of 0.30 g of (S)2-[(4-morpholinocarbonyl)oxy]-3-cyclohexylpropionic acid and 0.170 g of N,N-carbonyldiimidazole in 10 ml of tetrahydrofuran under argon is stirred for 2.5 hours. To the solution is added 0.240 g of methyl L-leucinate, hydrochloride and the mixture stirred overnight. The solvent is removed and the residue partitioned between ethyl acetate and water. The organic layer is separated, washed with 10% HCl, 10% NaHCO$_3$, dried (MgSO$_4$) and the solvent removed. The residue is dissolved in dichloromethane and chromatographed on silica gel with dichloromethane as eluent. The procuct is eluted with dichloromethane-ethyl acetate (7:3). The solvent is removed from product fractions to give 0.40 g of white crystals, mp softens 63°–65° C., melts 82°–83.5° C.; $[\alpha]_D^{26} -17° \pm 1$ (c, 1.00, CH$_3$OH).

To the preceding methyl ester (0.340 g) in 5 ml of methanol is added 44 mg of lithium hydroxide in 0.8 ml of water. After 2 hours at room temperature, 9 mg of lithium hydroxide is added and the solution stirred for 2.75 hours. To the solution is added 0.4 ml of 3N hydrochloric acid and the solvent removed. The residue is partitioned between dichloromethane and water. The organic layer is separated, dried (MgSO$_4$) and the solvent removed to give 0.29 g a clear foam; $[\alpha]_D^{26} -6° \pm 1$ (c, 1.00, CH$_3$OH). Anal. Calc for C$_{20}$H$_{34}$H$_2$O$_6$·½H$_2$O; 58.8; H, 8.7; M, 6.9. Found: C, 59.0; H, 8.7; N, 6.9.

EXAMPLE 1

N-[N-[(R)2-(Phenylmethyl)-3-(morpholinocarbonyl)propionyl]-L-leucyl]-(S)2-amino-3-cyclohexyl-(R)1-(2-thiazolyl)propan-1-ol To a mixture of 0.235 g of (R)-gamma-oxo-alpha-(phenylmethyl)-4-morpholinebutyric acid in 5 ml of dichloromethane, 0.12 ml of triethylamine and 0.36 g of benzotriazol-1-yloxytris(dimethylamino)phosphonium hexafluoro-phosphate (BOP) was added 0.274 g of N-(L-leucyl)-(S)2-amino-3-cyclohexyl-(R)1-(2-thiazolyl)-propan-1-ol. The mixture was stirred for 2 days and the solvent removed. The residue in 10 ml of ethyl acetate was washed with 1N hydrochloric acid sodium bicarbonate, brine and dried (MgSO$_4$). The solvent was removed and filtered through a thin pad of hydrous magnesium silicate. The pad was washed with ethyl acetate and the combined filtrates concentrated under vacuum to give 0.41 g of a glass. This glass was purified on thick layer silica gel plates to give 0.13 g of a foamy glass; $[\alpha]_D^{26} 37° \pm 1$ (c, 1.11, methanol).

EXAMPLE 2

N-[N-[(R)2-(Phenylmethyl)-3-(morpholinocarbonyl)-propionyl]-L-leucyl]-(S)2-amino-4-methyl-(R)1-(2-thiazolyl)pentan-1-ol To a mixture of 0.21 g of (R)-gamma-oxo-alpha-(phenylmethyl)-4-morpholinebutyric acid, 0.18 ml of triethylamine and 0.53 g of benzotriazol-1-yloxytris(dimethylamino)phosphonium hexafluorophosphate (BOP) in 2 ml of dichloromethane was added 0.21 g of N-L-leucyl]-(S)2-amino-4-methy-(R)1-(2-thiazolyl)pentan-1-ol. The mixture was stirred overnight, refluxed 2 hours and the solvent removed. The residue in 20 ml of ethyl acetate was washed twice with 5 ml each of 1N hydrochloric acid, 1M sodium bicarbonate and brine. The organic layer was dried (MgSO$_4$) and passed through a thin pad of hydrous magnesium silicate. The pad was washed with ethyl acetate and the combined filtrates concentrated under vacuum to give 0.4 g of a gum. This gum was purified on thick layer silica gel plates with 5% acetic acid in ethyl acetate as solvent to give 0.13 g of a glass; $[\alpha]_D^{26} -29° \pm 1$ (c, 0.854, methanol).

EXAMPLE 3

N-[N[(R)2-(Phenylmethyl)-3-(tert-butoxycarbonyl)propionyl]-L-leucyl]-(S)2-amino-4-methyl-(R)1-(2-thiazolyl)pentan-1-ol and N-[N-[(S)2-Phenylmethyl)-3-(tert-butoxycarbonyl)propionyl]-L-leucyl]-(S)2-amino-4-methyl-(R)1-(2-thiazolyl)pentan-1-ol To a mixture of 0.65 g of (R,S)2-(phenylmethyl)-butanedioic acid, 4-(1,1-dimethylethyl)ester, 0.37 ml of triethylamine and 1.08 g of benzotriazol-1-yloxytris(dimethylamino)phosphonium hexafluorophosphate (BOP) in 4 ml of dichloromethane was added 0.77 g of N-L-leucyl)-(S)2-amino-4-methyl-(R)1-(2-thiazolyl)-pentan-1-ol. The mixture was stirred overnight and the solvent removed under vacuum. The residue in 20 ml of ethyl acetate was washed twice with 5 ml each of 1N hydrochloric acid, 1M sodium bicarbonate and brine. The organic layer was dried (MgSO$_4$) and filtered through a thin pad of hydrous magnesium silicate. The pad was washed with ethyl acetate and the combined filtrates concentrated under vacuum to give 1.5 g of solid. The solid was chromatographed by HPLC on a Waters Prep 500 instrument (silica gel) with ethyl acetate-dichloromethane (4:6) as solvent. The first hold back volumes gave 0.34 g of N-[N-[(R)2-(phenylmethyl)-3-(tert-butoxycarbonyl)propionyl]-L-leucyl](S)2-amino-4-methyl-(R)1(2-thiazolyl)pentan-1-ol as a glass; $[\alpha]_D^{26} -28° \pm 1$ (c, 1.003, methanol) and the latter fractions gave 0.30 g of N-[N-[(S)2 (phenylmethyl)-3-(tert-butoxycarbonyl)propionyl]-L-leucyl]-(S)2-amino-4-methyl-(R)1-(2-thiazolyl)pentan-1-ol as crystals, mp 162°–163° C.; $[\alpha]_D^{26} -64° \pm 1$ (c, 1.030, methanol).

EXAMPLE 4

N-[N-[(R)2-(Phenylmethyl)-3-(tert-butylaminocarbonyl)propionyl]-L-histidyl]-(S)2-amino-4-methyl-(R)1-(2-thiazolyl)pentan-1-ol To 0.276 g of (R)alpha-[2-[(1,1-dimethylethyl)amino]2-oxoethyl]benzenepropionic acid in one ml of dichloromethane was added 0.014 ml of triethylamine and 0.465 g of benzotriazol-1-yloxytris(dimethylamino)phosphonium hexafluorophosphate (BOP). After 1.5 minutes, 0.337 g of N-(L-histidyl)-(S)2-amino-4-methyl-(R)1-(2-thiazolyl)pentan-1-ol was added and one ml of dichloromethane. The mixture was stirred 16 hours and the solvent removed. The residue in 5 ml of ethyl acetate was washed with 2 ml of water, three times with 2 ml of 1M sodium bicarbonate with 2 ml of brine. Cooling ($-10°$ C.) gave crystals which were filtered off. The filtrate was concentrated under vacuum to give 0.65 g of an oil. This oil was purified by thick layer chromatography on five $20\times20\times0.2$ cm silica gel plates developed with 20% methanol in dichloromethane containing 0.2% triethylamine. The band at RF 0.8 was separated, washed with methanol and the solvent removed. The residue in dichloromethane was filtered and the filtrate concentrated to give 0.3 g of a glass, mp 120°–130° C. $[\alpha]_D^{26} -8°\pm 1$(c, 1.042, methanol).

EXAMPLE 5

N-[N-[(R)2-(Phenylmethyl)-3-(tert-butylaminocarbonyl)propionyl]-L-leucyl]-(S)2-amino-4-methyl-(R)1-(2-thiazolyl)pentan-1-ol A mixture of 0.165 g of N,N-carbonyldiimidazole and 0.294 g of (R)alpha-[2-[(1,1-dimethylethyl)amino]-2-oxoethyl]benzenepropionic acid in 2 ml of dry tetrahydrofuran was stirred at room temperature for 2 hours. To the solution was added 0.32 g of N-[L-leucyl]-(S)2-amino-4-methyl-(R)1-(2-thiazolyl)pentan-1-ol in 2 ml of tetrahydrofuran and the mixture was stirred overnight. A solution of 0.15 g of (R)alpha[2-[(1,1-dimethylethyl)amino]-2-oxoethyl]benzenepropionic acid and 0.08 g of N,N-carbonyldiimidazole in one ml of tetrahydrofuran was prepared and this solution added to the reaction mixture. The mixture was stirred 2 hours and refluxed for one hour and the solvent removed. The residue in 20 ml of ethyl acetate was washed with three times each with 2 ml of 1N hydrochloric, 1M sodium bicarbonate and brine. The organic layer was dried (MgSO4) and filtered through a thin pad of hydrous magnesium silicate. The pad was washed with ethyl acetate and the filtrates combined The solvent was removed to give 0.48 g of solid. Trituration of this solid with ether gave crystals, mp 152°–153° C. Recrystallization from ether and isopropyl acetatediisopropylether gave 0.134 g of white crystals, mp 153°–154° C.; $[\alpha]_D^{26} -35°\pm 1$, (c, 0.649, methanol).

EXAMPLE 6

N-[N-[(R)2-(3,4,5-Trimethoxyphenylmethyl)-3-(morpholinocarbonyl)propionyl]-L-histidyl](S)2-amino-4-methyl-(R)1-(2-thiazolyl)pentan-1-ol To 0.88 g of (S,R)-gamma-oxo-alpha-(3,4,5-trimethoxyphenylmethyl)-4-morpholinebutyric acid in 2 ml of dichloromethane was added 0.33 ml of triethylamine and 1.46 g of benzotriazol-1-yloxytris(dimethylamino)phosphonium hexafluorophosphate. After stirring for 2 minutes, 0.68 g of N-(L-histidyl)-(S)2-amino-4-methyl-(R)1-(2-thiazolyl)pentan-1-ol in 2 ml of dichloromethane plus a few drops of N,N-dimethylformamide was added. The mixture was stirred at room temperature overnight and concentrated under vacuum to a thick oil. To this oil was added 20 ml of ethyl acetate. The mixture was filtered and the filtrate washed three times with 5 ml each of 1M sodium carbonate and 2N sodium carbonate, and brine. The organic layer was dried (MgSO4) and concentrated under vacuum to give 1.2 g of gum. This gum was chromatographed on silica gel with 5% methanol plus 1% triethylamine in dichloromethane as solvent on Water Prep 500 HPLC instrument. Cuts containing the first component eluted were combined and the solvent removed and the residue dried in an oven. The solid in ethyl acetate was washed with brine. The organic layer was separated and the solvent removed under vacuum. The residual glass was dried at 58° C. in a vacuum oven to give the product as a glass; $[\alpha]_D^{26} -41°\pm 1$ (c, 1.028, methanol).

EXAMPLE 7

N-[N-[(R)2-(Phenylmethyl)-3-(morpholinocarbonyl)propionyl]-L-histidyl]-(S)2-amino-3-cyclohexyl(R)1-(2-thiazolyl)propan-1-ol To 0.16 g of (R)-gamma-oxo-alpha-(phenylmethyl)-4-morpholinebutyric acid in one ml of dichloromethane was added 0.08 ml of triethylamine and 0.25 g of benzotriazol-1-yloxytris(dimethylamino)phosphonium hexafluorophosphate. After one minute 0.20 g of N-(L-histidyl)-(S)2-amino-3-cyclohexyl-(R)1-(2-thiazolyl)propan-1-ol in 2 ml of tetrahydrofuran was added. The mixture was stirred overnight and the solvent removed under vacuum. The residue in 10 ml of ethyl acetate was washed once with 2 ml of water, three times with 2 ml of 1M sodium bicarbonate and dried (MgSO4). The solution was filtered through a thin pad of hydrous magnesium silicate and the pad washed with ethyl acetate. The filtrates were combined and the solvent removed to give 0.24 g of product as a glass; $[\alpha]_D^{26} -11°\pm 1$ (c, 1.046, methanol).

EXAMPLE 8

N-[N-8 (R)2-(1-Naphthalenylmethyl)-3-(morpholinocarbonyl)propionyl]-L-histidyl]-(S)2-amino-3-cyclohexyl-(R)1-(2-pyridinyl)propan-1-ol To a solution of 0.15 g of (R)2-(1-naphthalenylmethyl)-3-(morpholinocarbonyl)propionic acid and 0.070 ml of triethylamine in 2 ml of dichloromethane was added 0.076 ml of diethylphosphoryl cyanide and the solution stirred under nitrogen for 4 hours. The solvent was removed under vacuum to give a gum. The gum in 5 ml of ethyl acetate was washed three times with one ml portions of 2M sodium carbonate and the organic layer dried (Na2SO4). The solvent was removed under reduced pressure to give 0.27 g of solid. This solid was chromatographed on five $20\times20\times0.2$ cm thick silica gel plates with dichloromethane-methanol-ammonium hydroxide (9:1.2:0.2) as solvent. The main band was separated and then eluted with methanol to give 0.18 g of the product of the Example as a glass; $[\alpha]_D^{26} +5°\pm 1$ (c, 1.025, methanol); FAB mass spectrum—703 (M +Na), 681 (M+H).

EXAMPLE 9

N-[N-[(R)2-(1-Naphthalenylmethyl)-3-(tert-butoxycarbonyl)propionyl]-L-histidyl]-(S)2-amino-3-cyclohexyl-1-(2-thiazolyl)propan-1-ol To a solution of 0.314 g of (R)2-(1-naphthalenylmethyl)-3-(tert-butoxycarbonyl)propionic acid in 0.5 ml of dichloromethane and 0.14 ml of triethylamine was added 0.44 g of benzotriazol-1-yloxytris(dimethylamino)phosphonium hexafluorophosphate. After one minute, 0.61 g of N-[N-im(benzyloxymethyl)-L-histidyl]-(S)2-amino-3-cyclohexyl)-(R)1-(2-thiazolyl)-1-

(tertbutyldimethylsilyloxy)propane in one ml of dichloromethane was added and the mixture stirred for 2 days. The solvent was removed under vacuum and the residue in 10 ml of ethyl acetate was washed three times each with 1N hydrochloric acid, 1M sodium hydroxide and with brine (one ml). The organic layer was dried (MgSO$_4$) and filtered through a thin pad of hydrous magnesium silicate. The pad was washed with ethyl acetate and the filtrates combined. The solvent was removed under reduced pressure to give 0.7 g of solid. To this solid in tetrahydrofuran is added tetra-n-butylammonium fluoride (1M in tetrahydrofuran) and the mixture stirred for 1.5 hours. The mixture is diluted with 10% sodium bicarbonate and ethyl acetate added. The organic layer is separated and washed with water and saturated sodium chloride (brine). The organic layer is dried and the solvent removed. The residue in methanol is shaken in a Parr hydrogenator with 10% palladium on carbon under a hydrogen atmosphere to give the product of the Example as a glass.

EXAMPLE 10

N-[N-[(R)2-(Phenylmethyl)-3-(tert-butoxycarbonyl)-propionyl]-L-leucyl]-(S)2-amino-3-cyclohexyl-(R)1-(2-thiazolyl)propan-1-ol To a solution of 0.080 g of (R)2-(phenylmethyl)-butanedioic acid, 4-(1,1-dimethylethyl)ester in 2 ml of dichloromethane was added 0.054 g of N,N-carbonyldiimidazole. After stirring at room temperature for 0.5 hours, a solution of 0.15 g of N-(L-leucyl)-(S)2-amino-cyclohexyl-(R)1-(2-thiazolyl)-1-(tert-butyldimethylsilyloxy)propane in 0.5 ml of dichloromethane was added. The mixture was stirred at room temperature for 24 hours and refluxed one day. The mixture was diluted with 15 ml of ethyl acetate and washed with two 5 ml portions each of 0.5N hydrochloric acid, saturated sodium bicarbonate and with 5 ml of brine. The organic layer was dried (Na$_2$SO$_4$) and the solvent removed to give 0.25 g of a foam. Chromatography on silica gel with ethyl acetate-hexane (1:4) gave 0.20 g of solid which was crystallized from hexane to give white crystals; $[\alpha]_D^{26} - 28° \pm 2$ (c, 0.594, CHCl$_3$).

A 0.14 g sample of the preceding compound in one ml of tetrahydrofuran and 0.22 ml of tetrabutylammonium fluoride (1.0M in tetrahydrofuran) was stirred at room temperature for one hour. The mixture was diluted with water (5 ml) and ethyl acetate (10 ml) and the organic layer separated and washed with 3 ml of 0.5N hydrochloric acid, 3 ml of saturated sodium carbonate and brine. The organic layer was dried (Na$_2$SO$_4$) and the solvent removed to give 0.13 g of gum. This gum was chromatographed on silica gel with ethyl acetate-hexane (1:2), then ethyl acetate-hexane (1:1) as solvent to give 0.090 g of solid. Washing with hexane gave 0.030 g of white solid; $[\alpha]_D^{26} - 10° \pm 2$ (c, 0.386, CHCl$_3$).

EXAMPLE 11

N-[N-(R)2-(Phenylmethyl)-3-(morpholinocarbonyl)-propionyl]-L-leucyl]-(S)2-amino-4-(methylthio)-(R)1-(2-thiazolyl)butan-1-ol To a solution of 0.28 g of (R)-gamma-oxo-alpha-(phenylmethyl)-4-morpholinebutyric acid in one ml of dichloromethane was added 0.014 ml of triethylamine and 0.465 g of benzotriazol-1-yloxotris(dimethylamino)-phosphonium hexafluorophosphate. After one minute 0.29 g of N-L-leucyl)-(S)2-amino-4-(methylthio)-(R)1-(2-thiazolyl)butan-1-ol in one ml of dichloromethane was added and the mixture stirred for three days. The solvent was removed and the residue dissolved in 10 ml of ethyl acetate. The solution was washed with three times each with 2 ml portions of 1N hydrochloric acid, 1M sodium bicarbonate, brine and dried (MgSO$_4$) The solvent was removed to give 0.33 g of solid. This solid was chromatographed on three 20×20×0.2cm thick layer silica gel plate with dichloromethane-methanol-water (10:5:1) as solvent. After development, the band containing product was washed with methanol and the solvent removed to give 0.23 g of an oil. This oil in 2 ml of dichloromethane was filtered and the filtrate concentrated and the solid dried to give 0.19 g of a glass; $[\alpha]_D^{26} - 26° \pm 1$ (c, 0.958, methanol).

EXAMPLE 12

N-[N-[(R)2-(1-Naphthalenylmethyl)-3-(tert-butoxy-carbonyl)propionyl]-L-leucyl]-(S)2-amino-4-methyl-(R)1-(2-thiazolyl)pentan-1-ol To a solution of 1.00 g (3.18 mmol) of (R)2-(1-naphthalenylmethyl)-3-(tert-butoxycarbonyl)propionic acid in 43 ml of dichloromethane was added 1.35 g (3.98 mmol) of N-(L-leucyl)-(S)2-amino-4-methyl-(R)1-(2-thiazolyl)pentan-1-ol hydrochloride and 1.16 ml (8.30 mmol) of triethylamine. The mixture was cooled to 0° C. and 0.665 ml (4.39 mmol) of diethyl cyanophosphonate was added. The mixture was allowed to warm to room temperature and stir for 16 hours. The mixture was concentrated under vacuum and the residue chromatographed on silica gel with ethyl acetate-hexane (1:1) as solvent to give 1.61 g of a white solid; $[\alpha]_D^{26} - 4°$ (c, 1.03, CHCl$_3$).

According to the procedure of Example 12, the following Examples were prepared.

TABLE II

| Example | Structure | Physical State | Rotation |
|---|---|---|---|
| 13 | 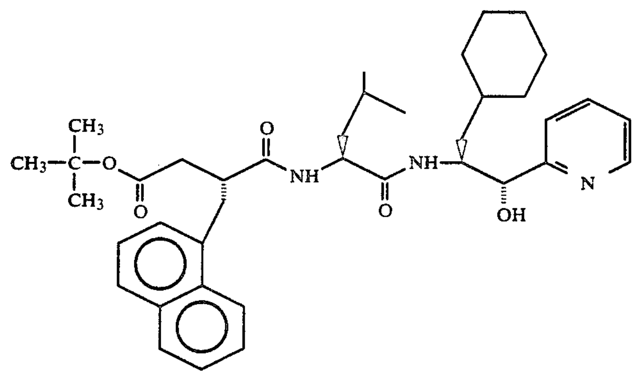 | white solid | $[\alpha]_D^{26}$ −14° (c, 0.958, methanol) |
| 14 | 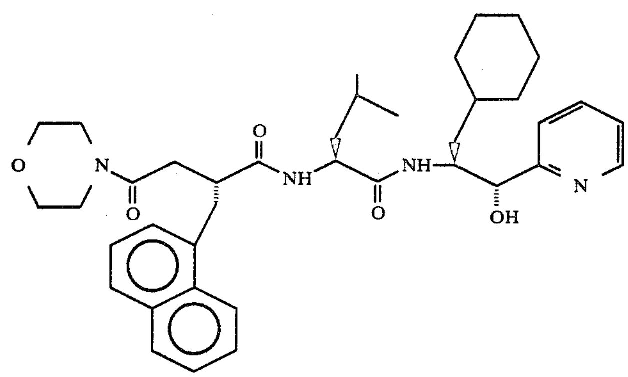 | white solid | $[\alpha]_D^{26}$ −27° (c, 0.93, CHCl₃) |
| 15 | 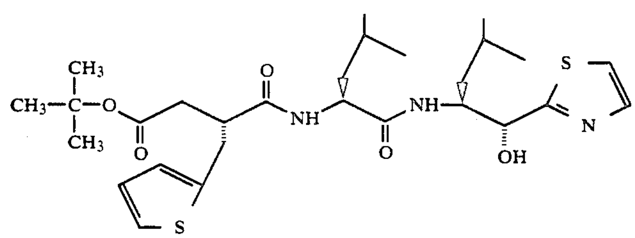 | foam | $[\alpha]_D^{26}$ −12° (c, 1.01, CHCl₃) |
| 16 | 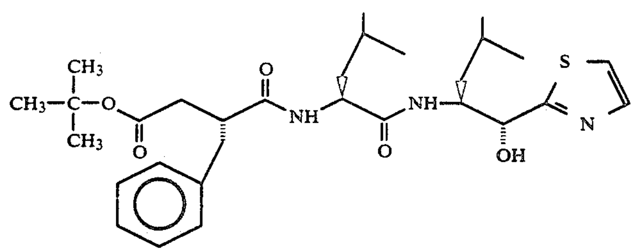 | glass | $[\alpha]_D^{26}$ −28° (c, 1.00, CH₃OH) |
| 17 | 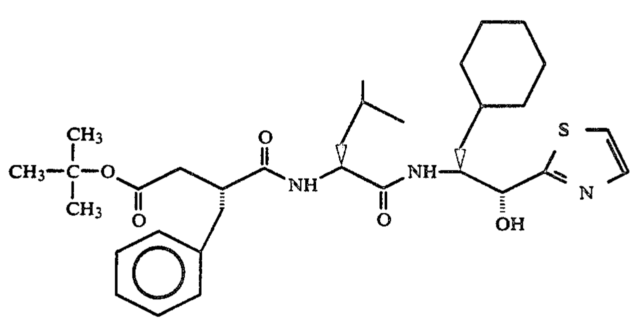 | white solid | $[\alpha]_D^{26}$ −10° (c, 0.386, CHCl₃) |

TABLE II-continued

| Example | Structure | Physical State | Rotation |
|---|---|---|---|
| 18 | 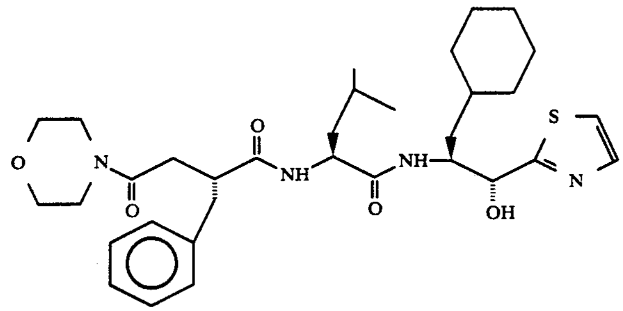 | foam | $[alpha]_D^{26}$ −37° (c, 1.11, CH$_3$OH) |
| 19 | 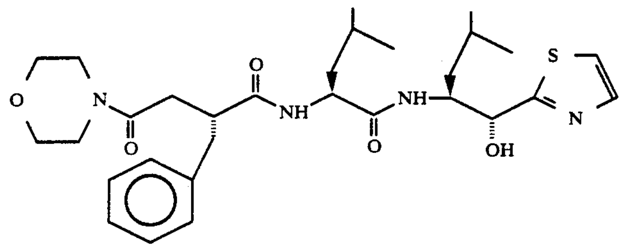 | glass | $[alpha]_D^{26}$ −29° (c, 0.854, CH$_3$OH) |
| 20 | 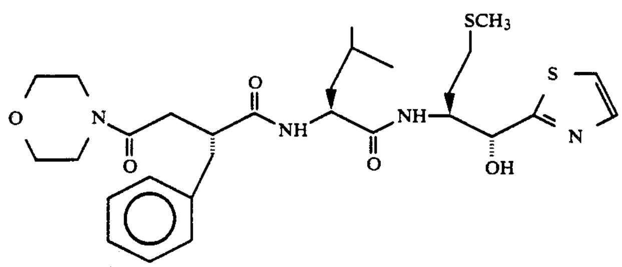 | glass | $[alpha]_D^{26}$ −26° (c, 0.958, CH$_3$OH) |

EXAMPLE 21

N-[N-[(R)2-(1-Naphthalenylmethyl)-3-(carboxy)propionyl]-L-leucyl]-(S)2-amino-4-methyl-(R)1-(2-thiazolyl)pentan-1-ol To a solution of 1.50 g of N-[N-(R)2-(1-naphthalenylmethyl)-3-(tert-butoxycarbonyl)propionyl]-L-leucyl]-(S)2-amino-4-methyl-(R)1-(2-thiazolyl)pentan-1-ol in 7.2 ml of dichloromethane, cooled to 0° C., was added dropwise 7.2 ml of trifluoroacetic acid. The solution was allowed to warm to room temperature and was stirred for one hour. The solvent was removed under vacuum and 30 ml of saturated sodium bicarbonate solution added to the residue The mixture was extracted with dichoromethane. The aqueous layer was acidified with 5% hydrochloric acid and extracted with dichloromethane. The extract was washed with brine, dried (MgSO$_4$) and the solvent removed. The residue was chromatographed over silica gel with chloroform-methanol-acetic acid (95:5:0.10) as eluent to give 1.30 g of a white solid.

EXAMPLE 22

N[N-[(R)2-(1-Naphthalenylmethyl)-3(phenethylcarbamoyl)propionyl]-L-leucyl-(S)2-amino-4-methyl-(R)1-(2-thiazolyl)pentan-1-ol To a solution of 0.050 g of N-[N-[(R)2-(1-naphthalenylmethyl)-3-(carboxy)propionyl]-L-leucyl]-(S)2-amino-4-methyl-(R)1-(2-thiazolyl)pentan-1-ol in one ml of dichloromethane was added 14.2 μL (0.0113 mmol) of phenethylamine and 18.9 μL (0.136 mmol) of triethylamine and then 18.7 μL (0.124 mmol) of diethyl cyanophosphonate was added. The mixture was allowed to warm to room temperature and stir for 18 hours. The mixture was concentrated under vacuum and the residue purified by preparative thin layer chromatography with ethyl acetate as solvent to give 0.045 g of white solid; $[\alpha]_D^{26}$ −19° (c, 0.95, CHCl$_3$).

The above procedure of Example 22 is used to prepare the following Examples.

TABLE III
STRUCTURE
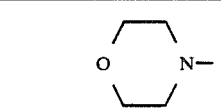
| Example | R = | Physical State | Rotation |
|---|---|---|---|
| 23 | 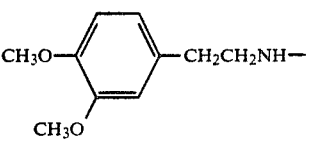 | glass | [alpha]$_D^{26}$ −18° (c, 0.66, CHCl$_3$) |
| 24 | 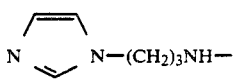 | glass | [alpha]$_D^{26}$ −18° (c, 1.00, CHCl$_3$) |
| 25 | 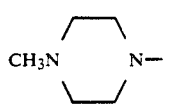 | glass | |
| 26 |  | glass | [alpha]$_D^{26}$ −22° (c, 0.33, CHCl$_3$) |
| 27 | (CH$_3$O)$_2$CHCH$_2$NH— | glass | [alpha]$_D^{26}$ −13° (c, 0.96, CHCl$_3$) |
| 28 | 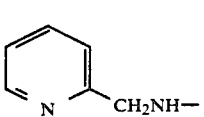 | solid | [alpha]$_D^{26}$ −25° (c, 1.03, CHCl$_3$) |
| 29 | 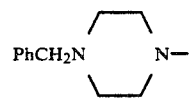 | solid | [alpha]$_D^{26}$ −26° (c, 1.04, CHCl$_3$) |
| 30 | 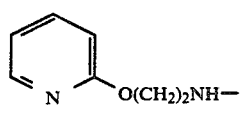 | solid | [alpha]$_D^{26}$ −23° (c, 1.04, CHCl$_3$) |
| 31 | 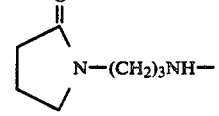 | solid | [alpha]$_D^{26}$ −17° (c, 1.09, CHCl$_3$) |
| 32 | 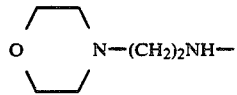 | solid | [alpha]$_D^{26}$ −11° (c, 1.08, CHCl$_3$) |

TABLE III-continued

STRUCTURE

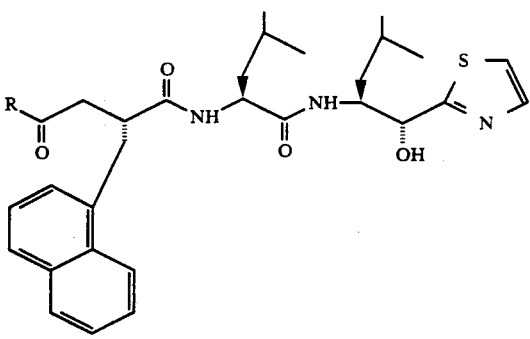

| Example | R = | Physical State | Rotation |
|---|---|---|---|
| 33 | 3-pyridyl-CH$_2$NH— | solid | $[alpha]_D^{26}$ −26° (c, 1.10, CHCl$_3$) |
| 34 | (1-methylpyrrol-2-yl)-(CH$_2$)$_2$NH— | solid | $[alpha]_D^{26}$ −19° (c, 1.09, CHCl$_3$) |
| 35 | morpholino-N(CH$_2$)$_3$NH— | solid | $[alpha]_D^{26}$ −11° (c, 1.03, CHCl$_3$) |
| 36 | 2-pyridyl-(CH$_2$)$_2$NH— | solid | $[alpha]_D^{26}$ −21° (c, 0.936, CHCl$_3$) |
| 37 | piperidino-N(CH$_2$)$_2$NH— | solid | $[alpha]_D^{26}$ −14° (c, 1.10, CHCl$_3$) |
| 38 | pyrrolidino-N(CH$_2$)$_2$NH— | solid | $[alpha]_D^{26}$ −15° (c, 0.938, CHCl$_3$) |
| 39 | 2-pyridyl-N(CH$_2$)$_4$NH— | solid | $[alpha]_D^{26}$ −19° (c, 0.981, CHCl$_3$) |

EXAMPLE 40

N-[N-[(R)2-(1-Naphthalenylmethyl)-3-(morpholinocarbonyl)propionyl]-L-leucyl]-(S)2-amino-3-cyclohexyl-(R)1-(2-pyridinyl)propan-1-ol To a solution of a 0.056 g of (R)-beta(1-naphthalenylmethyl-gamma-oxo-4-morpholinebutanoic acid in 2.0 ml of dichloromethane was added 0.074 g of N-(L-leucyl)-(S)2-amino-3-cyclohexyl-(R)1-(2-pyridinyl)propan-1-ol and 0.036 ml of triethylamine. To the mixture was added 0.36 ml of diethyl cyanophosphate and the mixture was stirred at room temperature for 16 hours. The mixture was concentrated under vacuum and the residue chromatographed on preparative silica gel plates with chloroform-methanol (95:5) as solvent to give 0.102 g of while solid; $[\alpha]_D^{26}$−27° (c, 0.93, CHCl$_3$).

According to the procedure of Example 22, and following Examples were prepared.

TABLE IV

| Example | Structure | Physical State | Rotation |
|---------|-----------|----------------|----------|
| 41 | 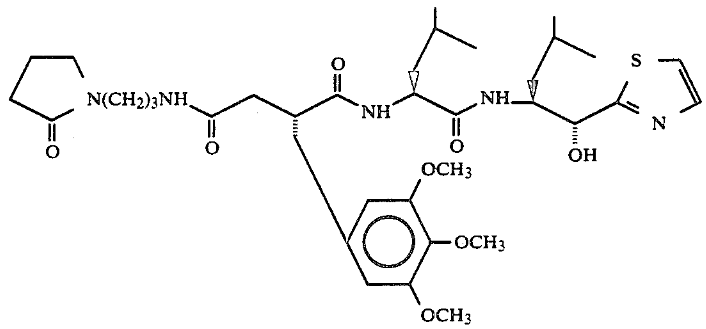 | solid | [alpha]$_D^{26}$ −20° ± 2 (c, 0.530, CHCl$_3$) |
| 42 | 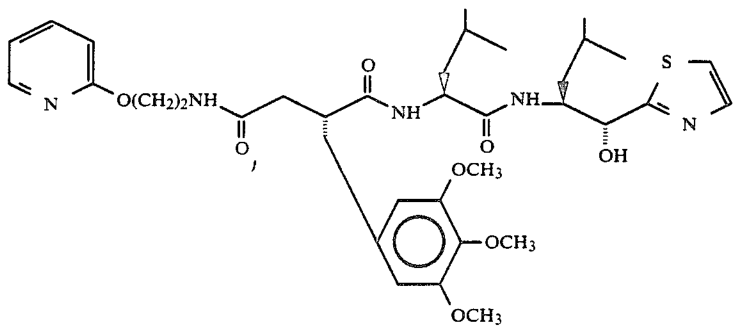 | solid | [alpha]$_D^{26}$ −25° ± 2 (c, 0.459, CHCl$_3$) |
| 43 | 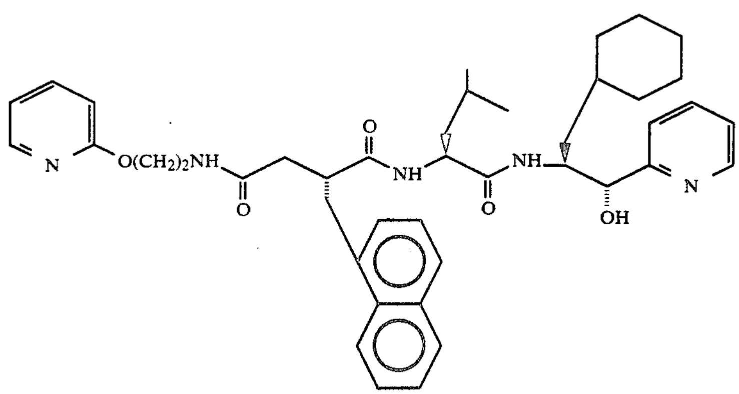 | solid | [alpha]$_D^{26}$ −28° ± 2 (c, 0.48, CHCl$_3$) |
| 44 | 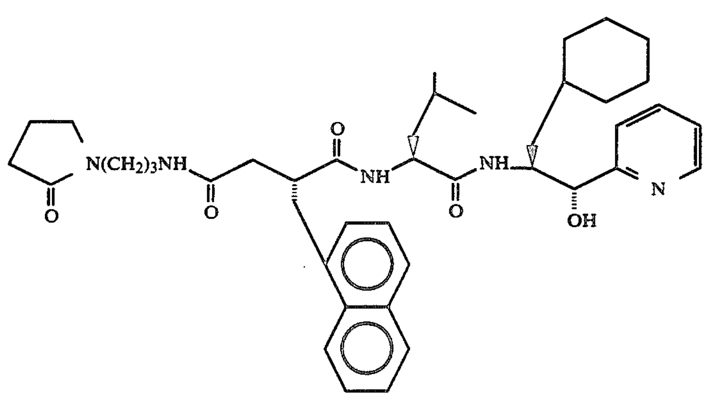 | solid | [alpha]$_D^{26}$ −26° ± 1 (c, 0.653, CHCl$_3$) |

TABLE IV-continued

| Example | Structure | Physical State | Rotation |
|---|---|---|---|
| 45 | 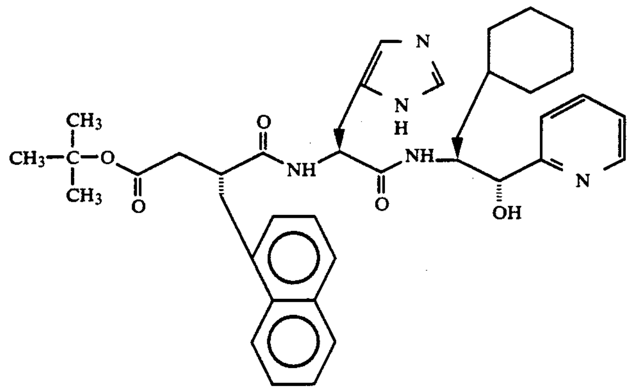 | solid | [alpha]$_D^{26}$ +13° ± 1 (c, 0.876, CHCl$_3$) |
| 46 | 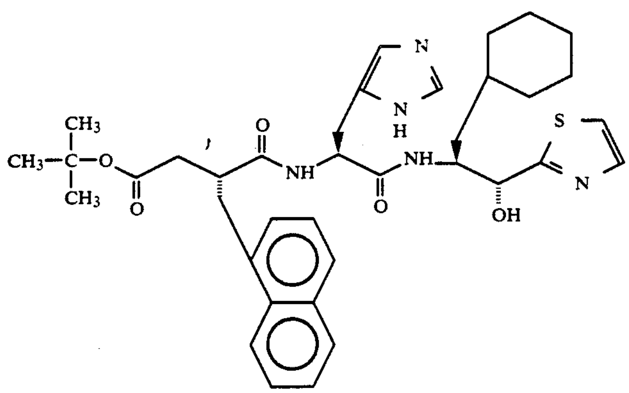 | solid | [alpha]$_D^{26}$ +21° ± 1 (c, 0.905, CHCl$_3$) |
| 47 | 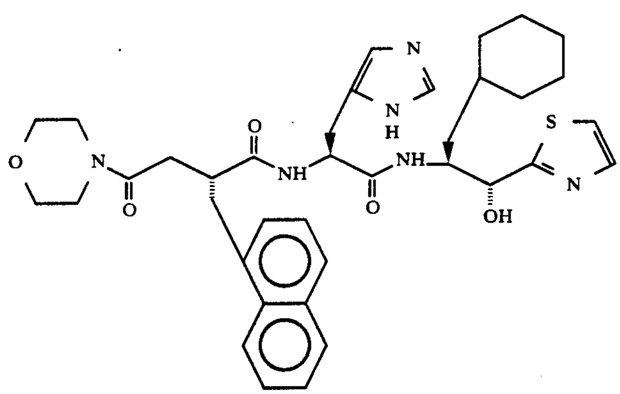 | solid | [alpha]$_D^{26}$ +17° ± 2 (c, 0.585, CHCl$_3$) |
| 48 | 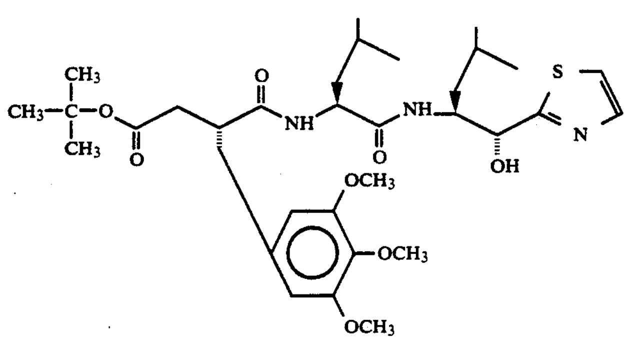 | solid | [alpha]$_D^{26}$ −8° ± 1 (c, 0.992, CHCl$_3$) |

TABLE IV-continued

| Example | Structure | Physical State | Rotation |
|---|---|---|---|
| 49 | 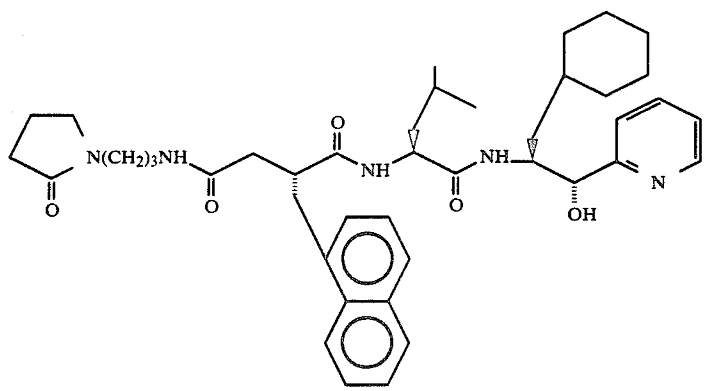 | solid | [alpha]$_D^{26}$ −26° ± 1 (c, 0.653, CHCl$_3$) |
| 50 | 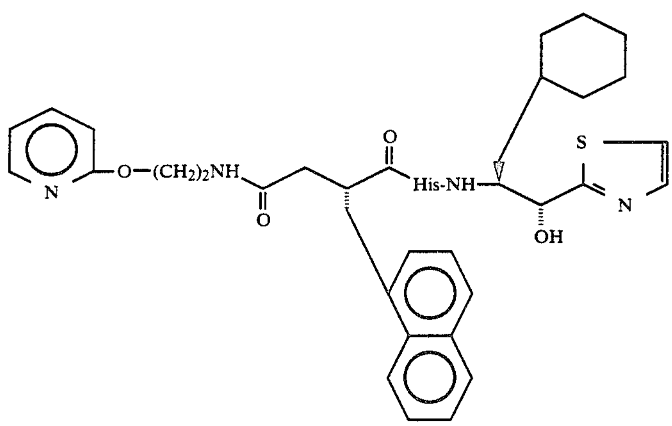 | | [alpha]$^{26}$ −23° ± 9 (c, 0.114, (CHCl$_3$)) |

EXAMPLE 51

N,[N-[(R)2-(1-Naphthalenylmethyl)-3-(carboxy)propionyl]-(S)2-amino-3-cyclohexyl-(R)1-(2-pyridinyl)propan-1-ol As described for Example 40, (R)2-(1-naphthalenylmethyl)-3-(tert-butoxycarbonyl)propionic acid was coupled to N-L-leucyl)-(S)2-amino-3-cyclohexyl-(R)1-(2-pyridinyl)propan-1-ol to give [after purification on silica gel plates with ethyl acetate-hexane (1:1) as solvent]N-[N-[(R)2-(1-naphthalenylmethyl)-3-(tert-butoxycarbonyl)propionyl]-L-leucyl]-(S)2-amino-3-cyclohexyl-(R)1-(2-pyridinyl)propan-1-ol as a white solid; [α]$_D^{26}$−14° (c, 1.059, CHCl$_3$). This compound was stirred with dichloromethane-trifluoroacetic acid (1:1) at room temperature as described for Example 21 to give a solid. Chromatography on preparative silica gel plates gave the product as a white solid; [α]$_D^{26}$−11°(c, 1.059, CHCl$_3$)

EXAMPLE 52

N,[N-[(R)2-(3,4,5-Trimethoxybenzyl)-3-(carboxy)-propionyl]-L-leucyl]-(S)2-amino-4-methyl-(R)1-(2-thiazolyl)pentan-1-ol To a solution of 0.25 g of N-[N-[(R)2-(3,4,5- trimethoxybenzyl)-3-(tert-butoxycarbonyl)propionyl -L-leucyl]-(S)2-amino-4-methyl-(R)1-(2-thiazolyl)pen 1-ol in 1.1 ml of dichloromethane cooled to 0° C. was added 1.1 ml of trifluoroacetic acid. The solution was stirred at room temperature for one hour and the solvent removed under vacuum. The residue was dissolved in 10 ml of dichloromethane and poured into saturated sodium bicarbonate solution. The organic layer was removed and the aqueous layer acidified with 5% hydrochloric acid. The aqueous layer was extracted with dichloromethane, dried (Na and the solvent removed to give 0.167 g of solid; [α]$_D^{26}$+5°±1 (c, 0.812, CHCl$_3$).

EXAMPLE 53

N,[N-[(R)2-(Phenylmethyl)-3-(tert-butylamino-carbonyl)propionyl]-L-histidyl])S)2-amino-3-cyclohexyl-(R)1-(2-thiazolyl)propan-1-ol To a mixture of 0.22 g of (R)-alpha-[2-[(1,1-dimethylethyl)amino]-2-oxoethyl]benzenepropionic acid and 0.12 ml of triethylamine in one ml of dichloromethane was added 0.38 g of benzotriazol-1-yloxy-tris(dimethylamino)phosphonium hexafluorophosphate (BOP). After 2 minutes was added 0.35 g of N-(L-histidyl)-(S)2-amino-3-cyclohexyl-(R)1-(2-thiazolyl)-1-[(tert-butyldimethyl)silyloxy]propane and the mixture was stirred overnight at room temperature. The mixture was cooled to 0° C., 2 ml of tetra-n-butylammonium fluoride in tetrahydrofuran (1M) added and the mixture refluxed 4 hours. An additional 2 ml of tetra-n-butylammonium fluoride in tetrahydrofuran (1M) was added and the solution refluxed overnight. The solvent was removed under vacuum and the residue stirred with 5 acetonitrile and 0.50 ml of 40 hydrofluoric acid for 4 hours. The solvent was removed under vacuum and the residue diluted with 5 ml of water and made basic with 10 ml of 2M sodium carbonate. The mixture was extracted with two 20 ml portions of ethyl acetate. The extract was washed with 2M sodium carbonate solution, brine and dried (Na$_2$SO$_4$). This gum was dissolved in 2.8 ml of acetonitrile and 1.2 ml of 40% hydrofluoric acid, stirred 1.5 hours and diluted with 10 ml of water. The mixture was filtered and the filtrate made basic with concentrated ammonium hydroxide. The mixture was extracted with dichloromethane and the extract concentrated under vacuum. The residue was purified by thick layer chromatography on silica gel plates with dichloromethane-methanol-concentrated ammonium hydroxide (9:1.2:0.2) as solvent to give 0.34 g of solid; $[\alpha]_D^{26} -18° \pm 1$ (c, 0.898, CH$_3$OH).

EXAMPLE 54

N-[N-[(R)2-(1-Naphthalenylmethyl)-3-(morpholinocarbonyl)propionyl]-L-histidyl]-(S)-2-amino-3-cyclohexyl-(R)1-(2-thienyl)propan-1-ol To 0.19 g of (R)2-(1-naphthalenylmethyl)-3-morpholinocarbonyl)propionic acid in 1 ml of dichloromethane was added 0.081 ml of triethylamine and 0.26 g of benzotriazol-1-gloxytris(dimethylamino)phosphonium hexafluorophosphate. After 1 minute, 0.22 g of N-(L-histidyl)-(S)2-amino-3-cyclohexyl-(R)1-(2-thienyl)propan-1-ol in 1 ml of dichloromethane was added. The mixture was stirred overnight at room temperature and concentrated under vacuum. The residue in 5 ml of ethyl acetate was washed three times with 1 ml of 1M sodium carbonate and with brine. The organic layer was dried (Na$_2$SO$_4$) and the solvent removed. The residue (0.7 g) was chromatographed on four 20×20×0.2 cm silica gel plates with dichloromethane-methanol-ammonium hydroxide (9:1.2:0.2) as solvent. The product band was extracted with methanol containing 5% ammonium hydroxide and the extract concentrated under vacuum to give 0.10 g of a glass; $[\alpha]_D^{26} -7° \pm 1$(c, 1.057,CH$_3$OH).

EXAMPLE 55

N-[N-[[(S)2-(4-Morpholinocarbonyl)oxy]-3-phenylpropionyl]-L-leucyl]-(S)2-amino-3-cyclohexyl-(R)1-(2-pyridinyl)propan-1-ol To a solution of 6.81 g of (S)2-[(4-morpholinocarbonyl)oxy]-3-phenylpropionic acid in 175 ml of dry tetrahydrofuran was added 3.95 g of N,N-carbonyldiimidazole. The solution was stirred at room temperature for 2.5 hours and 5.55 g of L-leucine methyl ester hydrochloride added. The mixture was stirred at room temperature overnight, warmed briefly and filtered. The filtrate was concentrated to dryness and the residue dissolved in 100 ml of dichloromethane. The solution was washed with 50 ml of 10% hydrochloric acid, 50 ml of 10% sodium bicarbonate solution and dried (MgSO$_4$). The solvent was removed under vacuum to give 8.4 g of a pale yellow gum. The gum in dichloromethane was chromatographed on a pad of hydrous magnesium silicate in a sintered glass funnel. The pad was washed with 2 liters of dichloromethane and 3 liters of dichloromethane-ethyl acetate (9:1) with 1 liter fractions collected. Cuts 2-5 were combined, dried (MgSO$_4$) and the solvent removed under vacuum to give 7.62 g of N-[[(S)2-(4-morpholinocarbonyl)oxy]-3-phenylpropionyl]-L-leucine methyl ester as a pale yellow voscous oil $[\alpha]_D^{26} -30° \pm 1$ (c, 1.025, CH$_3$OH). To the preceding compound (7.50 g) in 55 ml of methanol was added 0.855 g of lithium hydroxide monohydrate in 10 ml of water. The solution was stirred at room temperature for 2.25 hours and 6 ml of 3N hydrochloric acid added. The solvent was removed and the residue partitioned beetween water and ethyl acetate. The organic layer was removed and the aqueous layer extracted twice with ethyl acetate. The organic layer and extracts were combined, dried (MgSO$_4$) and the solvent removed and residue pumped under high vaccum to give 6.67 g of N-[[(S)2-(4-morpholinocarbonyl)oxy]-3-phenylpropionyl]-L-leucine as a white foam; $[\alpha]_D^{26} -21° \pm 1$ (c, 1.239, CH$_3$OH).

To a solution of 0.364 g of imidazole in 7 ml of dichloromethane under argon was added 0.226 g of phenyl dichlorophosphate and the mixture stirred at room temperature for 0.5 hour. The mixture was cooled to −15° C. and 0.419 of N-[[(S)-2-(4-morpholinocarbonyl)-oxy]-3-phenylpropionyl]-L-leucine added. The mixture was stirred at −15° C. for 1 hour; 0.200 g of (S)2-amino-3-cyclohexyl-(R)1-(2-pyridinyl)propan-1-ol was added and the mixture stirred at −15° C. to −18° C. for 18 hours and at 0° C. for 5 hours. To the cold mixture was added 10% sodium bicarbonate solution and the organic layer separated. The aqueous layer was extracted with dichloromethane and the organic layer and extracts combined and dried (MgSO$_4$). The solvent was removed under vacuum to give 0.57 g of pale yellow gum. The gum was chromatographed over silica (gradient elution) with solvent dichloromethane-ethyl acetate (2:3) to ethyl acetate. Concentration of fractions containing product gave 0.18 g of the product as a white foam: $[\alpha]_D^{26} -25° \pm 1$ (c, 1.016, CH$_3$OH).

EXAMPLE 56

N-[N-[[(S)2-(4-Morpholinocarbonyl)oxy]]-3-phenylpropionyl]-L-leucyl]-(S)2-amino-3-cyclohexyl-(R)1-(2-thienyl)propan-1-ol To a solution of 0.500 g of N-[[(S)2-(4-morpholinocarbonyl)oxy]-3-phenylpropionyl]-L-leucine in 10 ml of dichloromethane under argon was added 0.129 g of triethylamine and 0.566 g of benzotriazol-1-yloxytris(dimethylamino)phosphonium hexafluorophosphate (BOP) After stirring 1 minute, 0.277 g of (S)2-amino-3-cyclohexyl-(R)1-(2-thienyl)propan-1-ol was added and the mixture was stirred overnight. The solvent was removed and the residue dissolved in ethyl acetate. The solution was washed with 10% hydrochloric acid, 2M sodium carbonate, water and dried (MgSO$_4$). The solvent was removed under vacuum to give 0.70 g of a white foam. Chromatography on silica gel with dichloromethane-ethyl acetate (3:1) and then with dichloromethane-ethyl acetate (7:3) gave 0.490 g of product as a white foam: $[\alpha]_D^{26} -42° \pm 1$ (c, 1.056, CH$_3$OH).

EXAMPLE 57

N-[N-[[(S)2-(4-thiomorpholinocarbonyl)oxy]-3-phenylpropionyl]-L-leucyl]-(S)2-amino-3-cyclohexyl-(R)1-(2-thienyl)propan-1-ol To 7.22 g of L-phenyllactic acid methyl ester under argon was added 330 ml of 12.5% phosgene in toluene (10.5 ml) with rapid stirring. To the solution was added dropwise 0.766 ml of N,N-dimethylformamide and the mixture stirred overnight. The mixture was concentrated to dryness under vacuum and toluene added (twice) and removed. The residue was pumped under high vacuum, flushed with argon and dissolved in 150 ml of dry dichloromethane. The solution was chilled to 0° C. and 12 g (11 ml) of 4-thiomorpholine added dropwise over 10 minutes. The mixture was stirred at 0° C. for three hours and then stored at 4° C. overnight. Dichloromethane (100 ml) and 0.5N hydrochloric acid (50 ml) were added, the organic layer separated, and the aqueous layer extracted with 50 ml of dichloromethane. The organic layer and extract were combined, washed with 50 ml of 10% sodium bicarbonate and dried (MgSO$_4$) The solvent was removed and the residue chromatographed by HPLC on silica gel with a Waters-Prep 500 instrument with chloroform-hexane (8:1) as solvent. Fractions containing product were combined and the solvent removed to give 3.68 g of (S)2-[(4-thiomorpholinocarbonyl)oxy]-3-phenylpropionic acid methyl ester as a pale yellow oil: $[\alpha]_D^{26} -27° \pm 1$ (c, 1.019, CH$_3$OH). To the preceding compound (3.55 g) in 40 ml of methanol was added a solution of 0.531 g of lithium hydroxide monohydrate in 5 ml of water. The mixture was stirred 3 hours and quenched with 4 ml of 3N hydrochloric acid. The solvent was removed under vacuum and the residue partitioned between water (20 ml) and dichloromethane (20 ml). The organic layer was separated and the aqueous layer and extracts were combined, dried (MgSO$_4$) and the solvent removed under vacuum to give 2.76 g of (S)2-(4-thiomorpholinocarbonyl)oxy]-3-phenylpropionic acid a colorless gum: $[\alpha]_D^{26} -36° \pm 1$ (c, 0.707, CH$_3$OH). To the preceding compound (2.76 g) in 70 ml of dry tetrahydrofuran under argon was added 1.48 g of N,N-carbonyldiimidazole. The solution was stirred for 2.5 hours and 2.08 g of L-leucine methyl ester hydrochloride added. The mixture was stirred overnight at room temperature, filtered and the filtrate concentrated under vacuum. The residue was dissolved in 50 ml of dichloromethane and the solution washed with 25 ml of 10% hydrochloric acid, 10% sodium bicarbonate and dried (MgSO$_4$). The solvent was removed to give 3.71 g of viscous oil. This oil was chromatographed on silica gel with dichloromethane as eluent and then dichloromethane-ethyl acetate (9:1) as eluent. The fractions containing product were combined, and the solvent removed to give 3.17 g of N-[[(S)2-(4-thiomorpholinocarbonyl)oxy]-3-phenylpropionyl]-L-leucine methyl ester as a viscous yellow oil: $[\alpha]_D^{26} -37° \pm 1$ (c, 1.085, CH$_3$OH). To the preceding compound (3.07 g) in 22 ml of methanol was added a solution of 0.336 g of lithium hydroxide monohydrate in 5 ml of water. After stirring 2.5 hours at room temperature, an additional 0.112 g of lithium hydroxide monohydrate in 1.5 ml of water was added. The mixture was stirred for 0.5 hour, quenched with 3.7 ml of 3N-hydrochloric acid and the solvent removed. The residue was partitioned between water and ethyl acetate. The organic layer was separated and the aqueous layer extracted twice with ethyl acetate. The organic layer and extracts were combined, dried (MgSO$_4$) and the solvent removed. The residue was pumped under high vacuum to give 3.01 g of N-[[(S)2-(4-thiomorpholinocarbonyl)oxy]-3-phenylpropionyl]-L-leucine as a white glass; $[\alpha]_D^{26} -28° \pm 1$ (c, 1.177, CH$_3$OH).

To the preceding compound (0.500 g) in 10 ml of dichloromethane was added 0.124 g of triethylamine and 0.544 g of benzotriazol-1-yloxytris(dimethylamino)phosphonium hexafluorophosphate (BOP). After 1 minute, 0.268 g of (S)2-amino-3-cyclohexyl-(R)1-(2-thienyl)propan-1-ol was added and the mixture was stirred at room temperature overnight. The solvent was removed under vacuum and the residue in ethyl acetate was washed with 2M sodium carbonate and with water. The organic layer was dried (MgSO$_4$) and the solvent removed to give 0.81 g of a glass. The glass was dissolved in dichloromethane-ethyl acetate (9:1) and filtered through a thin pad of hydrous magnesium silicate. The pad was washed with dichloromethane-ethyl acetate (9:1) and the combined filtrate concentrated under vacuum to give 0.610 g of the product as a white glass; $[\alpha]_D^{26} -44° \pm 1$ (c, 1.101, CH$_3$OH).

EXAMPLE 58

N-[N[[(S)2-(4-Thiomorpholinocarbonyl)oxy]-3-phenylpropionyl]-L-leucyl]-(S)2-amino-3-cyclohexyl-(R)1-(2-pyridinyl)propan-1-ol To a solution of 0.500 g of N-[[(S)2-(4-thiomorpholinocarbonyl)oxy]-3-phenylpropionyl]-L-leucine in 10 ml of dichloromethane under argon was added 0.124 g of triethylamine and 0.544 g of benzotriazol-1-yloxytris(dimethylamino)phosphonium hexafluorophosphate (BOP). After 1 minute, 0.262 g of (S)2-amino-3-cyclohexyl-(R)1-(2-pyridinyl)propan-1-ol was added and the mixture stirred overnight and concentrated to dryness. The residue was dissolved in ethyl acetate and the solution washed with 2M sodium carbonate, water, dried (MgSO$_4$) and the solvent removed to give 0.72 g of a clear foam. Chromatography on silica gel with dichloromethane as eluent and then dichloromethane-ethyl acetate (1:1) as eluent gave 0.480 g of product as a white foam: $[\alpha]_D^{26} -31° \pm 1$ (c, 1.104, CH$_3$OH).

EXAMPLE 59

N-[N-[[(S)2-[(4-Morpholinocarbonyl)oxy]-3-phenylpropionyl]-L-leucyl]-(S)2-amino-3-cyclohexyl-(R)1-(2-furanyl)propan-1-ol As described for Example 56, 0.500 g of N-[[(S)2-[(4-morpholinocarbonyl)oxy]-3-phenylpropionleucine was reacted with 0.258 g of (S)2-amino-3-cyclohexyl-(R)1-(2-furanyl)propan-1-ol in 10 ml dichloromethane to give 0.50 g of product as a white foam: $[\alpha]_D^{26} -33° \pm 1$ (c, 1.035, CH$_3$OH).

EXAMPLE 60

N-[N-[[(S)2-[(4-Thiomorpholinocarbonyl)oxy]-3-phenylpropionyl]-L-leucyl]-(S)2-amino-3-cyclohexyl-(R)1-(2-furanyl)propan-1-ol As described for Example 57, 0.500 g of N-[[(S)2-(4-thiomorpholinocarbonyl)oxy]-3-phenylpropionyl]-L-leucine was reacted with 0.250 g of (S)2-aminocyclohexyl-(R)1-(2-furanyl)propan-1-ol in 10 ml of dichloromethane to give 0.44 g of product as a white glass: $[\alpha]_D^{26} -34° \pm 1$ (c, 1.007, CH$_3$OH).

EXAMPLE 61

N-[N-[(R)2-(1-Naphthalenylmethyl)-3-(4-morpholinocarbonyl)propionyl]-L-leucyl]-(S)2-amino-3-cyclohexyl-(R)1-(2-furanyl)propan-1-ol To a solution of 1.4 g of imidazole in 18 ml of dichloromethane was added 0.90 ml of phenyl dichlorophosphate in 6 ml of dichloromethane. The mixture was stirred for 20 minutes, cooled to 0° C. and a solution of 0.60 g of imidazole, 2.4 ml of N,N-dimethylformamide, and 1.60 g of N$^\alpha$-[(benzyloxy)car-L-leucine in 6 ml of tetrahydrofuran added. The mixture was stirred at 0° C. for 40 minutes and then 1.30 g of (S)2-amino-3-cyclohexyl-(R)1-(2-furanyl)propan-1-ol added. The mixture was stirred at 0° C.-25° C. (ice bath allowed to melt) overnight and the solvent removed. The residue was dissolved in 20 ml of ethyl acetate and washed with water, 2N-citric acid, sodium bicarbonate solution and dried (MgSO$_4$). The solution was filtered through a thin pad of hydrous magnesium silicate (pad washed with several volumes of ethyl acetate). The filtrate was evaporated under vacuum to give 2.3 g of N-[N-(benzyloxy)-carbonyl-L-leucyl]-(S)2-amino-3-cyclohexyl-(R)1-(2-furanyl)propan-1-ol as an oil: R$_F$0.31 on thin layer chromatography (silica gel) with hexane-ethyl acetate (3:1) as solvent. The preceding compound (1.85 g) and 1.0 g of ammonium formate in 24 ml of methanol under nitrogen was warmed on a steam bath and then the solution chilled to 0° C. under nitrogen. To this mixture (without stirring) was added (by pipette) 0.96 g of 10% palladium on carbon suspended in 5 ml of ethanol. The mixture was chilled at 0° C. and stirred for 1 hour. Diatomaceous earth was added and the mixture filtered and the pad of diatomaceous earth washed with methanol. The filtrate was evaporated to dryness and the residue partitioned between ammonium hydroxide and dichloromethane. The organic layer was separated, dried (MgSO$_4$) and the solvent removed to give 1.24 g of gum. Crystallization from 5 ml of diisopropyl ether gave 0.74 g N-(L-leucyl)-(S)2-amino-3-cyclohexyl-(R)1-(2-furanyl)propan-1-ol as colorless needles, m.p. 83°-84° C. [60 ]$_D^{26}$−17°±1 (c, 1.031, CH$_3$OH).

To a solution of 0.25 g of (R)2-(1-naphthalenylmethyl)-3-(4-morpholinocarbonyl)propionic acid and 0.11 ml of triethylamine in 2 ml of dichloromethane was added 0.34 g of benzotriazol-1-yloxytris(dimethylamino)phosphonium hexafluorophosphate (BOP). To this solution was added 0.25 g of N-(L)-leucyl)-(S)2-amino-3-cyclohexyl-(R)1-(2-furanyl)propan-1-ol in 2 ml of dichloromethane. The mixture was stirred overnight and concentrated under vacuum. The residue was dissolved in 10 ml of ethyl acetate and the solution washed with 1N hydrochloric acid, sodium bicarbonate solution and three times with 2 ml of saturated sodium carbonate. The organic layer was dried (MgSO$_4$) and the solvent removed. The residue was chromatographed on silica gel with ethyl acetate as eluent to give 0.30 g of solid, m.p. 83°-87° C., [α]$_D^{26}$−20°±1 (c, 1.007, CH$_3$OH).

EXAMPLE 62

N-[N-[[(S)2-(4-Morpholinocarbonyl)oxy]-3-phenylpropionyl]-L-leucyl]-(S)2-amino-3-cyclohexyl-(R)1-(2-thiazolyl)propan-1-ol A solution of 0.312 g of (S)2-[(4-morpholino-carbonyl)oxy]-3-phenylpropionic acid and 0.181 g of N,N-carbonyldiimidazole in 8 ml of tetrahydrofuran is stirred for 2.75 hours at room temperature under argon. To the solution is added 0.316 g of N-L-leucyl)-(S)2-amino-3-cyclohexyl-(R)1-(2-thiazolyl)propan-1-ol and the mixture stirred overnight. The solvent is removed, the residue dissolved in dichloromethane and the solution washed with 10% hydrochloric acid, 10% sodium bicarabonate and dried (Na$_2$SO$_4$). The solvent is removed to give 0.55 g of a white foam. This foam is dissolved in dichloromethane-ethyl acetate (6:4) and the solution filtered through a thin pad of hydrous magnesium silicate. The filtrate is concentrated to dryness to give 0.50 g of white foam; [α]$_D^{26}$−56°±1 (c, 1.054 CH$_3$OH).

EXAMPLE 63

N-[[(S)2-[(4-Acetyl-1-piperazinyl)carbonyl]oxy]-3-phenylpropionyl]-L-leucyl]-(S)2-amino-3-cyclo-hexyl-(R)1-(2-furanyl)propan-1-ol To a solution of 0.568 g of [S-(R*,R*)]-2-[(1-carboxy-3-methylbutyl)amino]-2-oxo-1-(phenylmethyl)ethyl 4-acetyl-1-piperazinecarboxylate and 0.132 g of triethylamine in 15 ml of dichloromethane under argon was added 0.579 g of benzotriazol-1-yloxytris(dimethylamino)phosphonium hexafluorophosphate (BOP) and the mixture stirred for 1 minute. To the mixture is added 0.234 g of (S)-2-amino-3-cyclohexyl-(R)-1-(2-furanyl)propan-1-ol. The mixture is stirred overnight and the solvent removed. The residue is dissolved in ethyl acetate and the solution washed with 10% hydrochloric acid, 2M sodium carbonate, water and dried (MgSO$_4$). The solvent is removed and the residue (0.74 g) dissolved in ethyl acetate-methanol (9:1) and filtered through silica gel and the silica gel washed with ethyl acetate-methanol (9:1). The filtrate was evaporated to give 0.69 g of a clear foam; [α]$_D^{26}$−41°±1 (c. 1.137, CH$_3$OH).

EXAMPLE 64

N-[N-[[(S)2-(1,4-dioxa-8-azaspior[4.5]decane-8-carbonyl)oxy]-3-phenylpropionyl]-L-leucyl]-(S)2-amino-3-cyclohexyl-(R)1-(2-furanyl)propan-1-ol To a solution of 0.458 g of 1,4-dioxa-8-azaspiro[4.5]-decane-8-carboxylic, [S-(R*,R*)]-2-[[1-methoxycarbonyl)-3-methylbutyl]amino]-2-oxo-1-(phenylmethyl)ethyl, ester in 8 ml of methanol is added a solution of 0.056 g of lithium hydroxide in 1 ml of water. After stirring 1.75 hours at room temperature an additional 5 mg of lithium hydroxide is added and the mixture stirred for 1.25 hour. The mixture is concentrated under vacuum and acidified with 3N hydrochloric acid. The mixture is extracted with dichloromethane and the extract dried (MgSO$_4$). The solvent is removed to give 0.42 g of a clear foam.

The preceding compound (0.42 g) is dissolved in 10.5 ml of dichloromethane under argon and 138 μl of triethylamine and 0.437 g of benzotriazol-1-yloxytris (dimethylamino)phosphonium hexafluorophosphate (BOP) is added. After 1 minute 0.176 g of (S)-2-amino-3-cyclohexyl-(R)-1-(2-furanyl)propan-1-ol is added and the mixture stirred overnight at room temperature. The solvent is removed, the residue dissolved in ethyl acetate and the solution washed with 10% hydrochloric acid, 2M sodium carbonate water and dried (MgSO$_4$). The solvent is removed to give 0.55 g of a foam. The solid is chromatographed on silica gel with ethyl acetate-dichloromethane (2:3) as solvent to give 0.52 g of a pale yellow foam; [α]$_D^{26}$−32°±1 (c, 1.073, CH$_3$OH).

EXAMPLE 65

N-[N-[[2-[[[(2-methoxyethyl)amino]carbonyl]oxy]-1-oxo-3-phenylpropyl]-L-leucyl]-(S)2-amino-3-cyclohexyl-(R)1-(2-furanyl)propan-1-ol To a mixture of 5.2 g of methyl L-3-phenyllactate, 0.170 g of activated charcoal in 80 ml of tetrahydrofuran is added 5.23 ml of trichlormethyl chlorocarbonate (diphosgene) and the mixture heated at 55° C. for 2 hours. An additional 1.75 ml of trichloromethyl chlorocarbonate is added and the mixture heated (55° C.) for 1.3 hours. The mixture is cooled and filtered through diatomaceous earth and the filtrate concentrated to dryness. The residue is dissolved in 140 ml of dichloromethane under argon, chilled to 0° C. and 7.54 ml of 2-methoxyethylamine in 16 ml dichloromethane added over 15 minutes. The mixture is stirred at 0° C. overnight, 100 ml of 0.5N hydrochloric acid added and the organic layer separated. The organic layer is washed with 10% sodium bicarbonate, dried (MgSO$_4$) and the solvent removed. The residue is chromatographed on silica by HPLC on a Water-Prep 500-A instrument with 5% ethyl acetate in dichloromethane as solvent. The fractions containing product are evaporated and the residue dissolved in 10% ethyl acetate in dichloromethane, dried (MgSO$_4$) and the solvent removed under vacuum to give 3.54 g of methyl alpha[[[(2-methoxyethyl)amino]carbonyl]oxy]-benzenepropionate as a pale yellow oil.

A mixture of the preceding compound (3.42 g) 45 ml of methanol, 0.638 g of lithium hydroxide in 5.7 ml of water is stirred at room temperature for 3.25 hours. The mixture is filtered and 25 ml of 3N hydrochloric acid added to the filtrate. The mixture is concentrated and the aqueous residue partition between water and ethyl acetate. The organic layer is removed and the aqueous layer extracted with ethyl acetate. The organic layer and extracts are combined, dried (MgSO$_4$) and the solvent removed to give 3.37 g of (R,S)-alpha-[[[(2-methoxyethyl)amino]carbonyl]oxy]benzenepropanoic acid.

A mixture of the preceding compound (3.20 g) 1.94 g of N,N-carbonyldiimidazole in 90 ml of tetrahydrofuran is stirred at room temperature under argon for 2.5 hours. To the solution is added 2.73 g of methyl L-leucinate hydrochloride and the mixture stirred overnight at room temperature. The solvent is removed, the residue dissolved in 80 ml of dichloromethane and the solution washed with 10% hydrochloric acid, 10% sodium bicarbonate and dried (MgSO$_4$). The solvent is removed to give 4.24 g of a viscous yellow oil. This oil is chromatographed on silica gel by HPLC on a Water-Prep 500A instrument with hexane-ethyl acetate (3:2) as solvent to give 3.33 g of methyl [R(and S)]-N-[2-[[[(2-methoxyethyl)amino]carbonyl]oxy]-1-oxo-3-phenylpropyl]-L-leucinate as a yellow gum; $[\alpha]_D^{26} - 17° \pm 1$ (c, 1.038 CH$_3$OH).

The preceding compound (3.1 g) in 40 ml of methanol and 0.445 g of lithium hydroxide in 4 ml of water is stirred at room temperature for 2.5 hours. To the mixture is added 3.5 ml of 3N hydrochloric acid, and the solvent removed. The residue is partitioned between water and dichloromethane. The organic layer is separated, the aqueous layer extracted twice with dichloromethane and the organic layer and extracts combined. The extract is dried (MgSO$_4$) and the solvent removed to give 2.8 g of [R(and S)]-B-[2-[[[(2-methoxyethyl)amino]carbonyl]oxy]-1-oxo-3-phenylpropyl]-L-leucine as a clear foam. A mixture of the preceding compound (0.600 g) 0.160 g of triethylamine and 0.698 g of benzotriazol-1-yltris(dimehtylamino)phosphonium hexafluorphosphate (BOP) is stirred for 1 minute and then 0.294 g of (S)-2-amino-3-cyclohexyl-(R)-1-(2-furanyl)propan-1-ol added. The mixture is stirred overnight at room temperature and the solvent removed. The residue is dissolved in ethyl acetate and the solution washed with 10% hydrochloric acid, 2M sodium carbonate, water and dried (MgSO$_4$). The solvent is removed to give 0.84 g of a pale yellow foam which is chromatographed over silica gel with ethyl acetatedichloromethane (1:1) and then with ethyl acetatedichloromethane (7:3). Fractions containing the major faster moving component are concentrated to give 0.33 g of the product of the Example as a clear gum; $[\alpha]_D^{26} - 31° \pm 2$ (c, 0.596, CH$_3$OH).

EXAMPLE 66

N-[N-[(S)2-[[(4-Oxo-1-piperidinyl)carbonyl]oxy]-3-phenylpropionyl]-L-leucyl]-(S)2-amino-3-cyclo-hexyl-(R)1-(2-furanyl)-propan-1-ol To a solution of 0.104 g of (S)-2-[[(4-oxo-1-piperidinyl)carbonyl]oxy]-3-phenylpropionic acid in 4.5 ml of dichloromethane under argon is added 36 mg of triethylamine and 0.158 g of benzotriazol-1-yloxytris(-dimethylamino)phosphonium hexafluorophosphate(-BOP) and after stirring 1 minute, 0.100 g of N-(L-leucyl)-(S)2-amino-3-cyclohexyl-(R)1-(2-furanyl)propan-1-ol is added. The mixture is stirred at room temperature overnight and the solvent removed. The residue is dissolved in ethyl acetate and washed with 10% HCl, H$_2$O, 2M Na$_2$CO$_3$ and water. The organic layer is dried (MGSO$_4$) and the solvent removed. The residue is dissolved in ethyl acetate-dichloromethane (1:1) and the solution filtered through a pad of silica gel. The pad is washed with ethyl acetatedichloromethane (1:1) and the combined filtrates are concentrated under vacuum to give 0.15 g of white solid; $[\alpha]_D^{26} - 45° \pm 1$ (c, 1.03 CH$_3$OH). FAB mass spectrum Found; 632.3302 (M+Na).

EXAMPLE 67

N-[N-[(S)2-[[(3-Oxo-1-piperazinylcarbonyl]oxy]-3-phenylpropionyl]-L-leucyl]-(S)2-amino-3-cyclohexyl-(R)1-(2-furanyl)propan-1-ol To a solution of 0.20 g of methyl (S)2-[[(3-oxo-1-piperazinyl)carbonyl]oxy]-3-phenylpropionate in 4 ml of methanol is added 41 mg of lithium hydroxide in 1.9 ml of water and the mixture stirred at room temperature for 2 hours. The solvent is removed, 1 ml of water and 3N HCl added until the mixture is acidic. The mixture is extracted dichloromethane and the extract dried (MgSO$_4$) and the solvent removed to give 0.11 g of white solid. The preceding solid (0.11 g) is slurried in 4.6 ml of dichloromethane under argon and 38 mg of triethylamine added. To the solution is added 0.167 g of benzotriazol-1-yloxytris(dimethylamino)phosphonium hexafluorophosphate(BOP]. After 1 minute, 0.106 g of N-(leucyl)-(S)2-amino-3-cyclohexyl-(R)1-(2-furanyl)-propan-1-ol is added and the miture stirred at room temperature overnight. The solvent is removed under vacuum and the residue dissolved in ethyl acetate. The solution is washed with 10% HCl, 2M Na$_2$CO$_3$ and water; dried (MgSO$_4$) and the solvent removed. The residue is dissolved in chloroform-methanol (9:1) and filtered through a pad of silica gel. The pad is washed with chloroform-methanol (9:1) and the combined filtrate concentrated to dryness to give 0.170 g of a clear foam; $[\alpha]_D^{26} - 42° \pm 1$ (c, 1.021, CH$_3$OH).

EXAMPLE 68

N-[N-[(S)2-[(4-Morpholinocartonyl)oxy]-3-cyclohexylpropionyl]-L-leucyl](S)2-amino-3-cyclohexyl-(R)1-(2-furanyl)propan-1-ol As described for Example 66, 0.220 g of N-[(S)2-[(4-morpholinocarbonyl)oxy]-3-cyclohexylpropionyl]-L-leucine in 7 ml of dichloromethane is coupled with 0.102 g of (S)2-amino-3-cyclohexyl-(R)1-(2-furanyl)- propan-1-ol with 0.244 g of BOP as coupling reagent to give 0.28 g of product as a clear foam; $[\alpha]_D^{26} -25° \pm 1$ (c, 1.05, CH$_3$OH).

We claim:

1. A compound of the formula:

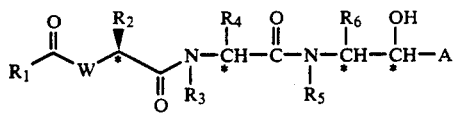

wherein

R$_1$ is:

O-lower alkyl(C$_2$-C$_6$); —N[lower alkyl(C$_1$-C$_6$)]$_2$; OH

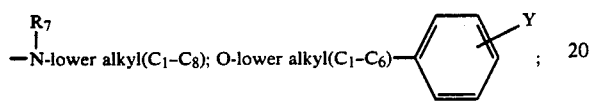

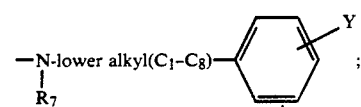

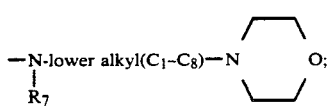

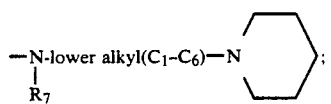

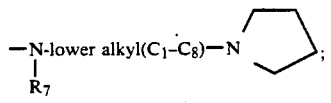

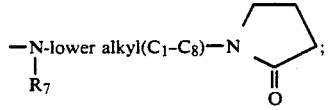

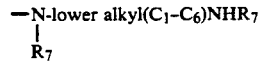

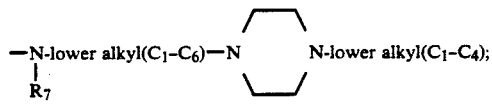

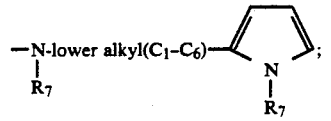

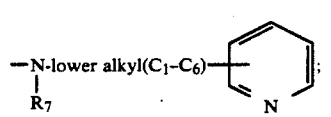

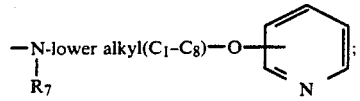

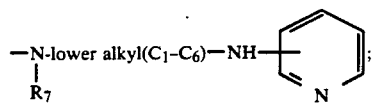

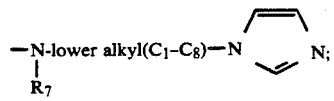

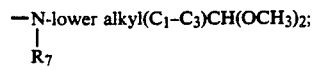

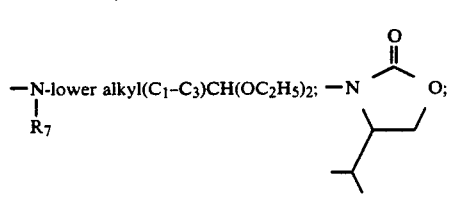

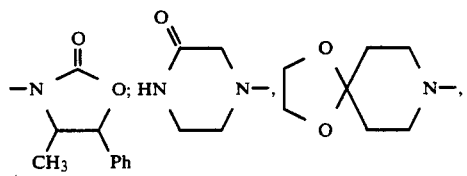

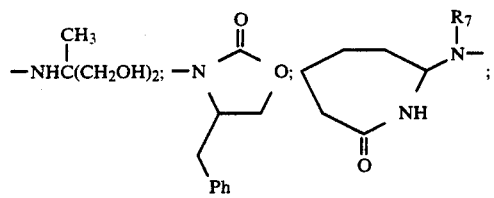

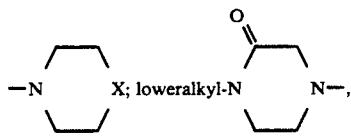

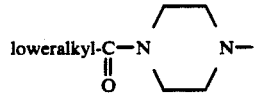

where X = S, O, SO, SO$_2$, NH, N-loweralkyl and Y is OCH$_3$, CH$_3$, F, Cl, or di or tri OCH$_3$ groups; R$_7$ is hydrogen or lower alkyl(C$_1$-C$_3$);

R$_2$ is phenylmethyl, (4-methoxyphenyl)methyl, (3,4-dimethoxyphenyl)methyl, (4-chlorophenyl)methyl, (3-trifluoromethylphenyl)methyl, (3,4,5-trimethoxyphenyl)methyl, 1-naphthalenylmethyl, (2-thienyl)methyl, (3-indolyl)methyl, (benzo[b]thien-3-yl)methyl, (benzo[b]thien-2-yl)methyl, (3-benzofuranyl)methyl, (2-benzofuranyl)methyl; cyclohexylmethyl;

R$_3$ is hydrogen or methyl; R$_4$ is 4-(imidazolyl)CH$_2$X-, alkyl(C$_1$-C$_8$), —alkyl(C$_1$-C$_4$)NH$_2$, phenylmethyl, cyclohexylmethyl, —X-alkyl(C$_1$-C$_8$), —(CH$_2$)$_n$N[- lower alkyl($C_1$-$C_3$)]$_2$, —($CH_2$)$_n$NHlower alkyl(-$C_1$-$C_3$)], X-cyclohexyl, —($CH_2$)$_n$-X-alkyl($C_1$-$C_3$), —X-$CH_2CH_2$N[alkyl-($C_1$-$C_3$)]$_2$ (where X is —O— or —S— and n is 1 to 4) and moieties of the formulae:

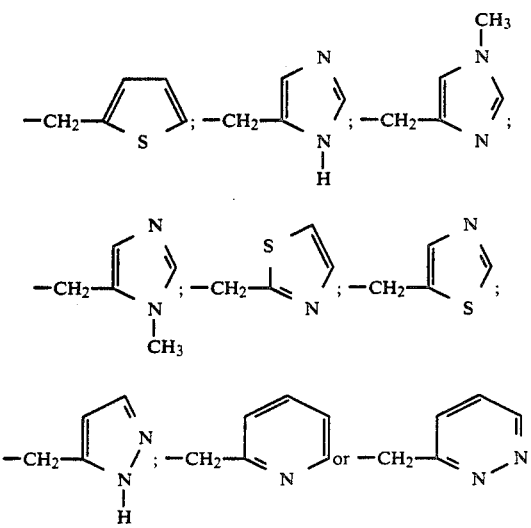

$R_5$ is hydrogen or methyl;
$R_6$ is alkyl($C_1$-$C_6$), phenylmethyl, cyclohexylmethyl, —($CH_2$)$_n$—X-alkyl($C_1$-$C_4$) or

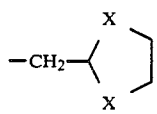

and A is

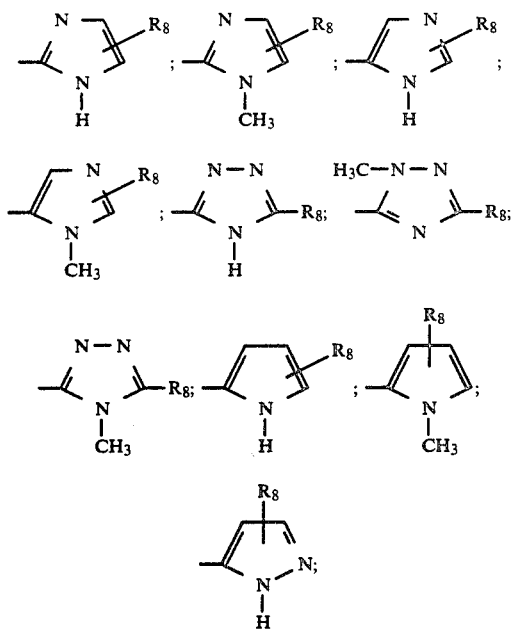

where $R_8$ is hydrogen, alkyl($C_1$-$C_3$) or $COR_9$, where $R_9$ is $NH_2$, OH, —O-alkyl($C_1$-$C_4$), —NH-alkyl($C_1$-$C_4$), —N[alkyl($C_1$-$C_3$)]$_2$, lower alkyl ($C_1$-$C_6$) and where W is $CH_2$ or O, wherein the asymmetric center at the carbon attached to the $R_2$ substituent of the N-terminal unit has the R configuration when W is $CH_2$ and the S configuration when W is O.

2. A compound according to claim 1 wherein the α-amino acids of the formula:

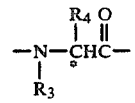

have the natural $\underline{\underline{L}}$ configuration.

3. A compound according to claim 1 wherein the C-terminal are those of the formula:

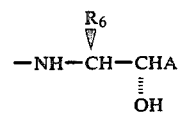

with an anti(threo) relationship between the amino group and the hydroxyl group.

4. A compound according to claim 1 wherein the formula:

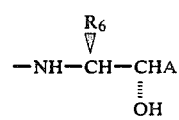

contains the diastereomers with the 1S configuration.

5. A compound according to claim 1 wherein the C terminal group is

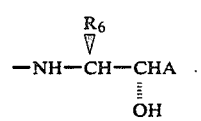

$R_2$ is phenylmethyl, 1-naphthalenylmethyl, (3-indolyl)-methyl, (benzo[b]thien-3-yl)methyl, (3-benzofuranyl)-methyl and $R_2$ in the N-terminal unit of the formula

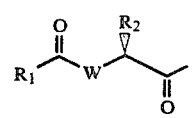

has the R configuration when W=$CH_2$ and the S configuration when W=O (same configuration as L α-amino acids); $R_4$ is 4-(imidazolyl)$CH_2$X—, alkyl(-$C_1$-$C_4$)$NH_2$, —($CH_2$)$_n$-NHlower alkyl($C_1$-$C_3$), —($CH_2$)$_n$N[lower alkyl($C_1$-$C_3$)]$_2$, (4-imidazolyl)-methyl, (3-pyrazolyl)methyl, —X—$CH_2CH_2$N[alkyl(-$C_1$-$C_3$)]$_2$, (3-pyridinyl)methyl, —X—CH($CH_3$)$_2$; $R_6$ is cyclohexylmethyl or

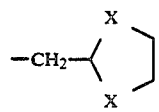

and A is

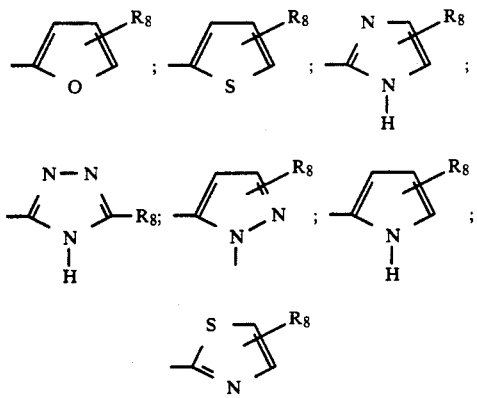

where R₅ is hydrogen or COR₉, where R₉ is as defined in claim 1.

6. The compound according to claim 1 N-[N-[(R)2-(1-naphthalenylmethyl)-3-(tert-butoxycarbonyl)propionyl -L-histidyl]-(S)2-amino-3-cyclohexyl-1-(2-thiazolyl)propan-1-ol.

7. The compound according to claim 1 N-[N-[(R)2-(1-naphthalenylmethyl)-3-(tert-butoxycarbonyl)propionyl]-L-leucyl]-(S)2-amino-4-methyl-(R)1-(2-thiazolyl)pentan-1-ol.

8. The compound according to claim 1 N-[N-[(R)2-(1-naphthalenylmethyl)-3-(morpholinocarbonyl)propionyl]-L-histidyl]-(S)-2-amino-3-cyclohexyl-(R)1-(2amino-2-thienyl)propan-1-ol.

9. A compound according to claim 1 N-[N-[(R)2-(1-naphthalenylmethyl)-3-(morpholinocarbonyl)propionyl]-L-histidyl]-(S)-3-cyclohexyl-(R)1-(2furanyl)-propan-1-ol.

10. A compound according to claim 1 N-[N-[(R)2-(1-naphthalenylmethyl)-3-(morpholinocarbonyl)-propionyl]-L-histidyl]-(S)-2-amino-3-cyclohexyl-(R)1-(5-acetyl-2-furanyl)propan-1-ol.

11. A compound according to claim 1 N-[N-[(R)2-(1-naphthalenylmethyl)-3-(pyrrolidinocarbonyl)-propionyl]-L-histidyl]-(S)2-amino-3-cyclo-hexyl-(R)1-(5-methoxycarbonyl-2-thiazolyl)-propan-1-ol.

12. The compound according to claim 1 N-[N-(R)2-(1-naphthalenylmethyl)-3-([3-(2-oxo-1-pyrrolidinyl)-propylamino]carbonyl)propionyl]-L-leucyl-(S)2-amino-4-methyl-(R)1-(2-thiazolyl)pentan-1-ol.

13. The compound according to claim 1 N-[N-[(R)-2-(1-naphthalenylmethyl)-3-([3-(2-oxo-1-pyrrolidinyl)-propylamino]carbonyl)propionyl]-L-histidyl]-(S)2-amino-3-cyclohexyl-(R)1-(5-ethoxycarbonyl-2-furanyl)propan-1-ol.

14. The compound according to claim 1 N-[N-[(R)-2-(1H-indol-3-ylmethyl)-3-([3-(2-oxo-1-pyrrolidinyl)-propylamino]carbonyl)propionyl]-L-histidyl]-(S)2-amino-3-cyclohexyl-(R)1-(4-acetyl-2-imidazolyl)-propan-1-ol.

15. The compound according to claim 1 N-[N-[(R)-2-(1-naphthalenylmethyl)-3-([2-(2-pyridinyloxy)ethylamino]carbonyl)propionyl]-L-leucyl]-(S)2-amino-3-cyclohexyl-(R)1-(5-acetyl-2-furanyl)propan-1-ol.

16. The compound according to claim 1 N-[N-[(R)-2-(1-naphthalenylmethyl)-3-(S)-[(hexahydro-2-oxo-1H-azepin-3-yl)amino]carbonyl)propionyl]-L-leucyl]-(S)2-amino-4-methyl-(R)1-(2-thiazolyl)pentan-1-ol.

17. The compound according to claim 1 N-[N-[(R)-2-(1-naphthalenylmethyl)-3-([2-pyridinylmethylamino]-carbonyl)propionyl]-L-leucyl]-(S)2-amino-4-methyl-1-(R)1-(2-thiazolyl)pentan-1-ol.

18. The compound according to claim 1 N-[N-[(R)-2-(1-naphthalenylmethyl)-3-([2-pyridinylmethylamino]-carbonyl)propionyl]-L-leucyl]-(S)2-amino-3-cyclohexyl-(R)1-(5-acetyl-2-furanyl)propan-1-ol.

19. The compound according to claim 1 N-[N-[(R)-2-(1H-indol-3-ylmethyl)-3-([3-pyridinylmethylamino]carbonyl)propionyl]-L-leucyl]-(S)2-amino-3-cyclohexyl-(R)1-(2-furanyl)propan-1-ol.

20. The compound according to claim 1 N-[N-[(R)-2-(1H-indol-3-ylmethyl)-3-(morpholinocarbonyl)-propionyl]-L-histidyl]-(S)2-amino-3-cyclohexyl-(R)1-(5-acetyl-2-furanyl)propan-1-ol.

21. The compound according to claim 1 N-[N-[(R)2-(1H-indol-3-ylmethyl)-3-([3-(1H-imidazol-1-yl)propylamino]carbonyl)propionyl]-L-histidyl]-(S)2-amino-3-cyclohexyl-(R)1-(2-thienyl)propan-1-ol.

22. The compound according to claim 1 N-[N-[(R)2-(1H-indol-3-ylmethyl)-3-([3-(1H-imidazol-1-yl)propylamino]carbonyl)propionyl]-L-histidyl]-(S)2-amino-3-cyclohexyl-(R)1-(2-furanyl)propan-1-ol.

23. The compound according to claim 1 N-[N-[(R)2-(1H-indol-3-ylmethyl)-3-([3-(1H-imidazol-1-yl)propylamino]carbonyl)propionyl]-L-leucyl]-(S)2-amino-3-cyclohexyl-(R)1-(5-ethoxycarbonyl-2-furanyl)propan-1-ol.

24. The compound according to claim 1 N-[N-[(R)2-(1-naphthalenylmethyl)-3-([2,2-diethoxyethylamino]-carbonyl)propionyl]-L-histidyl]-(S)2-amino-3-cyclohexyl-(R)-1-(2-imidazolyl)propan-1-ol.

25. The compound according to claim 1 N-[N-[(R)2-(3-benzofuranylmethyl)-3-([2,2-diethoxyethylamino]-carbonyl)propionyl]-L-histidyl]-(S)2-amino-3-cyclohexyl-(R)1-(2-furanyl)propan-1-ol.

26. The compound according to claim 1 N-[N-[[(R)2-(benzo[b]thien-3-ylmethyl)-3-(morpholinocarbonyl)-propionyl]-L-histidyl]-(S)2-amino-3-cyclohexyl-(R)1-(5-acetyl-2-furanyl)propan-1-ol.

27. The compound according to claim 1 N-[N-[(R)2-(benzo[b]thien-3-ylmethyl)-3-(morpholinocarbonyl)propionyl]-L-histidyl]-(S)2-amino-3-cyclohexyl-(R)1-(5-acetyl-2-thiazolyl)propan-1-ol.

28. The compound according to claim 1 N-[N-[(R)2-(1H-indol-3-ylmethyl)-3-([2-(2-pyridinyl)ethylamino]carbonyl)propionyl]-L-leucyl]-(S)2-amino-3-cyclohexyl-(R)1-(2,-imidazolyl)propan-1-ol.

29. The compound according to claim 1 N-[N-[(R)2-(1H-indol-3-ylmethyl)-3-(morpholinocarbonyl)propionyl]-L-histidyl]-(S)2-amino-3-cyclohexyl-(R)1-(1H-pyrazol-3-yl)propan-1-ol.

30. The compound according to claim 1, N-[N-[(R)2-(1-naphthalenylmethyl)-3-(morpholinocarbonyl)propionyl]-L-histidyl]-(S)2-amino-3-cyclohexyl-(R)-1-(1H-pyrazol-3-yl)propan-1-ol.

31. The compound according to claim 1 N-[N-[(R)2-(3-benzofuranylmethyl)-3-(morpholinocarbonyl)propionyl]-L-histidyl]-(S)2-amino-3-cyclohexyl-(R)-1-(1H-pyrazol-3-yl)propan-1-ol.

32. A compound according to claim 1 N-[N-[[(S)2-(4-Morpholinocarbonyl)oxy]-3-phenylpropionyl]-L-leucyl]-(S)2-amino-3-cyclohexyl-(R)1-(2- propan-1-ol.

33. A compound according to claim 1 N-[N-[[(S)2-[(4-acetyl-1-piperazinyl)oxy]-3-phenylpropionyl]-L-leucyl]-(S)2-amino-3-cyclohexyl-(R)1-(2-furanyl)propan-1-ol.

34. A compound according to claim 1, N-[N-[(S)2-[[(4-oxo-1-piperidinyl)carbonyl]oxy]-3-phenylpropionyl]-L-leucyl]-(S)2-amino-3-cyclohexyl-(R)1-(2-furanyl)-propan-1-ol.

35. A compound according to claim 1, N-[N-[(S)2-[[(3-oxo-1-piperazinyl)carbonyl]oxy]-3-phenylpropionyl]-L-leucyl]-(S)2-amino-3-cyclohexyl-(R)1-(2-furanyl)propan-1-ol.

36. A compound according to claim 1, N-[N-[(S)2-[[(4-morpholinocarbonyl)oxy]-3-cyclohexylpropionyl]-L-leucyl](S)2-amino-3-cyclohexyl-(R)1-(2-furanyl)propan-1-ol.

37. A method of treating hypertension in a warm-blooded animal which comprises administering to the animal a hypotensive amount of a compound of claim 1.

38. A parenteral composition in dosage unit form comprising a compound of claim 1 and a parenterally acceptable carrier.